United States Patent
Butler et al.

(10) Patent No.: US 10,988,498 B2
(45) Date of Patent: Apr. 27, 2021

(54) PROCESSES AND INTERMEDIATES FOR THE PREPARATION OF 1'-SUBSTITUTED CARBA-NUCLEOSIDE ANALOGS

(71) Applicant: GILEAD SCIENCES, INC., Foster City, CA (US)

(72) Inventors: Thomas Butler, Redwood City, CA (US); Aesop Cho, Mountain View, CA (US); Benjamin R. Graetz, San Mateo, CA (US); Choung U. Kim, San Carlos, CA (US); Samuel E. Metobo, Newark, CA (US); Oliver L. Saunders, San Mateo, CA (US); Andrew W. Waltman, San Francisco, CA (US); Jie Xu, Foster City, CA (US); Lijun Zhang, Los Altos Hills, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 16/011,055

(22) Filed: Jun. 18, 2018

(65) Prior Publication Data
US 2018/0327437 A1    Nov. 15, 2018

Related U.S. Application Data

(63) Continuation of application No. 12/886,248, filed on Sep. 20, 2010, now Pat. No. 10,023,600.

(60) Provisional application No. 61/244,299, filed on Sep. 21, 2009.

(51) Int. Cl.
| | | |
|---|---|---|
| C07H 1/00 | (2006.01) | |
| C07H 19/23 | (2006.01) | |
| A61K 31/7056 | (2006.01) | |
| A61K 31/706 | (2006.01) | |
| A61K 31/7052 | (2006.01) | |

(52) U.S. Cl.
CPC ............. *C07H 1/00* (2013.01); *C07H 19/23* (2013.01); *A61K 31/706* (2013.01); *A61K 31/7052* (2013.01); *A61K 31/7056* (2013.01)

(58) Field of Classification Search
CPC .... C07H 13/08; C07H 19/23; A61K 31/7056; A61K 31/7064
See application file for complete search history.

(56) References Cited

U.S. PATENT DOCUMENTS

| | | |
|---|---|---|
| 4,816,570 A | 3/1989 | Farquhar |
| 4,968,788 A | 11/1990 | Farquhar |
| 5,663,159 A | 9/1997 | Starrett, Jr. et al. |
| 5,792,756 A | 8/1998 | Starrett, Jr. et al. |
| 6,312,662 B1 | 11/2001 | Erion et al. |
| 6,475,985 B1 | 11/2002 | Wagner et al. |
| 6,476,030 B1 | 11/2002 | Carling et al. |
| 6,656,915 B1 | 12/2003 | Bantia et al. |
| 6,909,011 B2 | 6/2005 | Skranc et al. |
| 7,105,493 B2 | 9/2006 | Sommadossi et al. |
| 7,125,855 B2 | 10/2006 | Bhat et al. |
| 7,176,203 B2 | 2/2007 | Chambers et al. |
| 7,268,119 B2 | 9/2007 | Cook et al. |
| 7,285,658 B2 | 10/2007 | Cook et al. |
| 7,368,437 B1 | 5/2008 | Bojack et al. |
| 7,390,791 B2 | 6/2008 | Becker et al. |
| 7,429,571 B2 | 9/2008 | Chand et al. |
| 7,514,410 B2 | 4/2009 | Babu et al. |
| 7,560,434 B2 | 7/2009 | Babu et al. |
| 7,598,230 B2 | 10/2009 | Cook et al. |
| 7,608,597 B2 | 10/2009 | Sommadossi et al. |
| 7,713,941 B2 | 5/2010 | Cook et al. |
| 7,803,788 B2 | 9/2010 | Becker et al. |
| 7,807,653 B2 | 10/2010 | Cook et al. |
| 7,842,672 B2 | 11/2010 | Boojamra et al. |
| 7,951,787 B2 | 5/2011 | McGuigan |
| 7,973,013 B2 | 7/2011 | Cho et al. |
| 7,994,139 B2 | 8/2011 | Babu et al. |

(Continued)

FOREIGN PATENT DOCUMENTS

| | | |
|---|---|---|
| AU | 2010295392 B2 | 4/2012 |
| CA | 2367921 C | 7/2009 |

(Continued)

OTHER PUBLICATIONS

Cho, et al., Discovery of the First C-Nucleoside HCV Polymerase Inhibitor (GS-6620) with Demonstrated Antiviral Response in HCV Infected Patients, J. Med. Chem., 2014, pp. 1812-1825, vol. 57, No. 5.

(Continued)

*Primary Examiner* — Leigh C Maier
(74) *Attorney, Agent, or Firm* — Fish & Richardson P.C.

(57) ABSTRACT

Provided are processes and intermediates for the syntheses of nucleosides of pyrrolo[1,2-f][1,2,4]triazinyl and imidazo [1,2-f][1,2,4]triazinyl heterocycles of Formula I.

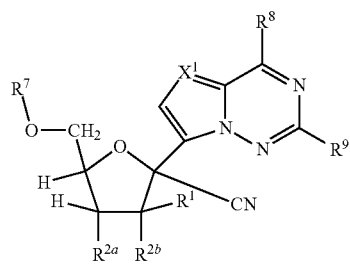

Formula I

1 Claim, No Drawings

(56) References Cited

U.S. PATENT DOCUMENTS

| | | |
|---|---|---|
| 8,008,264 B2 | 8/2011 | Butler et al. |
| 8,012,941 B2 | 9/2011 | Cho et al. |
| 8,012,942 B2 | 9/2011 | Butler et al. |
| 8,071,568 B2 | 12/2011 | Narjes et al. |
| 8,119,607 B2 | 2/2012 | Francom et al. |
| 8,242,085 B2 | 8/2012 | Babu et al. |
| 8,318,682 B2 | 11/2012 | Butler et al. |
| 8,415,308 B2 | 4/2013 | Cho et al. |
| 8,455,451 B2 | 6/2013 | Cho et al. |
| 8,853,171 B2 | 10/2014 | Butler et al. |
| 8,871,737 B2 | 10/2014 | Smith et al. |
| 8,889,159 B2 | 11/2014 | Clearly et al. |
| 8,980,865 B2 | 3/2015 | Wang |
| 9,090,642 B2 | 7/2015 | Cho et al. |
| 9,243,022 B2 | 1/2016 | Beigelman et al. |
| 9,249,174 B2 | 2/2016 | Beigelman et al. |
| 9,278,990 B2 | 3/2016 | Smith et al. |
| 9,388,208 B2 | 7/2016 | Clarke et al. |
| 9,393,256 B2 | 7/2016 | Ray et al. |
| 9,481,703 B2 | 11/2016 | Kalayanov et al. |
| 9,487,544 B2 | 11/2016 | Cho et al. |
| 9,504,701 B2 | 11/2016 | Casola et al. |
| 9,540,411 B2 | 1/2017 | Kalayanov et al. |
| 9,542,154 B2 | 1/2017 | Rubanovich et al. |
| 9,549,941 B2 | 1/2017 | Cleary et al. |
| 9,605,018 B2 | 3/2017 | Wang et al. |
| 9,616,076 B2 | 4/2017 | Casola et al. |
| 9,701,682 B2 | 7/2017 | Clarke et al. |
| 9,724,360 B2 | 8/2017 | Chun et al. |
| 9,828,408 B2 | 11/2017 | Kalayanov et al. |
| 9,949,994 B2 | 4/2018 | Chun et al. |
| 10,023,600 B2 | 7/2018 | Butler et al. |
| 10,034,893 B2 | 7/2018 | Luly et al. |
| 10,059,716 B2 | 8/2018 | Clarke et al. |
| 10,065,958 B2 | 9/2018 | Mackman et al. |
| 10,251,898 B2 | 4/2019 | Chun et al. |
| 10,251,904 B2 | 4/2019 | Clarke et al. |
| 10,377,761 B2 | 4/2019 | Clarke et al. |
| RE47,589 E | 9/2019 | McGuigan |
| 10,695,361 B2 | 6/2020 | Clarke et al. |
| 2003/0050229 A1 | 3/2003 | Sommadossi et al. |
| 2003/0092775 A1 | 5/2003 | Ernst et al. |
| 2004/0006002 A1 | 1/2004 | Sommadossi et al. |
| 2004/0023901 A1 | 2/2004 | Cook et al. |
| 2004/0063658 A1 | 4/2004 | Roberts et al. |
| 2004/0067901 A1 | 4/2004 | Bhat et al. |
| 2004/0138170 A1 | 7/2004 | Montgomery et al. |
| 2005/0187180 A1 | 8/2005 | Loeb et al. |
| 2005/0209166 A1 | 9/2005 | Eckhardt et al. |
| 2005/0215513 A1 | 9/2005 | Boojamra et al. |
| 2005/0250728 A1 | 11/2005 | Bantia et al. |
| 2006/0058303 A1 | 3/2006 | Chambers et al. |
| 2006/0142238 A1 | 6/2006 | Mcguigan |
| 2006/0241064 A1 | 10/2006 | Roberts et al. |
| 2008/0107628 A1 | 5/2008 | Boojamra et al. |
| 2008/0161324 A1 | 7/2008 | Johansen et al. |
| 2008/0280842 A1 | 11/2008 | MacCoss et al. |
| 2009/0004138 A1 | 1/2009 | Francom et al. |
| 2009/0221524 A1 | 9/2009 | Kotra et al. |
| 2009/0233879 A1 | 9/2009 | Reddy et al. |
| 2009/0317361 A1 | 12/2009 | Cho et al. |
| 2010/0015094 A1 | 1/2010 | Babu et al. |
| 2010/0016251 A1 | 1/2010 | Sofia et al. |
| 2010/0021425 A1 | 1/2010 | Butler et al. |
| 2010/0035835 A1 | 2/2010 | Narjes et al. |
| 2010/0035836 A1 | 2/2010 | Francom et al. |
| 2010/0203015 A1 | 8/2010 | Butler et al. |
| 2010/0234584 A1 | 9/2010 | Chang |
| 2010/0249068 A1 | 9/2010 | Beigelman et al. |
| 2010/0291031 A2 | 11/2010 | Francom et al. |
| 2010/0298257 A1 | 11/2010 | Ross et al. |
| 2011/0070194 A1 | 3/2011 | Cho et al. |
| 2011/0084230 A1 | 4/2011 | Knochel et al. |
| 2011/0230654 A1 | 9/2011 | Butler et al. |
| 2011/0257122 A1 | 10/2011 | Sofia et al. |
| 2011/0293563 A1 | 12/2011 | Cho et al. |
| 2012/0009147 A1 | 1/2012 | Cho et al. |
| 2012/0020921 A1 | 1/2012 | Cho et al. |
| 2012/0027752 A1 | 2/2012 | Mackman et al. |
| 2012/0071434 A1 | 3/2012 | Smith et al. |
| 2012/0107274 A1 | 5/2012 | Clarke et al. |
| 2013/0034521 A1 | 2/2013 | Butler et al. |
| 2013/0143835 A1 | 6/2013 | Eneroth et al. |
| 2013/0281686 A1 | 10/2013 | Cho et al. |
| 2013/0315868 A1 | 11/2013 | Mayes |
| 2013/0344028 A2 | 12/2013 | Butler et al. |
| 2014/0219958 A1 | 8/2014 | Luly |
| 2015/0111839 A1 | 4/2015 | Mackman et al. |
| 2015/0133395 A1 | 5/2015 | Clarke et al. |
| 2015/0152116 A1 | 6/2015 | Mackman et al. |
| 2016/0058779 A1 | 3/2016 | Casola et al. |
| 2016/0122356 A1 | 5/2016 | Axt et al. |
| 2016/0122374 A1 | 5/2016 | Chun |

FOREIGN PATENT DOCUMENTS

| | | |
|---|---|---|
| CN | 1291994 A | 4/2001 |
| CN | 1443189 A | 9/2003 |
| CN | 1498221 A | 5/2004 |
| CN | 1852915 A | 10/2006 |
| CN | 101043893 A | 9/2007 |
| CN | 101611046 A | 12/2009 |
| CN | 102906102 A | 1/2013 |
| EA | 201071170 A1 | 8/2011 |
| EA | 201171417 A1 | 5/2012 |
| EA | 201200525 A1 | 9/2012 |
| EP | 2480559 B1 | 8/2012 |
| EP | 2396340 B1 | 12/2013 |
| JP | 41017629 | 10/1966 |
| JP | 2004520367 A | 7/2004 |
| JP | 2008502685 A | 1/2008 |
| JP | 2008518934 A | 6/2008 |
| TW | 1401084 B | 7/2013 |
| WO | WO-1991/019721 A1 | 12/1991 |
| WO | WO-2000/56734 A1 | 9/2000 |
| WO | WO-2000506734 A1 | 9/2000 |
| WO | WO-2000075157 A1 | 12/2000 |
| WO | WO-2001/32153 A2 | 5/2001 |
| WO | WO-2001/60315 A2 | 8/2001 |
| WO | WO-2001/90121 A2 | 11/2001 |
| WO | WO-2002/008241 | 1/2002 |
| WO | WO-2002/18404 A2 | 3/2002 |
| WO | WO-2002/32920 A2 | 4/2002 |
| WO | WO-2002/057287 A2 | 7/2002 |
| WO | WO-2002/057425 A2 | 7/2002 |
| WO | WO-2003/093272 A1 | 11/2003 |
| WO | WO-2003/093273 A1 | 11/2003 |
| WO | WO 2003/100009 A2 | 12/2003 |
| WO | WO-2004/046331 A2 | 6/2004 |
| WO | WO-2005/009418 A2 | 2/2005 |
| WO | WO 2005/092877 A1 | 10/2005 |
| WO | WO-2005/123087 A2 | 12/2005 |
| WO | WO-2006/031725 A2 | 3/2006 |
| WO | WO-2006031725 A2 | 3/2006 |
| WO | WO-2006/050161 A2 | 5/2006 |
| WO | WO-2006/065335 A2 | 6/2006 |
| WO | WO-2006/121820 A1 | 11/2006 |
| WO | WO-2007/027248 A2 | 3/2007 |
| WO | WO-2007/056170 A2 | 5/2007 |
| WO | WO-2007056170 A2 | 5/2007 |
| WO | WO-2007/064883 A2 | 6/2007 |
| WO | WO-2007/065289 A2 | 6/2007 |
| WO | WO-2007062542 A2 | 6/2007 |
| WO | WO-2007064883 A2 | 6/2007 |
| WO | WO-2007/064931 A2 | 6/2007 |
| WO | WO-2007/065829 A1 | 6/2007 |
| WO | WO-2007/097991 A2 | 8/2007 |
| WO | WO 2007/113294 A1 | 10/2007 |
| WO | WO-2007/135134 A1 | 11/2007 |
| WO | WO-2008/005542 A2 | 1/2008 |
| WO | WO-2008/055870 A1 | 5/2008 |
| WO | WO-2008/079206 A1 | 7/2008 |
| WO | WO-2008/082601 A2 | 7/2008 |
| WO | WO-2008/085508 A2 | 7/2008 |

(56) References Cited

FOREIGN PATENT DOCUMENTS

| WO | WO-2008/089105 A2 | 7/2008 |
|---|---|---|
| WO | WO-2008089105 A2 | 7/2008 |
| WO | WO-2008/116064 A2 | 9/2008 |
| WO | WO-2008116064 A2 | 9/2008 |
| WO | WO-2008/121634 A2 | 10/2008 |
| WO | WO-2008/141079 A1 | 11/2008 |
| WO | WO-2008141079 A1 | 11/2008 |
| WO | WO-2009/009951 A1 | 1/2009 |
| WO | WO-2009/131926 A1 | 10/2009 |
| WO | WO-2009/132123 A1 | 10/2009 |
| WO | WO-2009/132135 A1 | 10/2009 |
| WO | WO-2009131926 A1 | 10/2009 |
| WO | WO-2009132123 A1 | 10/2009 |
| WO | WO-2009132135 A1 | 10/2009 |
| WO | WO-2010/002877 A2 | 1/2010 |
| WO | WO-2010002877 A2 | 1/2010 |
| WO | WO-2010036407 A2 | 4/2010 |
| WO | WO-2010/093608 A1 | 8/2010 |
| WO | WO-2010/099458 A1 | 9/2010 |
| WO | WO-2010/135569 A1 | 11/2010 |
| WO | WO-2011/011303 | 1/2011 |
| WO | WO-2010/111381 A3 | 3/2011 |
| WO | WO-2011/035231 A1 | 3/2011 |
| WO | WO-2011/035250 A1 | 3/2011 |
| WO | WO-2011080568 A2 | 7/2011 |
| WO | WO-2011/123645 A2 | 10/2011 |
| WO | WO-2011/123672 A1 | 10/2011 |
| WO | WO-2011/150288 A1 | 12/2011 |
| WO | WO-2012/012465 A1 | 1/2012 |
| WO | WO-2012/012776 A1 | 1/2012 |
| WO | WO-2012/039787 A1 | 3/2012 |
| WO | WO-2012/039791 A1 | 3/2012 |
| WO | WO-2012039791 A1 | 3/2012 |
| WO | WO-2012/051570 A1 | 4/2012 |
| WO | WO-2012142523 | 10/2012 |
| WO | 2012158643 A1 | 11/2012 |
| WO | WO-2013/084165 A1 | 6/2013 |
| WO | WO-2014/042433 A2 | 3/2014 |
| WO | WO-2014033617 | 3/2014 |
| WO | WO-2014/078778 A2 | 5/2014 |
| WO | WO-2014078463 | 5/2014 |
| WO | WO-2014/116755 A1 | 7/2014 |
| WO | WO-2014169280 | 10/2014 |
| WO | WO-2015/069939 A1 | 5/2015 |
| WO | WO-2016/069825 A1 | 5/2016 |
| WO | WO-2016/069826 A1 | 5/2016 |
| WO | WO-2016/069827 A1 | 5/2016 |
| WO | WO-2017/184668 A1 | 10/2017 |
| WO | WO-2017/049060 A1 | 3/2018 |
| WO | WO-2018204198 A1 | 11/2018 |

OTHER PUBLICATIONS

Knaggs, et al. A QSAR Study Investigating the Effect of L-Alanine Ester Variation on the Anti-HIV Activity of Some Phosphoramidate Derivatives of d4T, 2000, pp. 2075-2078.

Lu, Chengping, Veterinary Microbiology 5th edition, Jan. 31, 2013, p. 431, China Agriculure Press (No English Translation available).

Mcguigan, et al. Application of Phosphoramidate ProTide Technology Significantly Improves Antiviral Potency of Carbocyclic Adenosine Derivatives, 2006, pp. 7215-7226.

Patil, et al., Synthesis of Pyrrolo[2,1-f][1,2,4]triazine Congeners of Nucleic Acid Purines via the N-Amination of 2-Substituted Pyrroles, J. Het. Chem., 1994, pp. 781-786, vol. 31. Porter, et al., Zika virus, drug discovery, and student projects, ScienceBlogs, Mar. 9, 2016, 7 pages.

Porter, et al., Zika virus, drug discovery, and student projects, ScienceBlogs, Mar. 9, 2016, 7 pages.

Venkatachalam, T.K. et al. Effect of change in nucleoside structure on the activation and antiviral activity of phosphoramidate derivatives, 2005, pp. 5408-5423.

Warren, et al., Therapeutic efficacy of the small molecules GS-5734 against EBOLA virus in rhesus monkeys, Nature, Mar. 17, 2016, 19 pages.

Barl, et al., The halogen/magnesium-exchange using iPrMgCl•LiCl and related exchange reagents, Heterocycles, Jan. 2014, pp. 827-844, vol. 88, No. 2.

Cho, et al., Practical synthesis of 1'-substituted Tubercidin C-nucleoside analogs, Tetrahedron Letters, Feb. 2012, pp. 484-486, vol. 53, No. 5.

Japanese Patent Office, Notice of Reasons for Rejection for Japanese Patent Appln. No. JP 2017-52094, dated Mar. 30, 2018.

U.S. Appl. No. 12/428,176, filed Apr. 22, 2009.
U.S. Appl. No. 12/428,234, filed Apr. 22, 2009.
U.S. Appl. No. 12/885,917, filed Sep. 20, 2010.
U.S. Appl. No. 12/886,248, filed Sep. 20, 2010.

Alessandrini, et al., Synthesis of Differently Protected 1-C-methyl-ribofuranoses Intermediates for the Preparation of Biologically Active 1'-C-methyl-ribonucleosides, Journal of Carbohydrate Chemistry, 2008, pp. 332-344, vol. 27, No. 5.

Ali, et al., Quantitative structure-activity relationships (QSAR) of two series of O-aryl or N-acyl O-ethyl phosphoramidate and phosphorodiamidate fungicides incorporating amino acid ethyl esters, Bulletin of Environmental Contamination and Toxicology, 2000, pp. 415-420, vol. 65, No. 4.

Arimilli, M.N., et al., Synthesis, In Vitro Biological Evaluation and Oral Bioavailability of 9-[2-(phosphonomethoxy)propyl]adenine (PMPA) Prodrugs, Antiviral Chemistry & Chemotherapy, 1997, pp. 557-564, vol. 8, No. 6.

ARIPO Form 21 and Substantive Examination Report (in English) for AP Application No. AP/P/2010/005439, Mar. 18, 2014.

ARIPO Patent Office, Official Action (ARIPO Form No. 18) with Substantive Search and Examination Report for AP Application No. AP/P/2010/005414, dated Mar. 14, 2014.

ARIPO Patent Office, Search and Exam Report for AP Application No. AP/P/2012/006189, dated Jun. 26, 2014.

ARIPO Patent Office, Search Report for AP Patent Application No. AP/P/2011/005818, dated Sep. 19, 2013.

Asbun, et al., Synthesis of 5-substituted Pyrimidines. II, Journal of Organic Chemistry, 1968, pp. 140-142, vol. 31.

Australia Patent Office, Patent Examination Report No. 1 for AU Application No. 2011280910, dated Jun. 10, 2014.

Australia Patent Office, Patent Examination Report No. 1 for AU Application No. 2011306066, dated Nov. 21, 2013.

Australia Patent Office, Patent Examination Report No. 1 for AU Patent Application No. 2010213873, dated Jun. 4, 2014.

Australia Patent Office, Patent Examination Report No. 1 for AU Patent Application No. 2010295392, dated Sep. 16, 2014.

Australia Patent Office, Patent Examination Report No. 1 for AU Patent Application No. 2011282241, dated Jul. 9, 2014.

Ballini, et al., Enantioselective Synthesis of the Lactone Moiety of the Mevinic Acids using D-Xylose as a Chiral Precursor, Journal of the Chemical Society, Perkin Transactions 1, 1991, pp. 490-491.

Balzarini, et al., Inhibition of feline (FIPV) and human (SARS) coronavirus by semisynthetic derivatives of glycopeptide antibiotics, Antiviral Research, Mar. 14, 2006, pp. 20-33, vol. 72.

Bandini, et al., Indium tribromide: a highly effective catalyst for the addition of trimethylsilyl cyanide to α-hetero-substituted ketone, Tetrahedron Letters, 2001, pp. 3041-3043. vol. 42.

Barker, et al., 2,3,5-Tri-O-benzyl-D-ribosyl and -L-arabinosyl Bromides, Journal of Organic Chemistry, 1961, pp. 4605-4609, vol. 26, No. 11.

Belokon, et al., Optimized catalysts for the asymmetric addition of trimethylsilyl cyanide to aldehydes and ketones, Tetrahedron, 2001, pp. 771-779, vol. 57.

Benksim, et al., A Novel Stereospecific Synthesis of Glycosyl Cyanides from 1,2-O-sulfinyl Derivatives, Organic Letters, 2004, pp. 3913-3915, vol. 6, No. 22.

Benzaria, et al., Synthesis, In Vitro Antiviral Evaluation, and Stability Studies of Bis(S-acyl-2-thioethyl) Ester Derivatives of 9-[2-(phosphonomethoxy)ethyl]adenine (PMEA) as Potential PMEA prodrugs with Improved Oral Bioavailability, J. Med. Chem., 1996, pp. 4958-4965, vol. 39, No. 25.

(56) References Cited

OTHER PUBLICATIONS

Bio, et al., Practical Synthesis of a Potent Hepatitis C Virus RNA Replication Inhibitor, J. Org. Chem., 2004, pp. 6257-6266, vol. 69, No. 19.
Bobeck, et al., Advances in Nucleoside Monophosphate Prodrugs as Anti-HCV Agents, Antiviral Therapy, 2010, pp. 935-950, vol. 15.
Bojack, et al., Design and synthesis of inhibitors of adenosine and AMP deaminases, Organic Letters, 2001, pp. 839-842, vol. 3, No. 6.
Boyer, et al., Pathogenesis, diagnosis and management of hepatitis C, Journal of Hepatology, 2000, pp. 98-112, vol. 32.
Bozza, Zika Outbreak, Brazil 2015, ISARIC, 2015, 28 pages.
Brown, Progress towards improving antiviral therapy for hepatitis C virus polymerase inhibitors. Part O: Nucleoside analogues, 2009, pp. 709-725, vol. 18.
Bullard-Feibelman, et al., The FDA-approved drug Sofosbuvir inhibits Zika Virus infection, Antiviral Res., Jan. 1, 2018, pp. 134-140, vol. 137.
Burns, A glimmer of hope for a fatal feline disease, American Veterinary Medical Association, Dec. 15, 2017, 5 pages.
Butora, et al., Synthesis and HCV inhibitory properties of 9-deaza- and 7,9-dideaza-7-oxa-2'-C-methyladenosine, Bioorganic & Medicinal Chemistry, 2007, pp. 5219-5229, vol. 15, No. 15.
Cabirol, et al., Robust and Efficient, yet Uncatalyzed, Synthesis of Triarylsilyl-protected Cyanohydrins from Ketones, 2008, pp. 2446-2449, vol. 73.
Caira, Crystalline Polymorphism of Organic Compounds, Topics in Current Chemistry, 1998, pp. 163-208, vol. 198.
Calès, et al., Treatment of liver fibrosis: clinical aspects, Gastroentérologie Clinique et Biologique, 2009, pp. 958-966, vol. 33, No. 10-11.
Calisher, et al., Antigenic Relationships between Flaviviruses as Determined by Cross-neutralization Tests with Polyclonal Antisera, Journal of General Virology, 1989, pp. 37-43, vol. 70.
Camps, Studies on Structurally Simple -αβ-butenolides-II, Tetrahedron, 1982, pp. 2395-2402, vol. 38, No. 15.
Canadian Patent Office, Office Action for CA Patent Application No. 2,773,772, dated Aug. 12, 2014.
Carroll, Robust Antiviral Efficacy upon Administration of a Nucleoside Analog to Hepatitis C Virus-Infected Chimpanzees, Antimicrobial Agents and Chemotherapy, 2009, pp. 926-934, vol. 53, No. 3.
Chapman, et al., RSV604, a Novel Inhibitor of Respiratory Syncytial Virus Replication, Antimicrobial Agents and Chemotherapy, 2007, pp. 3346-3353, vol. 51, No. 9.
Chile Patent Office, Opposition filed Against CL Patent Application 00076-2013, Jun. 18, 2014.
Chile Patent Office, Opposition for CL Patent Application No. 727-2013, Oct. 15, 2013.
Chile Patent Office, Second Office Action for CL Patent Application No. 1906-2011, dated Oct. 16, 2013.
Chinese Patent Office, ffice Action for CN Patent Application No. 200980114224.2, dated Nov. 30, 2012.
Chinese Patent Office, Notification of Reexamination for CN Patent Application No. 200980120218.8, dated Sep. 1, 2014.
Chinese Patent Office, Notification of the First Office Action and Search Report for CN Patent Application No. 201080041902.X, dated Nov. 12, 2013.
Chinese Patent Office, Notification of the First Office Action for CN Patent Application No. 201180035776.1, dated Feb. 27, 2014.
Chinese Patent Office, Notification of the First Office Action, with Search Report, for CN Patent Application No. 201080041946.2, dated Dec. 18, 2013.
Chinese Patent Office, Notification of the Second Office Action & Search Report for CN Patent Application No. 201080011690.0, dated Jan. 8, 2014.
Chinese Patent Office, Notification of the Third Office Action for CN Patent Application No. 201080011690.0, dated Jul. 29, 2014.
Chinese Patent Office, Office Action for CN Patent Application No. 200980114224.2, dated Aug. 19, 2013.
Chinese Patent Office, Office Action with Search Report for CN Patent Application No. 201180035281.9, dated Jun. 27, 2014.
Chinese Patent Office, Rejection Decision for CN Patent Application No. 200980120218.8, dated Feb. 7, 2014.
Chinese Patent Office, Second Examination Report for CN Patent Application No. 200980120218.8, dated Jun. 21, 2013.
Cho, et al., Synthesis and antiviral activity of a series of 1'-substituted 4-aza-7,9-dideazaadenosine C-nucleosides, Bioorg Med Chem Letters, 2012, pp. 2705-2707, vol. 22.
Cihlar, et al., Design and Profiling of GS-9148, a Novel Nucleotide Analog Active against Nucleoside-resistant Variants of Human Immunodeficiency Virus Type 1, and Its Orally Bioavailable Phosphonoamidate Prodrug, GS-9131, Antimicrobial Agents and Chemotherapy, 2008, pp. 655-665, vol. 52, No. 2.
Clark, et al., Design, Synthesis, and Antiviral Activity of 2'-Deoxy-2'-fluoro-2'-C-methylcytidine, a Potent Inhibitor of Hepatitis C Virus Replication, Journal of Medicinal Chemistry, 2005, pp. 5504-5508, vol. 48, No. 17.
Clarke, et al., Discovery of [beta]-d-2'-deoxy-2'-[alpha]-fluoro-4'[alpha]-cyano-5-aza-7,9-dideaza adenosine as a potent nucleoside inhibitor of respiratory syncytial virus with excellent selectivity over mitochondrial, BioOrganic & Medicinal Chemistry Letters, Apr. 29, 2015, pp. 2484-2487, vol. 25, No. 12.
Colacino, et al., Synthesis and Biological Evaluation of Some 5-Nitro- and 5-Amino Derivatives of 2'-Deoxycytidine, 2',3'-Dideoxyuridine, and 2',3'-Dideoxycytidine, Nucleoside, Nucleotides & Nucleic Acids, 2003, pp. 2013-2026, vol. 22, No. 11.
Columbia Patent Office, Office Action for CO Application No. 13 004212, dated Dec. 4, 2013.
Columbia Patent Office, Office Action for CO Patent Application No. 11-109.501, dated Nov. 27, 2012.
Columbia Patent Office, Office Action for CO Patent Application No. 13-235103-1, dated Aug. 27, 2014.
Columbia Patent Office, Resolution No. 56673 for CO Patent Application No. 10131479, Sep. 27, 2013.
Columbia Patent Office, Resolution No. 72986 for CO Patent Application No. 10121513-5, Dec. 23, 2013.
Columbia Patent Office, Second Examination Report (in English) for CO Patent Application No. 10-131479, dated Jun. 20, 2013.
Columbian Patent Office, Office Action No. 425 for CO Patent Application No. 12 050 579, dated Jan. 21, 2014.
Communication pursuant to Article 94(3) EPC for EP Patent Application No. 10763083.2, dated May 2, 2014.
Communication pursuant to Article 94(3) EPC for EP Patent Application No. 11715792.5, dated Feb. 14, 2014.
Communication under 161/162 for EP Patent Application No. 10704068.5, dated Sep. 6, 2011.
Communication under 161/162 for EP Patent Application No. 10763083.2, dated May 11, 2012.
Communication under 161/162 for EP Patent Application No. 11715792.5, dated Apr. 26, 2013.
Communication under 161/162 for EP Patent Application No. 11743400.1, dated Feb. 26, 2013.
Communication under 161/162 for EP Patent Application No. 11743709.5, dated Mar. 1, 2013.
Dai, et al., Synthesis of 2'-C-β-Fluoromethyluridine, Organic Letters, 2003, pp. 807-810, vol. 5, No. 6.
De Clercq, Antiviral Drugs: Current State of the Art, J. Clin. Virol., 2001, pp. 73-89, vol. 22, No. 1.
De Clercq, Molecular Targets for Antiviral Agents, The Journal of Pharmacology and Experimental Therapeutics, 2001, pp. 1-10, vol. 297, No. 1.
De Francesco, et al., Approaching a New Era for Hepatitis C Virus Therapy: Inhibitors of the NS3-4A Serine Protease and the NS5B RNA-Dependent RNA Polymerase, Antiviral Research, 2003, pp. 1-16, vol. 58, No. 1.
De Las Heras, Synthesis of Ribosyl and Arabinosyl Cyanides by Reaction of 1-O-Acyl Sugars with Trimethylsilyl Cyanide, Journal of the Chemical Society, Perkin Transactions 1, 1982, pp. 903-907.
De Lombaert, et al., N-Phosphonomethyl Dipeptides and Their Phosphonate Prodrugs, a New Generation of Neutral Endopeptidase (NEP, EC 3.4.24.11) Inhibitors, J. Med. Chem., 1994, pp. 498-511, vol. 37, No. 4.

(56) References Cited

OTHER PUBLICATIONS

Di Bisceglie, et al., The Unmet Challenges of Hepatitis C, Scientific American, Oct. 1999, pp. 80-85.
Dolzhenko, et al., Pyrazolo[1,5-a][1,3,5]Triazines(5-Aza-9-Deazapurines): Synthesis and Biological Activity, Heterocycles, 2008, pp. 1575-1622, vol. 75, No. 7.
Domingo, et al., The quasispecies (extremely heterogeneous) nature of viral RNA genome populations: biological relevance—a review, Gene, 1985, pp. 1-8, vol. 40.
Dondoni, et al., Thiazole-Based Synthesis of Formyl C-Glycosides, Journal of Organic Chemistry, 1994, pp. 6404-6414, vol. 59.
Dudfield, et al., Synthesis of C-ribosyl 1,2,4-triazolo[3,4-f][1,2,4]triazines as Inhibitors of Adenosine and AMP Deaminasses, J. Chem. Soc., Perkin Trans. 1, 1999, pp. 2937-2942.
Dymock, et al., Novel approaches to the treatment of hepatitis C virus infection, Antiviral Chemistry & Chemotherapy, 2000, pp. 79-96, vol. 11, No. 2.
Ecuador Patent Office, Opposition for EC Patent Application No. SP-13-12451, Apr. 23, 2014.
Ecuador Patent Office, Opposition for EC Patent Application No. SP-2012-11817, May 27, 2013.
Ecuador Patent Office, Statement of Opposition for EC Patent Application No. SP-10-10609, Mar. 31, 2011.
El Safadi, et al., 5-Modified-2'-dU and 2'-dC as Mutagenic Anti HIV-1 Proliferation Agents: Synthesis and Activity, Journal of Medicinal Chemistry, 2010, pp. 1534-1545, vol. 53, No. 4.
El Salvador Patent Office, Official Action for SV National Phase Entry of International Application No. PCT/US2010/049471, dated Nov. 6, 2013.
English translation of Office Action for MX Application No. Mx/a/2013/003179, dated Feb. 25, 2014.
Eurasian Patent Office, Office Action for EA Patent Application No. 201390152, dated Apr. 14, 2014.
Eurasian Patent Office, Official Action for EA Patent Application No. 201390133, dated Mar. 27, 2014.
Eurasian Patent Office, Second Examination Report for EA Patent Application No. 201071128, dated Oct. 24, 2012.
Eurasian Patent Office, Second Examination Report for EA Patent Application No. 201071170, dated Oct. 25, 2012.
Eurasian Patent Office, Second Office Action for EA Patent Application No. 201190110/28, dated Jan. 28, 2013.
Eurasian Patent Office, Third Examination Report for EA Patent Application No. 201071128, dated Apr. 29, 2013.
Eurasian Patent Office, Third Examination Report for EA Patent Application No. 201071170, dated Oct. 10, 2013.
Eurasian Patent Office, Third Office Action for EA Application No. 201190110/28, dated Oct. 18, 2013.
European Patent Office, International Preliminary Report on Patentability and Written Opinion for PCT International Application No. PCT/US2009/041432, dated Oct. 26, 2010, 7 pages.
European Patent Office, International Preliminary Report on Patentability and Written Opinion for PCT International Application No. PCT/US2010/049471, dated Mar. 27, 2012, 7 pages.
European Patent Office, International Preliminary Report on Patentability and Written Opinion for PCT International Application No. PCT/US2011/038253, dated Dec. 4, 2012, 6 pages.
European Patent Office, International Preliminary Report on Patentability and Written Opinion for PCT International Application No. PCT/US2011/044581, dated Jan. 22, 2013, 7 pages.
European Patent Office, International Preliminary Report on Patentability for PCT International Application No. PCT/US2009/041447, dated Oct. 26, 2010, 7 pages.
European Patent Office, International Preliminary Report on Patentability for PCT International Application No. PCT/US2010/023586, dated Aug. 16, 2011, 6 pages.
European Patent Office, International Preliminary Report on Patentability for PCT International Application No. PCT/US2011/028897, dated Mar. 26, 2013, 7 pages.
European Patent Office, International Preliminary Report on Patentability for PCT International Application No. PCT/US2011/029441, dated Mar. 26, 2013, 7 pages.
European Patent Office, International Preliminary Report on Patentability for PCT International Application No. PCT/US2011/045102, dated Jan. 22, 2013, 5 pages.
European Patent Office, International Preliminary Report on Patentability for PCT International Application No. PCT/US2015/057932, dated May 2, 2017, 11 pages.
European Patent Office, International Preliminary Report on Patentability for PCT International Application No. PCT/US2015/057933, dated May 2, 2017, 7 pages.
European Patent Office, International Preliminary Report on Patentability for PCT International Application No. PCT/US2015/057934, dated May 11, 2017, 14 pages.
European Patent Office, International Search Report and Written Opinion for PCT International Application No. PCT/US2015/057934, dated Mar. 18, 2016, 20 pages.
European Patent Office, International Search Report and Written Opinion for PCT International Application No. PCT/US2017/028251, dated Sep. 13, 2017, 22 pages.
European Patent Office, International Search Report and Written Opinion for PCT International Application No. PCT/US2018/022166, dated May 25, 2018, 13 pages.
European Patent Office, International Search Report and Written Opinion for PCT International Application No. PCT/US2018/029974, dated Sep. 18, 2018, 21 pages.
European Patent Office, International Search Report for PCT International Application No. PCT/US2010/023586, dated Aug. 4, 2010, 4 pages.
European Patent Office, International Search Report for PCT International Application No. PCT/US2011/038253, dated Jul. 29, 2011, 4 pages.
European Patent Office, International Search Report for PCT International Application No. PCT/US2011/044581, dated Nov. 7, 2011, 4 pages.
European Patent Office, International Search Report for PCT International Application No. PCT/US2016/052092, dated Oct. 11, 2016, 11 pages.
European Patent Office, International Search Report for PCT International Application No. PCT/US2018/0022166, dated Jun. 11, 2018, 18 pages.
European Patent Office, International Search Report for PCT International Application No. PCT/US2018/022166, dated Jun. 11, 2018, 18 pages.
European Patent Office, International Search Report for PCT International Application No. PCT/US2009/041432, dated Aug. 11, 2009, 5 pages.
European Patent Office, International Search Report issued in International Application No. PCT/US2010/049471, dated Nov. 18, 2010, 5 pages.
European Patent Office, International Search Report issued in International Application No. PCT/US2010/049508, dated Nov. 5, 2010, 4 pages.
European Patent Office, International Search Report issued in International Application No. PCT/US2011/028897, dated Aug. 1, 2011, 6 pages.
European Patent Office, International Search Report issued in International Application No. PCT/US2011/029441, dated Aug. 1, 2011, 5 pages.
European Patent Office, International Search Report issued in International Application No. PCT/US2011/045102, dated Nov. 9, 2011, 4 pages.
European Patent Office, International Search Report issued in International Application No. PCT/US2009/041447, dated Aug. 7, 2009, 5 pages.
European Patent Office, Written Opinion and ISR for International Application No. PCT/US2015/057933, dated Jan. 21, 2016, 9 pages.
European Patent Office, Written Opinion and ISR for PCT International Application No. PCT/ US2015/057934, dated May 6, 2016, 20 pages.

(56) References Cited

OTHER PUBLICATIONS

European Patent Office, Written Opinion and ISR for PCT International Application No. PCT/US2015/057932, dated May 6, 2016, 7 pages.
European Patent Office, Written Opinion for PCT International Application No. PCT/US2010/023586, dated Aug. 4, 2010, 5 pages.
European Patent Office, Written Opinion for PCT International Application No. PCT/US2011/028897, dated Aug. 1, 2011, 6 pages.
European Patent Office, Written Opinion for PCT International Application No. PCT/US2011/029441, dated Aug. 1, 2011, 6 pages.
European Patent Office, Written Opinion for PCT International Application No. PCT/US2011/038253, dated Jul. 29, 2011, 5 pages.
European Patent Office, Written Opinion for PCT International Application No. PCT/US2011/044581, dated Nov. 7, 2011, 6 pages.
European Patent Office, Written Opinion for PCT International Application No. PCT/US2011/045102, dated Nov. 9, 2011, 4 pages.
European Patent Office, Written Opinion issued in International Application No. PCT/US2009/041447, dated Oct. 26, 2010, 7 pages.
European Patent Office, Written Opinion issued in International Application No. PCT/US2010/049471, dated Mar. 27, 2012, 7 pages.
European Patent Office, Written Opinion issued in International Application No. PCT/US2010/049508, dated Mar. 27, 2012, 6 pages.
European Patent Office, Written Opinion issued in International Application No. PCT/US2011/045102, dated Jan. 22, 2013, 5 pages.
European Patent Office, Written Opinion issued in International Application No. PCT/US2017/028243, dated Aug. 29, 2017, 12 pages.
Extended European Search Report for EP Application No. 13194605.5, dated Mar. 13, 2014.
Farquhar, et al., Biologically Reversible Phosphate-Protective Groups, Journal of Pharmaceutical Sciences, 1983, pp. 324-325, vol. 72, No. 3.
First Examination Report (in English) for CO Patent Application No. 10-131479, dated Oct. 23, 2012.
First Examination Report (in English) for MX Patent Application No. MX/a/2010/011661, dated Oct. 26, 2011.
First Examination Report for AU Patent Application No. 2009240630, dated Jun. 14, 2012.
First Examination Report for AU Patent Application No. 2009240642, dated Aug. 2, 2012.
First Examination Report for CN Patent Application No. 200980120218.8, dated Nov. 13, 2012.
First Examination Report for CO Patent Application No. 10-121513-5, dated Dec. 10, 2012.
First Examination Report for EA Patent Application No. 201071128, dated Apr. 25, 2012.
First Examination Report for EA Patent Application No. 201071170, dated Apr. 25, 2012.
First Examination Report for ID Patent Application No. W00 2010 03923, dated Apr. 5, 2013.
First Examination Report for ID Patent Application No. W00 2010 03957, dated Apr. 25, 2013.
First Examination Report for IL Patent Application No. 208515, dated Jan. 6, 2013.
First Examination Report for IL Patent Application No. 208701, dated Jan. 13, 2013.
First Examination Report for JP Patent Application No. 2011-506429, dated Aug. 22, 2013.
First Examination Report for JP Patent Application No. 2011-506435, dated Aug. 22, 2013.
First Examination Report for NZ Patent Application No. 588400, dated Apr. 11, 2011.
First Examination Report for NZ Patent Application No. 588670, dated Apr. 8, 2011.
First Examination Report for NZ Patent Application No. 608070, dated Nov. 7, 2013.
First Examination Report for TW Patent Application No. 098113324, dated Oct. 30, 2012.
First Examination Report for UA Patent Application No. 2010 13030, dated Mar. 2, 2013.
First Examination Report for VN Patent Application No. 1-2010-02653, dated Apr. 26, 2012.
First Examination Report for VN Patent Application No. 1-2010-02939, dated Apr. 19, 2012.
First Office Action for CL Patent Application No. 1906-2011, received May 7, 2013.
First Office Action for CN Patent Application No. 201080011960.0, dated Jun. 8, 2013.
First Office Action for EA Patent Application No. 201190110/28, dated Apr. 26, 2012.
First Office Action for EA Patent Application No. 201390141/28, with English translation, dated Aug. 14, 2014.
First Office Action for EP Patent Application No. 10704068.5, dated Jun. 18, 2012.
First Office Action for IL Patent Application No. 214396, dated Jul. 8, 2013.
First Office Action for UA Application No. a 2011 10568, received Apr. 7, 2014.
First Office Action for VN Patent Application No. 1-2012-03895, dated Feb. 8, 2013.
Form 21 for AP Patent Application No. AP/P/2011/005818, Sep. 19, 2013.
Fukumoto, et al., Viral Dynamics of Hepatiis C Early After Orthotopic Liver Transplantation: Evidence for Rapid Turnover of Serum Virions, Hepatology, 1996, pp. 1351-1354, vol. 24.
Further Examination Report for NZ Application No. 594370, dated Oct. 8, 2013.
Garcia, et al., Synthesis of (2,3,4,6-tetra-O-acetyl-alpha-D-glycopyranosyl)thiophene derivatives as new C-nucleoside analogues, J. Carbohydrate Chemistry, 2001, pp. 681-687, vol. 20, No. 7/8.
Gardelli, et al., Phosphoramidate Prodrugs of 2'-C-Methylcytidine for Therapy of Hepatitis C Virus Infection, Journal of Medicinal Chemistry, 2009, pp. 5394-5407, vol. 52, No. 17.
Gleeson, et al., Prediction of the Potency of Inhibitors of Adenosine Deaminase by QM/MM Calculations, Chem. Commun., 2003, pp. 2180-2181.
Gordon, et al., Control of Hepatitis C: A Medicinal Chemistry Perspective, J. Med. Chem., 2005, pp. 1-20, vol. 48, No. 1.
Greene, et al., Protective groups in organinc synthesis, 1991, 15 pages, John Wiley & Sons, Inc.
Gudmundsson, et al., Synthesis of imidazo[1,2-a]pyridine C-Nucleosides with an Unexpected Site of Ribosylation, Journal of Organic Chemistry, 1997, pp. 3453-3459, vol. 62.
Gudmundsson, et al., The Condensation of 2,6-dichloroimidazo[1,2-a]pyridine C-nucleoside with an Unexpected Site of Ribosylation, Tetrahedron Letters, 1996, pp. 2365-2368, vol. 7, No. 14.
Gunic, et al., Cyclic monophosphate prodrugs of base-modified 2'-C-methyl ribonucleosides as potent inhibitors of hepatitis C virus RNA replication, Bioorganic & Medicinal Chemistry Letters, 2007, pp. 2452-2455, vol. 17.
Hamann, et al., Synthesis and antiviral evaluation of 7,9-dideaza-8-thiapurine C-nucleoside derivatives, Collection Symposium Series, 2008, pp. 347-349, vol. 10.
Hamann, et al., Synthesis and antiviral evaluation of thieno[3,4-d]pyrimidine C-nucleoside analogues of 2',3'-dideoxy- and 2',3'-dideoxy-2',3'-didehydro-adenosine and -inosine, Bioorganic & Medicinal Chemistry, 2009, pp. 2321-2326, vol. 17.
Han, et al., Synthesis of 1-Chloroacetyl-1-dehydroxp2,3,5-tri-O-benzoyl-β-D-ribofuranose. A Potentially Versatile Intermediate for the Synthesis of C-Nucleosides, Synthetic Communications, 1992, pp. 2815-2822, vol. 22, No. 19.
Haraguchi, et al., Stereoselective synthesis of 1'-C-Branched uracil nucleosides from uridine, Nucleosides & Nucleotides, 1995, pp. 417-420, vol. 14, Nos. 3-5.
Harki, et al., Synthesis and Antiviral Activity of 5-Substituted Cytidine Analogues: Identification of Potent Inhibitor of Viral RNA-Dependent RNA Polymerases, Journal of Medicinal Chemistry, 2006, pp. 6166-6169, vol. 49, No. 21.

(56) References Cited

OTHER PUBLICATIONS

Hayashi, et al., A synthesis of 2-substituted 7-(B-D-Ribofuranosyl)-pyrrolo[2,1,f]-1,2,4-Trianzines. A new type of "purine-like" C-nucleoside, Heterosycles, 1992, vol. 34, No. 3.
Hecker, et al., Liver Targeted Prodrugs of 2'-C-Methyladenosine for Therapy of Hepatitis C Virus Infection, J. Med. Chem., 2007, pp. 3891-3896, vol. 50, No. 16.
Hoffmann, et al., When, in the context of drug design, can a fluorine atom successfully substitute a hydroxyl group?, International Journal of Quantum Chemistry, 2002, pp. 419-427, vol. 89.
Indonesia Patent Office, Substantive Examination Report Stage 1 for ID Application No. W-00201103126, dated Jun. 10, 2014.
Israel Patent Office, Notification of Defects for IL Patent Application No. 208515, dated Aug. 25, 2014.
Israel Patent Office, Notification of Defects for IL Patent Application No. 214396, dated Nov. 11, 2013.
Israel Patent Office, Notification of Defects for IL Patent Application No. 218599, dated Aug. 25, 2014.
Israel Patent Office, Notification of Defects for IL Patent Applicaton No. 208701, dated Aug. 25, 2014.
Israel Patent Office, Notification Prior to Examination for IL Patent Application No. 218599, dated Nov. 13, 2012.
Israel Patent Office, Notification Prior to Examination for IL Patent Application No. 218752, dated Jan. 20, 2014.
Israel Patent Office, Supplement to First Examination Report for IL Patent Application No. 208515, dated Jan. 15, 2013.
Itoh, Divergent and stereocontrolled approach to the synthesis of uracil nucleosides branched at the anomeric position, J. Org. Chem., 1995, pp. 656-662, vol. 60.
Japanese Patent Office, Notice of Reasons for Rejection for JP Application No. 2011-549324, dated Jul. 28, 2014.
Japanese Patent Office, Notice of Reasons for Rejection for JP Application No. 2011-549324, dated Mar. 26, 2014.
Japanese Patent Office, Notification of Reasons for Rejection for JP Patent Application No. 2012-529958, dated Aug. 5, 2014.
Japanese Patent Office, Notification of Reasons for Rejection for JP Patent Application No. 2012-529963, dated Aug. 28, 2014.
Jasko, et al., 5'-Phosphonates of Ribonucleosides and 2'-Deoxyribonucleosides: Synthesis and Antiviral Activity, Nucleosides & Nucleotides, 1993, pp. 879-893, vol. 12, No. 8.
Kabat, et al., Nucleosides, CXLVIII, Synthesis of 6-(β-D-Ribofuranosyl)picolinamide: A Novel C-Nucleoside from D-Ribonolactone, Chemical & Pharmaceutical Bulletin, 1988, pp. 634-640, vol. 36, No. 2.
Khamnei, et al., Neighboring Group Catalysis in the Design of Nucleotide Prodrugs, J. Med. Chem., 1996, pp. 4109-4115, vol. 39, No. 20.
Kim, et al., Reversal of the Progression of Fatal Coronavirus Infection in Cats by a Broad-Spectrum Coronavirus Protease Inhibitor, PLOS Pathogens, Mar. 30, 2016, p. e1005531, vol. 12, No. 3.
Klumpp, et al., The Novel Nucleoside Analog R1479 (4'-Azidocytidine) is a Potent Inhibitor of NS5B-dependent RNA Synthesis and Hepatitis C virus Replication in Cell Culture, Journal of Biological Chemistry, 2006, pp. 3793-3799, vol. 281, No. 7.
Knutsen, et al., Synthesis of imidazo-fused bridgehead-nitrogen 2'-deoxyribo-c-nucleosides: coupling-elimination reactions of 2,5-anhydro-3,4,6-tri-O-benzoyl-D-allonic acid, J. Chem. Soc. Perkin Trans., 1985, pp. 621-630.
Knutsen, et al., Synthesis of imidazo-fused bridgehead-nitrogen C-nucleosides via dehydrative coupling reactions of 2,5-anhydro-3,4,6-tri-O-benzoyl-D-allonic acid, J. Chem. Soc. Perkin Trans., 1984, pp. 229-238.
Kobe, et al., Use of Distance Geometry Approach for the In Vitro Antiviral Activity Evaluation of N-bridgehead C-nucleosides, European J. Med. Chem., 1992, pp. 259-266, vol. 27, No. 3.
Lefebvre, et al., Mononucleoside Phosphotriester Derivatives with S-Acyl-2-thioethyl Bioreversible Phosphate-Protecting Groups: Intracellular Delivery of 3'-Azido-2',3'-dideoxphymidine 5'-Monophosphate, Journal of Medicinal Chemistry, 1995, pp. 3941-3950, vol. 38, No. 20.
Lefebvre, et al., Synthesis, Decomposition Pathways and 'In Vitro' Evaluation of Bioreversible Phosphotriesters of Azt, Nucleosides, Nucleotides & Nucleic Acids, 1995, pp. 763-766, vol. 14, No. 3-5.
Lindell, et al., Synthesis and Biochemical Testing of 3-(Carboxyphenylethyl)imidazo[2,1-f][1,2,4]triazines as Inhibitors of AMP Deaminase, ACS Medicinal Chemistry Letters, 2010, pp. 286-289, vol. 1, No. 6.
Lovelette, 1,2,4-Triazines. Synthesis of selected members of the s-triazolo[3,4-f][1,2,4]triazine and tetrazolo[1,5-f][1,2,4]triazine ring systems, Journal of Heterocyclic Chemistry, 1979, pp. 555-560, vol. 16.
Martell, et al., Hepatitis C Virus (HCV) Circulates as a Population of Different but Closely Related Genomes: Quasispecies Nature of HCV Genome Distribution, Journal of Virology, 1992, pp. 3225-3229, vol. 6695.
Mason, et al., Polyadenylation-dependent screening assay for respiratory syncytial virus RNA transcriptase activity and identification of an inhibitor, Nucleic Acids Research, 2004, pp. 4758-4767, vol. 32, No. 16.
Matulic-Adamic, et al., Synthesis of 3-(β-D-Ribofuranosyl)-2-Fluoropyridine and 3-(β-D-Ribofuranosyl)-Pyridin-2-one, Tetrahedron Letters, 1997, pp. 203-206, vol. 38, No. 2.
Matulic-Adamic, et al., Synthesis of 5-(β-D-Ribofuranosyl)-Pyridin-2-one: a 'Deletion-Modified' Analogue of Uridine, Tetrahedron Letters, 1997, pp. 1669-1672, vol. 38, No. 10.
McGuigan, et al., Intracellular Delivery of Bioactive AZT Nucleotides by Aryl Phosphate Derivatives of AZT, J. Med. Chem., 1993, pp. 1048-1052, vol. 36, No. 8.
Meppen, et al., Cyclic phosphoramidates as prodrugs of 2'-C-methylcytidine, European Journal of Medicinal Chemistry, 2009, pp. 3765-3770, vol. 49, No. 9.
Meppen, et al., Medi-404—A Prodrug Approach for the Treatment of HCV Infection, Abstracts of papers, 236th ACS National Meeting, Philadelphia, PA, United States, Aug. 17-21, 2008.
Metobo, et al., Practical synthesis of 10-substituted Tubercidin C-nucleoside analogs, Tetrahedron Letters, 2011, pp. 484-486, vol. 53.
Mexico Patent Office, Office Action for MX Application No. MX/a/2011/008409, dated Mar. 25, 2014.
Mexico Patent Office, Office Action for MX Application No. MX/a/2013/000656, dated Apr. 22, 2014.
Mexico Patent Office, Office Action for MX Application No. MX/a/2013/000656, dated Aug. 4, 2014.
Mexico Patent Office, Office Action for MX Application No. MX/a/2013/000744, dated Apr. 22, 2014.
Migliaccio, et al., Characterization of Resistance to Non-obligate Chain-terminating Ribonucleoside Analogs That Inhibit Hepatitis C Virus Replication in vitro, The Journal of Biological Chemistry, 2003, pp. 49164-49170, vol. 278, No. 49.
Mitchell, et al., Bioreversible Protection for the Phospho Group: Bioactivation of the Di(4-acyloxybenzyl) and Mono(4-acyloxybenzyl) Phosphoesters of Methylphosphonate and Phosphonoacetate, J. Chem. Soc., Perkin Trans. 1, 1992, pp. 2345-2353.
Mitchell, et al., Synthesis of C-Nucleoside Isosteres of 9-(2-Hydroxyethoxymethyl)guanine (Acyclovir), J. Het. Chem., 1984, pp. 697-699, vol. 21, No. 3.
Moennig, et al., The Pestiviruses, Advances in Virus Research, 1992, pp. 53-98, vol. 41.
Moradpour, et al., Replication of hepatitis C virus, Nature Reviews Microbiology, 2007, pp. 453-463, vol. 5, No. 6.
Moscow, et al., Reduced Folate Carrier Gene (RFC1) Expression and Anti-Folate Resistance in Transfected and Non-Selected Cell Lines, International Journal of Cancer, 1997, pp. 184-190, vol. 72.
Murakami, et al., Mechanism of Activation of Beta-D-2'-Fluoro-2'-C-Methylcytidine and Inhibition of Hepatitis C Virus NS5B RNA Polymerase, Antimicrob Agents Chemother., Feb. 2007, pp. 503-509, vol. 51, No. 2.
Murphy, et al., The nucleoside analog GS-441524 strongly inhibits feline infections peritonitis (FIP) virus in tissue culture and experimental cat infection studies, Veterinary Microbiology, ND, pp. 226-233, vol. 219.

(56) References Cited

OTHER PUBLICATIONS

Neumann, et al., Hepatitis C Viral Dynamics in Vivo and the Antiviral Efficacy of Interferon-α Therapy, Science, 1998, pp. 103-107, vol. 282.
New Zealand Patent Office, Second Examination Report and Notice of Acceptance for NZ Patent Application No. 588400, dated Jul. 27, 2012.
Nishimura, et al., Synthesis of pyrrolo[2,1-f][1,2,4]triazine C-nucleosides. Isosteres of sangivamycin, tubercidin, and toyocamycin, Carbohydrate Research, 2001, pp. 77-82, vol. 331.
Ogura, et al., Reaction of Ethynyl Compounds with Lactones, Journal of Organic Chemistry, 1972, pp. 72-75, vol. 37, No. 1.
Otter, et al., Conformational properties of purine-like c-nucleosides, Nucleosides & Nucleotides, 1996, pp. 793-807, vol. 15, Nos. 1-3.
Pankiewicz, et al., C-Nucleoside Analogues of Nicotinamide Mononucleotide (NMN), Nucleosides and Nucleotides, 1988, pp. 589-593, vol. 7, No. 5&6.
Pankiewicz, et al., Efficient Synthesis of 5-(β-D-Ribofuranosyl)nicotinamide and its α-Isomer, Journal of Organic Chemistry, 1988, pp. 3473-3479, vol. 53.
Patil, 4-Aza-7,9-Dideazaadenosine, a new cytotoxic synthetic C-nucleoside analogue of adenosine, Tetrahedron Letters, 1994, pp. 5339-5342, vol. 35, No. 30.
Patil, et al., C-Glycosylation of Substituted Heterocycles under Friedel-Crafts Conditions (II): Robosylation of Multi-Functionalized Thiophenes and Furans for the Synthesis of Purine-Like C-Nucleosides, Nucleosides & Nucleotides, 1990, pp. 937-956, vol. 9, No. 7.
Patil, et al., Synthesis of some new thieno[3,4-d]pyrimidines and their C-nucleosides, Journal of Heterocyclic Chemistry, 1993, pp. 509-515, vol. 30, No. 2.
Perrone, et al., Application of the Phosphoramidate ProTide Approach to 4'-Azidouridine Confers Sub-micromolar Potency versus Hepatitis C Virus on an Inactive Nucleoside, Journal of Medicinal Chemistry, 2007, pp. 1840-1849, vol. 50, No. 8.
Peru Patent Office, Office Action in PE Application No. 1464, dated Sep. 12, 2013.
Piccirilli, et al., A Direct Route to 3-(D-Ribofuranosyl)pyridine Nucleosides, Helvetica Chimica Acta, 1991, pp. 397-406, vol. 74.
Pierra, et al., Synthesis and Pharmacokinetics of Valopicitabine (NM283), and Efficient Prodrug of the Potent Anti-HCV Agent 2'-C-Methylcytidine, Journal of Medicinal Chemistry, 2006, pp. 6614-6620, vol. 49, No. 22.
Poduch, et al., Design of Inhibitors of Orotidine Monophosphate Decarboxylase Using Bioisosteric Replacement and Determination of Inhibition Kinetics, Journal of Medicinal Chemistry, 2006, pp. 4937-4945, vol. 49, No. 16.
Puech, et al., Intracellular Delivery of Nucleoside Monophosphates through a Reductase-mediated Activation Process, Antiviral Research, 1993, pp. 155-174, vol. 22, No. 4.
Ramasamy, et al., Synthesis and Antitumor Activity of Certain 3-B-D-Ribofuranosyl-1,2,4-triazolo[3,4-f]-1,2,4-triazines Related to Formycin Prepared via Ring Closure of a 1,2,4-Triazine Precursor, J. Med. Chem., 1986, pp. 2231-2235, vol. 29, No. 11.
Rao, et al., C-Glycosylation of Substituted Heterocycles under Friedel-Crafts Conditions (I): A Two-Step Synthesis of the Thieno[3,4-d]Pyrimidine C-Nucleoside Analog of Inosine, Tetrahedron Letters, 1988, pp. 3537-3540, vol. 29, No. 29.
Reddy, et al., Stereoselective Synthesis of Nucleoside Monophosphate HepDirect™ Prodrugs, Tet. Lett. 2005, pp. 4321-4324, vol. 46.
Sacramento, et al., The clinically approved antiviral drug Sofosbuvir inhibits Zika Virus replication, Nature, Jan. 18, 2017.
Schul, et al., A Dengue Fever Viremia Model in Mice Shows Reduction in Viral Replication and Suppression of the Inflammatory Response after Treatment with Antiviral Drugs, Journal of Infectious Diseases, 2007, pp. 665-674, vol. 195.
Schultz, Prodrugs of Biologically Active Phosphate Esters, Bioorganic & Medicinal Chemistry, 2003, pp. 885-898, vol. 11.
Scott, et al., Interferon-a-2b Plus Ribavirin: A Review of its Use in the Management of Chronic Hepatitis C, Drugs, 2002, pp. 507-556, vol. 62, No. 3.
Shekunov, et al., Crystallization processes in pharmaceutical technology and drug delivery design, Journal of Crystal Growth, 2000, pp. 122-136, vol. 211.
Siegel, Discovery and Synthesis of a Phosphoramidate Prodrug of a Pyrrolo[2,1-f][triazin-4-amino] Adenine C-Nucleoside(GS-5734) for the Treatment of Ebola and Emerging Viruses, J. Med. Chem., Jan. 26 2017, 51 pages.
Silverman et al., The Organic Chemistry of Drug Design and Drug Action, 1992, pp. 19-23.
Silverman, The Organic Chemistry of Drug Design and Drug Action, 2nd Ed., 2004, pp. 29-34.
Srivastav, et al., Antiviral Activity of Various 1-(2'-Deoxy-β-D-lyxofuranosyl), 1-(2'-Fluoro-β-D-xylofuranosyl), 1-(3'-Fluor-β -D-arabinofuranosyl), and 2'-Fluoro-2',3'-didehydro-2',3'-dideoxyribose Pyrimidine Nucleoside Analogues against Duck Hepatitis B Virus (DHBV) and Human Hepatitis B Virus (HBV) Replication, Journal of Medicinal Chemistry, 2010, pp. 7156-7166, vol. 53, No. 19.
Taiwan Patent Office, Office Action with Search Report for TW Patent Application No. 099131868, dated May 22, 2014.
Taiwan Patent Office, Office Action with Search Report for TW Patent Application No. 102115415, dated May 15, 2014.
Tapia, et al., Combination of a Mutagenic Agent with a Reverse Transcriptase Inhibitor Results n Systematic Inhibition of HIV-1 Infection, Virology, 2005, pp. 1-8, vol. 338.
Uchiyama, et al., O-selective Phosphorylation of Nucleosides without N-protection, J. Org. Chem., Jan. 1, 1993, vol. 58, No. 2.
Ukraine Patent Office, Second Office Action for UA Patent Application No. 2011 10568, dated Aug. 11, 2014.
United States Patent and Trademark Office, Final Rejection for U.S. Appl. No. 12/886,248, dated Aug. 21, 2014.
United States Patent and Trademark Office, Notice of Allowance for U.S. Appl. No. 13/649,511, dated Feb. 13, 2014.
United States Patent and Trademark Office, Notice of Allowance for U.S. Appl. No. 13/649,511, dated Jun. 3, 2014.
United States Patent and Trademark Office, Notice of Allowance for U.S. Appl. No. 12/428,176, dated Apr. 12, 2011.
United States Patent and Trademark Office, Notice of Allowance for U.S. Appl. No. 12/428,176, dated Jan. 6, 2011.
United States Patent and Trademark Office, Notice of Allowance for U.S. Appl. No. 12/428,234, dated Apr. 7, 2011.
United States Patent and Trademark Office, Notice of Allowance for U.S. Appl. No. 12/702,957, dated Apr. 26, 2011.
United States Patent and Trademark Office, Notice of Allowance for U.S. Appl. No. 12/885,917, dated Feb. 17, 2011.
United States Patent and Trademark Office, Notice of Allowance for U.S. Appl. No. 13/050,820, dated Jan. 31, 2013.
United States Patent and Trademark Office, Notice of Allowance for U.S. Appl. No. 13/117,060, dated Aug. 10, 2012.
United States Patent and Trademark Office, Notice of Allowance for U.S. Appl. No. 13/117,060, dated Nov. 28, 2012.
United States Patent and Trademark Office, Notice of Allowance for U.S. Appl. No. 13/196,117, dated Jul. 16, 2012.
United States Patent and Trademark Office, Notice of Allowance for U.S. Appl. No. 13/196,117, dated Mar. 27, 2012.
United States Patent and Trademark Office, Office Action (Restriction Requirement) for U.S. Appl. No. 12/886,248, dated Sep. 14, 2012.
United States Patent and Trademark Office, Office Action for U.S. Appl. No. 14/613,719, dated Jul. 21, 2016.
United States Patent and Trademark Office, Office Action for U.S. Appl. No. 14/613,719, dated Nov. 4, 2016.
United States Patent and Trademark Office, Office Action for U.S. Appl. No. 12/428,234, dated Dec. 23, 2010.
United States Patent and Trademark Office, Office Action for U.S. Appl. No. 12/702,957, dated Dec. 23, 2010.
United States Patent and Trademark Office, Office Action for U.S. Appl. No. 12/886,248, dated Mar. 4, 2013.
United States Patent and Trademark Office, Office Action for U.S. Appl. No. 12/886,248, dated Nov. 6, 2012.

(56) References Cited

OTHER PUBLICATIONS

United States Patent and Trademark Office, Office Action for U.S. Appl. No. 13/050,820, dated Mar. 27, 2012.
United States Patent and Trademark Office, Office Action for U.S. Appl. No. 13/050,820, dated Oct. 16, 2012.
United States Patent and Trademark Office, Office Action for U.S. Appl. No. 13/196,117 dated Sep. 23, 2011.
United States Patent and Trademark Office, Office Action for U.S. Appl. No. 13/649,511, dated Aug. 15, 2013.
United States Patent and Trademark Office, Office Action for U.S. Appl. No. 13/649,511, dated Jan. 22, 2013.
United States Patent and Trademark Office, Office Action for U.S. Appl. No. 13/813,886, dated Sep. 24, 2014.
United States Patent and Trademark Office, Pre-Appeal Brief for U.S. Appl. No. 14/613,719, Feb. 6, 2017.
United States Patent and Trademark Office, Pre-Appeal Decision for U.S. Appl. No. 14/613,719, Mar. 14, 2017.
Vaghefi, et al., Synthesis and Antiviral Activity of Certain Nucleoside 5'-Phosphonoformate Derivatives, Journal of Medicinal Chemistry, 1986, pp. 1389-1393, vol. 29, No. 8.
Vietnam Patent Office, Second Examination Report for VN Patent Application No. 1-2010-02939, dated Jul. 26, 2012.
Warren, et al., Therapeutic efficacy of the small molecule GS-5734 against Ebola virus in rhesus monkeys, Nature, 2016, pp. 381-385, vol. 531.
Wu, et al., Synthetic Methodologies for C-Nucleosides, Synthesis, 2004, pp. 1533-1553, vol. 10.
Yamanaka, et al., Metabolic Studies on BMS-200475, a New Antiviral Compound Active against Hepatitis B Virus, Antimicrobial Agents and Chemotherapy, 1999, p. 190, vol. 43, No. 1.
Zhang, et al., A Practical Synthesis of (2R)-3,5-di-O-benzoyl-2-fluoro-2-C-methyl-D-ribono-y-lactone, Tetrahedron: Asymmetry, 2009, pp. 305-312, vol. 20.
Bojack, G. et al., Design and Synthesis of Inhibitors of Adenosine and AMP Deaminases, Organic Letters, 2001, pp. 839-842, vol. 3, No. 6.
Dudfield, P. et al., Synthesis of C- ribosyl imidazo[2,1-f][1,2,4]triazines as inhibitors of adenosine and AMP deaminases, J. Chem. Soc, Perkin Trans I, 1999, pp. 2929-2936.
Greene, et al., Protective Groups in Organic Synthesis, 1991, pp. 118-142, John Wiley & Sons.
Haraguchi, K. et al., Stereoselective Synthesis of 1'-C-Branched Uracil Nucleosides From Uridine, Nucleosides & Nucleotides, 1995, pp. 417-420, vol. 14, No. 3-5.
Hayashi, M. et al., C-Nucleosides, A Synthesis of 2-Substituted 7-(b-D-Ribofuranosyl)-Pyrrolo[2,1-f]-1,2,4-Triazines. A New Type of "Purine Like" C-Nucleoside, Heterocycles, 1992, pp. 569-574, vol. 34, No. 3.
Hoffman, When, in the Context of Drug Design, Can a Fluorine Atom Successfully Substitute a Hydroxyl Group? International Journal of Quantum Chemistry, 2002, pp. 419-427, vol. 89.
European Patent Office, International Search Report for International Patent Application No. PCT/US2010/049508, dated Nov. 5, 2010.
Itoh, Y. et al., Divergent and Stereocontrolled Approach to the Synthesis of Uracil Nucleosides Branched at the Anomeric Position, J. Org. Chem, 1995, pp. 656-662, vol. 60.
Knutsen, L. et al., Synthesis of Imidazo-fused Bridgehead-nitrogen C -Nucleosides via Dehydrative Coupling Reactions of 2,5-Anhydro-3,4,6-tri-O-benzoyl-D-allonic Acid, J. Chem. Soc. Perkin Trans I, 1984, pp. 229-238.
Knutsen, L. et al., Synthesis of Imidazo-fused Bridgehead-nitrogen C -Nucleosides : Coupling-Elimination Reactions of 2,5-Anhydro-3,4,6-tri-O-benzoyl-D- allonic Acid, J. Chem. Soc. Perkin Trans I, 1985, pp. 621-630.
Nishimura, N., Synthesis of pyrrolo[2,1-f][1,2,4]triazine C-nucleosides. Isosteres of sangivamycin, tubercidin, and toyocamycin, Carbohydrate Research, 2001, pp. 77-82, vol. 331.
Otter, B. et al., Conformational Properties of Purine-Like C-Nucleosides, Nucleosides & Nucleotides, 1996, pp. 793-807, vol. 15, No. 1-3.

Patil, S. et al., 4-Aza-7,9-Dideazaadenosine, a New Cytotoxic Synthetic C-Nucleoside Analogue of Adenosine, Tetrahedron Letters, 1994, pp. 5339-5342, vol. 35, No. 30.
European Patent Office, Written Opinion for PCT International Patent Application No. PCT/US2010/049508, dated Nov. 5, 2010.
Yoshimura, Y. et al., Synthesis and Biological Evaluation of 1'-C-Cyano-Pyrimidine Nucleosides, Nucleosides & Nucleotides, 1996, pp. 305-324, vol. 15, No. 1-3.
Harcort, et al., Molecular Characterization of the Polymerase Gene and Genomic Termini of Nipah Virus, Virology, 2001, pp. 192-201, vol. 287.
McGuigan, et al., Aryl Phosphoramidate Derivatives of d4T Have Improved Anti-HIV Efficacy in Tissue Culture and May Act by the Generation of a Novel Intracellular Metabolite, J. Med. Chem., 1996, pp. 1748-1753, vol. 39.
Mehellou, et. al., Aryloxy Phosphoramidate Triesters: a Technology for Delivering Monophosphorylated Nucleosides and Sugarsinto Cells, ChemMedChem, 2009, pp. 1779-1791, vol. 4.
Peterson, et al., Prodrug approaches to improving the oral absorption of antiviral nucleotide analogues, Expert opinion, Drug Deliv., 2009, pp. 405-420, vol. 6, No. 4.
Murakami, et al., Mechanism of Activation of PSI-7851 and Its Diastereoisomer PSI-7977, The Journal of Biological Chemistry, Nov. 5, 2010, pp. 34337-34347, vol. 285, No. 45.
China First Request for Invalidation to China Patent Application No. 201180035776.1, filed Jun. 1, 2020, 57 pages.
China Second Request for Invalidation to China Patent Application No. 201180035776.1, filed Jun. 11, 2020, 28 pages.
India Opposition Notice to India Patent Patent Application No. 1328/CHENP/2013 (India Patent No. 319927), filed Jun. 30, 2020, 259 pages (part 1, pp. 1-129).
India Opposition Notice to India Patent Patent Application No. 1328/CHENP/2013 (India Patent No. 319927), filed Jun. 30, 2020, 259 pages (part 2, pp. 130-259).
India Notice of Post-Grant Opposition in India Patent Application No. 201727012821 (India Patent No. 332280, filed Jun. 30, 2020, 639 pages.
Pakistan Notice of Opposition to the Grant of Patent on Pakistan Application No. 684/2015 (Pakistan Patent No. 143378), dated Aug. 5, 2020, 9 pages.
Taiwan Cancellation Brief and Exhibits to Taiwan Patent No. I687432, dated Jul. 17, 2020, 536 pp. (part 1, pp. 1-233).
Taiwan Cancellation Brief and Exhibits to Taiwan Patent No. I687432, dated Jul. 17, 2020, 536 pp. (part 2, pp. 234-536).
Brittain, 2016. Polymorphism in pharmaceutical solids. [Book].
Franchetti et al., Antitumor Activity of C-Methyl-β-D-ribofuranosyladenine Nuceoside Ribonuceotide Reductase Inhibitors, J. Med. Chem. 2005, pp. 4983-4989, vol. 48.
Lo et al., GS-5734 and its parent nucleoside analog inhibit Filo-, Pneumo-, and Paramyxoviruses, Scientific Reports, 2017, 7 (43395), pp. 1-7 + Supplementary Material.
Ross et al., Synthesis of Diastereomerically Pure Nucleotide and Phosphoramidates, J. Org. Chem., 2011, pp. 8311-8319, vol. 76.
Towner et al., Newly Discovered Ebola Virus Associated with Hemorrhagic Fever Outbreak in Uganda, PLoS Pathogens, 2008, 6 pages, vol. 4, Issue 11.
Brazil Patent Office, Third Party submission for BR 11 2013 001267-6, dated Jan. 15, 2019.
Chinese Patent Office, First Office Action for CN Patent Application No. 201080011690.0, dated Jun. 8, 2013.
European Patent Office, International Preliminary Report on Patentability for PCT International Application No. PCT/US2015/057934, dated May 2, 2017, 14 pages.
European Patent Office, International Preliminary Report on Patentability for PCT International Application No. PCT/US2018/022166, dated Sep. 17, 2019, 7 pages.
European Patent Office, International Search Report and Written Opinion for PCT International Application No. PCT/US2018/022166, dated Jun. 11, 2018, 18 pages.
European Patent Office, International Search Report and Written Opinion for PCT International Application No. PCT/US2017/028251, dated Nov. 16, 2017, 22 pages.

(56) References Cited

OTHER PUBLICATIONS

European Patent Office, Written Opinion and ISR for PCT International Application No. PCT/US2015/057932, dated Apr. 15, 2016, 17 pages.
European Patent Office, Written Opinion and ISR for PCT International Application No. PCT/US2015/057934, dated Mar. 18, 2016, 20 pages.

PROCESSES AND INTERMEDIATES FOR THE PREPARATION OF 1'-SUBSTITUTED CARBA-NUCLEOSIDE ANALOGS

This application is a Continuation of U.S. patent application Ser. No. 12/886,248, filed on Sep. 20, 2010, claiming the benefit under 35 U.S.C. 119(e) of U.S. provisional application 61/244,299 filed Sep. 21, 2009 which is herein incorporated by reference in its entirety for all purposes.

FIELD OF THE INVENTION

The invention relates generally to methods and intermediates for preparing compounds with antiviral activity, more particularly methods and intermediates for preparing nucleosides active against Flaviviridae infections.

BACKGROUND OF THE INVENTION

Viruses comprising the Flaviviridae family comprise at least three distinguishable genera including *pestiviruses, flaviviruses*, and *hepaciviruses* (Calisher, et al., J. Gen. Virol., 1993, 70, 37-43). While pestiviruses cause many economically important animal diseases such as bovine viral diarrhea virus (BVDV), classical swine fever virus (CSFV, hog cholera) and border disease of sheep (BDV), their importance in human disease is less well characterized (Moennig, V., et al., Adv. Vir. Res. 1992, 48, 53-98). *Flaviviruses* are responsible for important human diseases such as dengue fever and yellow fever while *hepaciviruses* cause hepatitis C virus infections in humans. Other important viral infections caused by the Flaviviridae family include West Nile virus (WNV) Japanese encephalitis virus (JEV), tick-borne encephalitis virus, Junjin virus, Murray Valley encephalitis, St Louis enchaplitis, Omsk hemorrhagic fever virus and Zika virus. Combined, infections from the Flaviviridae virus family cause significant mortality, morbidity and economic losses throughout the world. Therefore, there is a need to develop effective treatments for Flaviviridae virus infections.

The hepatitis C virus (HCV) is the leading cause of chronic liver disease worldwide (Boyer, N. et al. J Hepatol. 32:98-112, 2000) so a significant focus of current antiviral research is directed toward the development of improved methods of treatment of chronic HCV infections in humans (Di Besceglie, A. M. and Bacon, B. R., Scientific American, October: 80-85, (1999); Gordon, C. P., et al., *J. Med. Chem.* 2005, 48, 1-20; Maradpour, D.; et al., *Nat. Rev. Micro.* 2007, 5(6), 453-463). A number of HCV treatments are reviewed by Bymock et al. in Antiviral Chemistry & Chemotherapy, 11:2; 79-95 (2000).

RNA-dependent RNA polymerase (RdRp) is one of the best studied targets for the development of novel HCV therapeutic agents. The NS5B polymerase is a target for inhibitors in early human clinical trials (Sommadossi, J., WO 01/90121 A2, US 2004/0006002 A1). These enzymes have been extensively characterized at the biochemical and structural level, with screening assays for identifying selective inhibitors (De Clercq, E. (2001) J. Pharmacol. Exp. Ther. 297:1-10; De Clercq, E. (2001) J. Clin. Virol. 22:73-89). Biochemical targets such as NS5B are important in developing HCV therapies since HCV does not replicate in the laboratory and there are difficulties in developing cell-based assays and preclinical animal systems.

Currently, there are primarily two antiviral compounds, ribavirin, a nucleoside analog, and interferon-alpha (α) (IFN), which are used for the treatment of chronic HCV infections in humans. Ribavirin alone is not effective in reducing viral RNA levels, has significant toxicity, and is known to induce anemia. The combination of IFN and ribavirin has been reported to be effective in the management of chronic hepatitis C (Scott, L. J., et al. *Drugs* 2002, 62, 507-556) but less than half the patients given this treatment show a persistent benefit. Other patent applications disclosing the use of nucleoside analogs to treat hepatitis C virus include WO 01/32153, WO 01/60315, WO 02/057425, WO 02/057287, WO 02/032920, WO 02/18404, WO 04/046331, WO2008/089105 and WO2008/141079 but additional treatments for HCV infections have not yet become available for patients. Therefore, drugs having improved antiviral and pharmacokinetic properties with enhanced activity against development of HCV resistance, improved oral bioavailability, greater efficacy, fewer undesirable side effects and extended effective half-life in vivo (De Francesco, R. et al. (2003) Antiviral Research 58:1-16) are urgently needed.

Certain ribosides of the nucleobases pyrrolo[1,2-f][1,2,4] triazine, imidazo[1,5-f][1,2,4]triazine, imidazo[1,2-f][1,2,4] triazine, and [1,2,4]triazolo[4,3-f][1,2,4]triazine have been disclosed in *Carbohydrate Research* 2001, 331(1), 77-82; *Nucleosides & Nucleotides* (1996), 15(1-3), 793-807; *Tetrahedron Letters* (1994), 35(30), 5339-42; *Heterocycles* (1992), 34(3), 569-74; *J. Chem. Soc. Perkin Trans.* 1 1985, 3, 621-30; *J. Chem. Soc. Perkin Trans.* 1 1984, 2, 229-38; WO 2000056734; *Organic Letters* (2001), 3(6), 839-842; *J Chem. Soc. Perkin Trans.* 1 1999, 20, 2929-2936; and *J. Med. Chem.* 1986, 29(11), 2231-5. However, these compounds have not been disclosed as useful for the treatment of HCV.

Ribosides of pyrrolo[1,2-f][1,2,4]triazinyl, imidazo[1,5-f][1,2,4]triazinyl, imidazo[1,2-f][1,2,4]triazinyl, and [1,2,4] triazolo[4,3-f][1,2,4]triazinyl nucleobases with antiviral, anti-HCV, and anti-RdRp activity have been disclosed by Babu, Y. S., WO2008/089105 and WO2008/141079; Cho, et al., WO2009/132123 and Francom, et al. WO2010/002877.

Butler, et al., WO2009/132135, has disclosed anti-viral pyrrolo[1,2-f][1,2,4]triazinyl, imidazo[1,5-f][1,2,4]triazinyl, imidazo[1,2-f][1,2,4]triazinyl, and [1,2,4]triazolo[4,3-f] [1,2,4]triazinyl nucleosides wherein the 1' position of the nucleoside sugar is substituted with a cyano group. However, the methods described for introducing the 1' cyano group only produced about a 3:1 ratio of β to α anomers and, in certain circumstances, the cyanation reactions was particularly slow. Therefore, there is a need to develop more efficient processes and intermediates for the syntheses of nucleosides of pyrrolo[1,2-f][1,2,4]triazinyl and imidazo[1, 2-f][1,2,4]triazinyl heterocycles.

SUMMARY OF THE INVENTION

Provided are processes and intermediates for the syntheses of nucleosides of pyrrolo[1,2-f][1,2,4]triazinyl and imidazo[1,2-f][1,2,4]triazinyl heterocycles.

Provided are methods for preparing a compound of Formula I:

[Formula I structure]

or an acceptable salt, thereof;
wherein:
$R^1$ is H, $(C_1\text{-}C_8)$alkyl, $(C_4\text{-}C_8)$carbocyclylalkyl, $(C_1\text{-}C_8)$ substituted alkyl, $(C_2\text{-}C_8)$alkenyl, $(C_2\text{-}C_8)$substituted alkenyl, $(C_2\text{-}C_8)$alkynyl, $(C_2\text{-}C_8)$substituted alkynyl, or aryl$(C_1\text{-}C_8)$alkyl;
each $R^{2a}$ or $R^{2b}$ is independently H, F or $OR^4$;
each $R^3$ is independently $(C_1\text{-}C_8)$ alkyl, $(C_1\text{-}C_8)$ substituted alkyl, $C_6\text{-}C_{20}$ aryl, $C_6\text{-}C_{20}$ substituted aryl, $C_2\text{-}C_{20}$ heterocyclyl, $C_2\text{-}C_{20}$ substituted heterocyclyl, $C_7\text{-}C_{20}$ arylalkyl, $C_7\text{-}C_{20}$ substituted arylalkyl, $(C_1\text{-}C_8)$ alkoxy, or $(C_1\text{-}C_8)$ substituted alkoxy;
each $R^4$ or $R^7$ is independently H, optionally substituted allyl, $-C(R^5)_2R^6$, $Si(R^3)_3$, $C(O)R^5$, $C(O)OR^5$, $-(C(R^5)_2)_m-R^{15}$ or

[fragment structure with $(CH_2)_m$];

or any two of $R^4$ or $R^7$ when taken together are $-C(R^{19})_2-$, $-C(O)-$ or $-Si(R^3)_2(X^2)_mSi(R^3)_2-$;
each $R^{15}$ is independently $-O-C(R^5)_2R^6$, $-Si(R^3)_3$, $C(O)OR^5$, $-OC(O)R^5$ or

[fragment structure with $(CH_2)_m$];

each $R^5$, $R^{18}$ or $R^{19}$ is independently H, $(C_1\text{-}C_8)$ alkyl, $(C_1\text{-}C_8)$ substituted alkyl, $(C_2\text{-}C_8)$alkenyl, $(C_2\text{-}C_8)$ substituted alkenyl, $(C_2\text{-}C_8)$ alkynyl, $(C_2\text{-}C_8)$ substituted alkynyl, $C_6\text{-}C_{20}$ aryl, $C_6\text{-}C_{20}$ substituted aryl, $C_2\text{-}C_{20}$ heterocyclyl, $C_2\text{-}C_{20}$ substituted heterocyclyl, $C_7\text{-}C_{20}$ arylalkyl or $C_7\text{-}C_{20}$ substituted arylalkyl;
each $R^6$ is independently $C_6\text{-}C_{20}$ aryl, $C_6\text{-}C_{20}$ substituted aryl, or optionally substituted heteroaryl;
each $R^a$ is independently H, $(C_1\text{-}C_8)$alkyl, $(C_2\text{-}C_8)$alkenyl, $(C_2\text{-}C_8)$alkynyl, aryl$(C_1\text{-}C_8)$alkyl, $(C_4\text{-}C_8)$carbocyclylalkyl, $-C(=O)R^{11}$, $-C(=O)OR^{11}$, $-C(=O)NR^{11}R^{12}$, $-C(=O)SR^{11}$, $-S(O)R^{11}$, $-S(O)_2R^{11}$, $-S(O)(OR^{11})$, $-S(O)_2(OR^{11})$, or $-SO_2NR^{11}R^{12}$;
$X^1$ is $C-R^{10}$ or N;
each $X^2$ is O or $CH_2$;
each m is 1 or 2;
each n is independently 0, 1 or 2;

each $R^8$ is halogen, $NR^{11}R^{12}$, $N(R^{11})OR^{11}$, $NR^{11}NR^{11}R^{12}$, $N_3$, NO, $NO_2$, CHO, $CH(=NR^{11})$, $-CH=NHNR^{11}$, $-CH=N(OR^{11})$, $-CH(OR^{11})_2$, $-C(=O)NR^{11}R^{12}$, $-C(=S)NR^{11}R^{12}$, $-C(=O)OR^{11}$, $(C_1\text{-}C_8)$alkyl, $(C_2\text{-}C_8)$alkenyl, $(C_2\text{-}C_8)$alkynyl, $(C_4\text{-}C_8)$carbocyclylalkyl, optionally substituted aryl, optionally substituted heteroaryl, $-C(=O)(C_1\text{-}C_8)$alkyl, $-S(O)_n(C_1\text{-}C_8)$alkyl, aryl$(C_1\text{-}C_8)$alkyl, CN, $OR^{11}$ or $SR_{11}$;
each $R^9$ or $R^{10}$ is independently H, halogen, $NR^{11}R^{12}$, $N(R^{11})OR^{11}$, $N(R^{11})N(R^{12})(R^{12})$, $N_3$, NO, $NO_2$, CHO, CN, $-CH(=NR^{11})$, $-CH=NNH(R^{11})$, $-CH=N(OR^{11})$, $-CH(OR^{11})_2$, $-C(=O)NR^{11}R^{12}$, $-C(=S)NR^{11}R^{12}$, $-C(=O)OR^{11}$, $R^{11}$, $OR^{11}$ or $SR^{11}$;
each $R^{11}$ or $R^{12}$ is independently H, $(C_1\text{-}C_8)$alkyl, $(C_2\text{-}C_8)$alkenyl, $(C_2\text{-}C_8)$alkynyl, $(C_3\text{-}C_8)$carbocyclyl, $(C_4\text{-}C_8)$ carbocyclylalkyl, optionally substituted aryl, optionally substituted heteroaryl, $-C(=O)(C_1\text{-}C_8)$alkyl, $-S(O)_n(C_1\text{-}C_8)$ alkyl, aryl$(C_1\text{-}C_8)$alkyl or $Si(R^3)_3$; or $R^{11}$ and $R^{12}$ taken together with a nitrogen to which they are both attached form a 3 to 7 membered heterocyclic ring wherein any one carbon atom of said heterocyclic ring can optionally be replaced with $-O-$, $-S(O)_n-$ or $-NR^a-$; or $R^{11}$ and $R^{12}$ taken together are $-Si(R^3)_2(X^2)_mSi(R^3)_2-$;
each $R^{20}$ is independently H, $(C_1\text{-}C_8)$alkyl, substituted $(C_1\text{-}C_8)$alkyl or halo;
wherein each $(C_1\text{-}C_8)$alkyl, $(C_2\text{-}C_8)$alkenyl, $(C_2\text{-}C_8)$alkynyl or aryl$(C_1\text{-}C_8)$alkyl of each $R^1$, $R^3$, $R^4$, $R^5$, $R^6$, $R^{18}$, $R^{19}$, $R^{20}$, $R^{11}$ or $R^{12}$ is, independently, optionally substituted with one or more halo, hydroxy, CN, $N_3$, $N(R^a)_2$ or $OR^a$; and wherein one or more of the non-terminal carbon atoms of each said $(C_1\text{-}C_8)$alkyl is optionally replaced with $-O-$, $-S(O)_n-$ or $-NR^a-$;
said method comprising:
(a) providing a compound of Formula II

[Formula II structure]

or an acceptable salt thereof;
wherein $R^{16}$ is OH, $OR^{18}$, $-OC(O)OR^{18}$ or $-OC(O)R^{18}$;
(b) treating the compound of Formula II with a cyanide reagent and a Lewis acid;
thereby forming the compound of Formula I;
provided that when the compound of Formula II is:

[structure with Bn, OBn groups]

wherein $X^1$ is CH or N, $R^1$ is $CH_3$, $R^8$ is $NH_2$, and $R^9$ is $NH_2$ or H or;

wherein $X^1$ is CH, $R^1$ is $CH_3$, $R^8$ is OH, and $R^9$ is $NH_2$ or;

wherein $X^1$ is CH, each $R^1$ and $R^9$ is H and $R^8$ is $NH_2$;

then said cyanide reagent is not $(CH_3)_3SiCN$ or said Lewis acid is not $BF_3$—$O(CH_2CH_3)_2$.

Also provided are compounds of Formula II that are useful intermediates for the preparation of compounds of Formula I. Provided are compounds of Formula II represented by Formula VI:

Formula VI

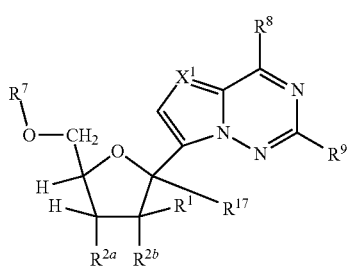

or an acceptable salt, thereof;
wherein:
$R^1$ is H, $(C_1-C_8)$alkyl, $(C_4-C_8)$carbocyclylalkyl, $(C_1-C_8)$ substituted alkyl, $(C_2-C_8)$alkenyl, $(C_2-C_8)$substituted alkenyl, $(C_2-C_8)$alkynyl, $(C_2-C_8)$substituted alkynyl, or aryl$(C_1-C_8)$alkyl;

each $R^{2a}$ or $R^{2b}$ is independently H, F or $OR^4$;

each $R^3$ is independently $(C_1-C_8)$ alkyl, $(C_1-C_8)$ substituted alkyl, $C_6-C_{20}$ aryl, $C_6-C_{20}$ substituted aryl, $C_2-C_{20}$ heterocyclyl, $C_2-C_{20}$ substituted heterocyclyl, $C_7-C_{20}$ arylalkyl, $C_7-C_{20}$ substituted arylalkyl, $(C_1-C_8)$ alkoxy, or $(C_1-C_8)$ substituted alkoxy;

each $R^4$ or $R^7$ is independently H, optionally substituted allyl, —$C(R^5)_2R^6$, $Si(R^3)_3$, $C(O)R^5$, $C(O)OR^5$, —$(C(R^5)_2)_m$—$R^{15}$ or

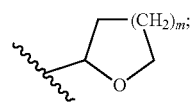

or any two of $R^4$ or $R^7$ when taken together are —$C(R^{19})_2$—, —$C(O)$— or —$Si(R^3)_2(X^2)_mSi(R^3)_2$—;

each $R^{15}$ is independently —O—$C(R^5)_2R^6$, —$Si(R^3)_3$, $C(O)OR^5$, —$OC(O)R^5$ or

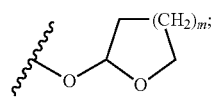

each $R^5$, $R^{18}$ or $R^{19}$ is independently H, $(C_1-C_8)$ alkyl, $(C_1-C_8)$ substituted alkyl, $(C_2-C_8)$alkenyl, $(C_2-C_8)$ substituted alkenyl, $(C_2-C_8)$ alkynyl, $(C_2-C_8)$ substituted alkynyl, $C_6-C_{20}$ aryl, $C_6-C_{20}$ substituted aryl, $C_2-C_{20}$ heterocyclyl, $C_2-C_{20}$ substituted heterocyclyl, $C_7-C_{20}$ arylalkyl, or $C_7-C_{20}$ substituted arylalkyl;

each $R^6$ is independently $C_6-C_{20}$ aryl, $C_6-C_{20}$ substituted aryl, or optionally substituted heteroaryl;

each $R^a$ is independently H, $(C_1-C_8)$alkyl, $(C_2-C_8)$alkenyl, $(C_2-C_8)$alkynyl, aryl$(C_1-C_8)$alkyl, $(C_4-C_8)$carbocyclylalkyl, —$C(=O)R^{11}$, —$C(=O)OR^{11}$, —$C(=O)NR^{11}R^{12}$, —$C(=O)SR^{11}$, —$S(O)R^{11}$, —$S(O)_2R^{11}$, —$S(O)(OR^{11})$, —$S(O)_2(OR^{11})$, or —$SO_2NR^{11}R^{12}$;

$X^1$ is C—$R^{10}$ or N;

each $X^2$ is O or $CH_2$;

each m is 1 or 2;

each n is independently 0, 1 or 2;

each $R^8$ is halogen, $NR^{11}R^{12}$, $N(R^{11})OR^{11}$, $NR^{11}NR^{11}R^{12}$, $N_3$, NO, $NO_2$, CHO, $CH(=NR^{11})$, —$CH=NHNR^{11}$, —$CH=N(OR^1)$, —$CH(OR^{11})_2$, —$C(=O)NR^{11}R^{12}$, —$C(=S)NR^{11}R^{12}$, —$C(=O)OR^1$, $(C_1-C_8)$alkyl, $(C_2-C_8)$alkenyl, $(C_2-C_8)$alkynyl, $(C_4-C_8)$carbocyclylalkyl, optionally substituted aryl, optionally substituted heteroaryl, —$C(=O)(C_1-C_8)$alkyl, —$S(O)_n(C_1-C_8)$alkyl, aryl$(C_1-C_8)$alkyl, CN, $OR^{11}$ or $SR^{11}$;

each $R^9$ or $R^{10}$ is independently H, halogen, $NR^{11}R^{12}$, $N(R^{11})OR$, $N(R^{11})N(R^{11})(R^{12})$, $N_3$, NO, $NO_2$, CHO, CN, —$CH(=NR^{11})$, —$CH=NNH(R^{11})$, —$CH=N(OR^{11})$, —$CH(OR^{11})_2$, —$C(=O)NR^{11}R^{12}$, —$C(=S)NR^{11}R^{12}$, —$C(=O)OR^{11}$, $R^{11}$, $OR^{11}$ or $SR^{11}$;

each $R^{11}$ or $R^{12}$ is independently H, $(C_1-C_8)$alkyl, $(C_2-C_8)$alkenyl, $(C_2-C_8)$alkynyl, $(C_3-C_8)$carbocyclyl, $(C_4-C_8)$ carbocyclylalkyl, optionally substituted aryl, optionally substituted heteroaryl, —$C(=O)(C_1-C_8)$alkyl, —$S(O)_n(C_1-C_8)$ alkyl, aryl$(C_1-C_8)$alkyl or $Si(R^3)_3$; or $R^{11}$ and $R^{12}$ taken together with a nitrogen to which they are both attached form a 3 to 7 membered heterocyclic ring wherein any one carbon atom of said heterocyclic ring can optionally be replaced with —O—, —$S(O)_n$— or —$NR^a$—; or $R^{11}$ and $R^{12}$ taken together are —$Si(R^3)_2(X^2)_mSi(R^3)_2$—; $R^{17}$ is OH, $OR^{18}$, —$OC(O)OR^{18}$ or —$OC(O)R^{18}$;

wherein each $(C_1-C_8)$alkyl, $(C_2-C_8)$alkenyl, $(C_2-C_8)$alkynyl or aryl$(C_1-C_8)$alkyl of each $R^1$, $R^3$, $R^4$, $R^5$, $R^6$, $R^{18}$, $R^{19}$, $R^{11}$ or $R^{12}$ is, independently, optionally substituted with one or more halo, hydroxy, CN, $N_3$, $N(R^a)_2$ or $OR^a$; and wherein one or more of the non-terminal carbon atoms of each said $(C_1-C_8)$alkyl is optionally replaced with —O—, —$S(O)_n$— or —$NR^a$—;

provided that when $R^{17}$ is OH or $OCH_3$, $R^1$ is H or $CH_3$ and each $R^{2a}$ and $R^{2b}$ is $OR^4$, then each $R^7$ and each $R^4$ is not H; and provided that the compound of Formula VI is not a compound of Formula VII Formula VII

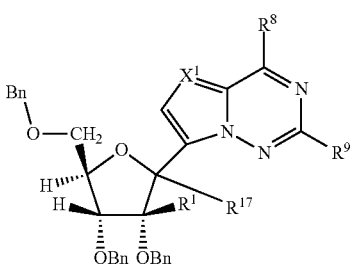

wherein $R^{17}$ is OH and
(a) $X^1$ is CH, $R^1$ is $CH_3$, $R^8$ is $NH_2$ and $R^9$ is $NH_2$ or H; or
(b) $X^1$ is CH, $R^1$ is $CH_3$, $R^8$ is OH and $R^9$ is $NH_2$; or
(c) $X^1$ is CH, each $R^1$ and $R^9$ is H and $R^8$ is $NH_2$; or
(d) $X^1$ is N, $R^1$ is $CH_3$, $R^8$ is $NH_2$, and $R^9$ is H, $NH_2$ or $SCH_3$;
(e) $X^1$ is N, $R^1$ is $CH_3$, $R^8$ is $SCH_3$ or $NHCH_3$, and $R^9$ is $SCH_3$; or (f) $X^1$ is N, $R^1$ is $CH_3$, $R^8$ is $OCH_3$, and $R^9$ is $SCH_3$, $SO_2CH_3$ or $NH_2$;

or wherein $R^{17}$ is $OCH_3$, $X^1$ is CH, each $R^1$ and $R^9$ is H and $R^8$ is $NH_2$.

DETAILED DESCRIPTION OF EXEMPLARY EMBODIMENTS

Reference will now be made in detail to certain embodiments of the invention, examples of which are illustrated in the accompanying description, structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention.

In one embodiment, provided is a method of preparing a compound of Formula I represented by a compound of Formula Ib Formula Ib or an acceptable salt, thereof, wherein the variables are defined as for Formula I;

said method comprising:

(a) providing a compound of Formula IIb

Formula IIb or an acceptable salt thereof;

wherein the variables are defined as for Formula II;

(b) treating the compound of Formula IIb with a cyanide reagent and a Lewis acid;

thereby forming the compound of Formula Ib;

provided that when the compound of Formula IIb is:

wherein $X^1$ is CH or N, $R^1$ is $CH_3$, $R^8$ is $NH_2$, and $R^9$ is $NH_2$ or H or;

wherein $X^1$ is CH, $R^1$ is $CH_3$, $R^8$ is OH, and $R^9$ is $NH_2$ or;

wherein $X^1$ is CH, each $R^1$ and $R^9$ is H and $R^8$ is $NH_2$;

then said cyanide reagent is not $(CH_3)_3SiCN$ or said Lewis acid is not $BF_3$—$O(CH_2CH_3)_2$.

In another embodiment of the method of preparing a compound of Formula Ib from a compound of Formula IIb, $R^{16}$ of Formula IIb is OH or $OR^{18}$. The following additional independent aspects of this embodiment are as follows:

(a) $R^1$ is H. $R^1$ is $CH_3$.

(b) $X^1$ is C—$R^{10}$. $X^1$ is C—H. $X^1$ is N.

(c) $R^8$ is $NR^{11}R^{12}$. $R^8$ is $OR^{11}$. $R^8$ is $SR^{11}$ (d) $R^9$ is H. $R^9$ is $NR^{11}R^{12}$. $R^9$ is $SR^{11}$ (e) $R^{2b}$ is $OR^4$. $R^{2b}$ is F. Each $R^{2a}$ and $R^{2b}$ is independently $OR^4$. $R^{2a}$ is $OR^4$ and $R^{2b}$ is F. $R^{2a}$ is $OR^4$, $R^{2b}$ is F and $R^4$ is $C(O)R^5$. $R^{2a}$ is $OR^4$, $R^{2b}$ is F and $R^4$ is $C(O)R^5$ wherein $R^5$ is phenyl or substituted phenyl. $R^{2b}$ is $OR^4$ wherein $R^4$ is $C(R^5)_2R^6$ and $R^6$ is phenyl or substituted phenyl. $R^{2b}$ is $OR^4$ wherein $R^4$ is $CH_2R^6$ and $R^6$ is phenyl. $R^{2b}$ is $OR^4$ wherein $R^4$ is $CH_2R^6$ and $R^6$ is substituted phenyl. Each $R^{2a}$ and $R^{2b}$ is OH. Each $R^{2a}$ and $R^{2b}$ is $OR^4$ wherein each $R^4$ is independently $C(R^5)_2R^6$ and $R^6$ is phenyl or substituted phenyl. Each $R^{2a}$ and $R^{2b}$ is $OR^4$ wherein each $R^4$ is $CH_2R^6$ and $R^6$ is phenyl. Each $R^{2a}$ and $R^{2b}$ is $OR^4$ wherein each $R^4$ is $CH_2R^6$ and each $R^6$ is independently substituted phenyl. Each $R^{2a}$ and $R^{2b}$ is $OR^4$ wherein the two $R^4$ taken together are —$C(R^{19})_2$—. Each $R^{2a}$ and $R^{2b}$ is $OR^4$ wherein the two $R^4$ taken together are —$C(CH_3)_2$—. Each $R^{2a}$ and $R^{2b}$ is $OR^4$ wherein the two $R^4$ taken together are —$CH(R^{19})$—. Each $R^{2a}$ and $R^{2b}$ is $OR^4$ wherein the two $R^4$ taken together are —$CH(R^{19})$— wherein $R^{19}$ is phenyl or substituted phenyl. $R^{2a}$ is $OR^4$ wherein $R^4$ is $C(R^5)_2R^6$, $R^6$ is phenyl or substituted phenyl and $R^{2b}$ is F. $R^{2a}$ is H.

(f) $R^7$ is $C(O)R^5$. $R^7$ is H. $R^7$ is $C(R^5)_2R^6$ and $R^6$ is phenyl or substituted phenyl. $R^7$ is $CH_2R^6$ and $R^6$ is phenyl. $R^7$ is $CH_2R^6$ and $R^6$ is substituted phenyl. $R^7$ is $C(R^5)_2R^6$ and each $R^5$ and $R^6$ is independently phenyl or substituted phenyl. $R^7$ is $Si(R^3)_3$. $R^7$ is $Si(R^3)_2$(t-butyl) wherein each $R^3$ is $CH_3$. $R^7$ is $Si(R^3)_2$(t-butyl) wherein each $R^3$ is independently phenyl or substituted phenyl. $R^7$ is tetrahydro-2H-pyran-2-yl. $R^7$ is $C(R^5)_2R^6$ wherein each $R^5$ and $R^6$ is independently phenyl or substituted phenyl and each $R^{2a}$ and $R^{2b}$ is $OR^4$ wherein the two $R^4$ taken together are —$C(CH_3)_2$—. $R^7$ is $Si(R^3)_3$ and each $R^{2a}$ and $R^{2b}$ is $OR^4$ wherein the two $R^4$ taken together are —$C(CH_3)_2$—. $R^7$ is $Si(R^3)_2$(t-butyl) wherein each $R^3$ is $CH_3$ and each $R^{2a}$ and $R^{2b}$ is $OR^4$ wherein the two $R^4$ taken together are —$C(CH_3)_2$—. $R^7$ is $Si(R^3)_2$(t-butyl) wherein each $R^3$ is independently phenyl or substituted phenyl and each $R^{2a}$ and $R^{2b}$ is $OR^4$ wherein the two $R^4$ taken together are —$C(CH_3)_2$—. $R^7$ is tetrahydro-2H-pyran-2-yl and each $R^{2a}$ and $R^{2b}$ is $OR^4$ wherein the two $R^4$ taken together are —$C(CH_3)_2$—. $R^7$ is $C(O)R^5$ and each $R^{2a}$ and $R^{2b}$ is $OR^4$ wherein the two $R^4$ taken together are —$C(CH_3)_2$—. $R^7$ is C($R^5$)$_2$$R^6$ wherein each $R^5$ and $R^6$ is independently phenyl or substituted phenyl and each $R^{2a}$ and $R^{2b}$ is O$R^4$ wherein the two $R^4$ taken together are —CH($R^{19}$)— wherein $R^{19}$ is phenyl or substituted phenyl. $R^7$ is Si($R^3$)$_3$ and each $R^{2a}$ and $R^{2b}$ is O$R^4$ wherein the two $R^4$ taken together are —CH($R^{19}$)— wherein $R^{19}$ is phenyl or substituted phenyl. $R^7$ is Si($R^3$)$_2$(t-butyl) wherein each $R^3$ is CH$_3$ and each $R^{2a}$ and $R^{2b}$ is O$R^4$ wherein the two $R^4$ taken together are —CH($R^{19}$)— wherein $R^{19}$ is phenyl or substituted phenyl. $R^7$ is Si($R^3$)$_2$(t-butyl) wherein each $R^3$ is independently phenyl or substituted phenyl and each $R^{2a}$ and $R^{2b}$ is O$R^4$ wherein the two $R^4$ taken together are —CH($R^{19}$)— wherein $R^{19}$ is phenyl or substituted phenyl. $R^7$ is tetrahydro-2H-pyran-2-yl and each $R^{2a}$ and $R^{2b}$ is O$R^4$ wherein the two $R^4$ taken together are —CH($R^{19}$)— wherein $R^{19}$ is phenyl or substituted phenyl. $R^7$ is C(O)$R^5$ and each $R^{2a}$ and $R^{2b}$ is O$R^4$ wherein the two $R^4$ taken together are —CH($R^{19}$)— wherein $R^{19}$ is phenyl or substituted phenyl. $R^7$ is C(O)$R^5$ wherein $R^5$ is phenyl or substituted phenyl and $R^{2b}$ is F. $R^7$ is H, each $R^{2a}$ and $R^{2b}$ is O$R^4$, each $R^4$ is H and $R^{16}$ is O$R^{18}$. $R^7$ is H, each $R^{2a}$ and $R^{2b}$ is O$R^4$, each $R^4$ is H and $R^{16}$ is O$R^{18}$ wherein $R^{18}$ is optionally substituted (C$_1$-C$_8$) alkyl.

(g) The cyanide reagent is ($R^3$)$_3$SiCN. The cyanide reagent is (CH$_3$)$_3$SiCN. The cyanide reagent is $R^5$C(O)CN. The cyanide reagent is $R^5$C(O)CN wherein $R^5$ is (C$_1$-C$_8$) alkoxy or (C$_1$-C$_8$) substituted alkoxy.

(h) The Lewis acid comprises boron. The Lewis acid comprises BF$_3$ or BCl$_3$. The Lewis acid is BF$_3$—O($R^{13}$)$_2$, BF$_3$—S($R^{13}$)$_2$, BCl$_3$—O($R^{13}$)$_2$ or BCl$_3$—S($R^{13}$)$_2$ wherein each $R^{13}$ is independently (C$_1$-C$_8$) alkyl, (C$_1$-C$_8$) substituted alkyl, (C$_2$-C$_8$)alkenyl, (C$_2$-C$_8$) substituted alkenyl, (C$_2$-C$_8$) alkynyl, (C$_2$-C$_8$) substituted alkynyl, C$_6$-C$_{20}$ aryl, C$_6$-C$_{20}$ substituted aryl, C$_2$-C$_{20}$ heterocyclyl, C$_2$-C$_{20}$ substituted heterocyclyl, C$_7$-C$_{20}$ arylalkyl, or C$_7$-C$_{20}$ substituted arylalkyl; wherein each (C$_1$-C$_8$)alkyl, (C$_2$-C$_8$)alkenyl, (C$_2$-C$_8$) alkynyl or aryl(C$_1$-C$_8$)alkyl of each $R^{13}$ is, independently, optionally substituted with one or more halogens and wherein one or more of the non-terminal carbon atoms of each said (C$_1$-C$_8$)alkyl is optionally replaced with —O— or —S(O)$_n$—; or two $R^{13}$ when taken together with the oxygen to which they are both attached form a 3 to 7 membered heterocyclic ring wherein one carbon atom of said heterocyclic ring can optionally be replaced with —O— or —S(O)$_n$ —. The Lewis acid is BF$_3$—O($R^{13}$)$_2$ and $R^{13}$ is (C$_1$-C$_8$) alkyl. The Lewis acid is ($R^{20}$)$_3$CS(O)$_2$OSi($R^3$)$_3$ wherein at least two $R^{20}$ are halo. The Lewis acid is ($R^{20}$)$_3$CS(O)$_2$OSi(CH$_3$)$_3$ wherein at least two $R^{20}$ are fluorine. The Lewis acid is trimethylsilyltriflate. The Lewis acid is a transition metal salt of ($R^{20}$)$_3$CS(O)$_2$OH wherein at least two $R^{20}$ are halo. The Lewis acid is a transition metal salt of ($R^{20}$)$_3$CS(O)$_2$OH wherein at least two $R^{20}$ are fluorine. The Lewis acid is a transition metal triflate. The Lewis acid is a lanthanide salt of ($R^{20}$)$_3$CS(O)$_2$OH wherein at least two $R^{20}$ are halo. The Lewis acid is a lanthanide salt of ($R^{20}$)$_3$CS(O)$_2$OH wherein at least two $R^{20}$ are fluorine. The Lewis acid is a lanthanide triflate. The Lewis acid is an alkaline earth metal salt of ($R^{20}$)$_3$CS(O)$_2$OH wherein at least two $R^{20}$ are halo. The Lewis acid is an alkaline earth metal salt of ($R^{20}$)$_3$CS(O)$_2$OH wherein at least two $R^{20}$ are fluorine. The Lewis acid is an alkaline earth metal triflate. The Lewis acid is a aluminum, gallium, indium, thallium, tin, lead or bismuth salt of ($R^{20}$)$_3$CS(O)$_2$OH wherein at least two $R^{20}$ are halo. The Lewis acid is a aluminum, gallium, indium, thallium, tin, lead or bismuth salt of ($R^{20}$)$_3$CS(O)$_2$OH wherein at least two $R^{20}$ are fluorine. The Lewis acid is a triflate of aluminum, gallium, indium, thallium, tin, lead or bismuth. The Lewis acid comprises a transition metal or salt thereof. The Lewis acid comprises titanium or a salt thereof. The Lewis acid comprises TiCl$_4$. The Lewis acid comprises a lanthanide or a salt thereof. The Lewis acid comprises scandium or a salt thereof. The Lewis acid comprises vanadium or a salt thereof. The Lewis acid comprises tin or a salt thereof. The Lewis acid comprises SnCl$_4$. The Lewis acid comprises zinc or a salt thereof. The Lewis acid comprises ZnCl$_2$. The Lewis acid comprises samarium or a salt thereof. The Lewis acid comprises nickel or a salt thereof. The Lewis acid comprises copper or a salt thereof. The Lewis acid comprises aluminum or a salt thereof. The Lewis acid comprises gold or a salt thereof.

In another embodiment of a method of preparing a compound of Formula Ib, $R^{16}$ of Formula IIb is —OC(O)$R^{18}$. The following are additional independent aspects of this embodiment:

(a) $R^1$ is H. $R^1$ is CH$_3$.

(b) $X^1$ is C—$R^{10}$. $X^1$ is C—H. $X^1$ is N.

(c) $R^8$ is N$R^{11}$$R^{12}$. $R^8$ is O$R^{11}$. $R^8$ is S$R^{11}$ (d) $R^9$ is H. $R^9$ is N$R^{11}$$R^{12}$. $R^9$ is S$R^{11}$ (e) $R^{2b}$ is O$R^4$. $R^{2b}$ is F. Each $R^{2a}$ and $R^{2b}$ is independently O$R^4$. $R^{2a}$ is O$R^4$ and $R^{2b}$ is F. $R^{2a}$ is O$R^4$, $R^{2b}$ is F and $R^4$ is C(O)$R^5$. $R^{2a}$ is O$R^4$, $R^{2b}$ is F and $R^4$ is C(O)$R^5$ wherein $R^5$ is phenyl or substituted phenyl. $R^{2b}$ is O$R^4$ wherein $R^4$ is C($R^5$)$_2$$R^6$ and $R^6$ is phenyl or substituted phenyl. $R^{2b}$ is O$R^4$ wherein $R^4$ is CH$_2$$R^6$ and $R^6$ is phenyl. $R^{2b}$ is O$R^4$ wherein $R^4$ is CH$_2$$R^6$ and $R^6$ is substituted phenyl. Each $R^{2a}$ and $R^{2b}$ is OH. Each $R^{2a}$ and $R^{2b}$ is O$R^4$ wherein each $R^4$ is independently C($R^5$)$_2$$R^6$ and $R^6$ is phenyl or substituted phenyl. Each $R^{2a}$ and $R^{2b}$ is O$R^4$ wherein each $R^4$ is CH$_2$$R^6$ and $R^6$ is phenyl. Each $R^{2a}$ and $R^{2b}$ is O$R^4$ wherein each $R^4$ is CH$_2$$R^6$ and each $R^6$ is independently substituted phenyl. Each $R^{2a}$ and $R^{2b}$ is O$R^4$ wherein the two $R^4$ taken together are —C($R^{19}$)$_2$—. Each $R^{2a}$ and $R^{2b}$ is O$R^4$ wherein the two $R^4$ taken together are —C(CH$_3$)$_2$—. Each $R^{2a}$ and $R^{2b}$ is O$R^4$ wherein the two $R^4$ taken together are —CH($R^{19}$)—. Each $R^{2a}$ and $R^{2b}$ is O$R^4$ wherein the two $R^4$ taken together are —CH($R^{19}$)— wherein $R^{19}$ is phenyl or substituted phenyl. $R^{2a}$ is O$R^4$ wherein $R^4$ is C($R^5$)$_2$$R^6$, $R^6$ is phenyl or substituted phenyl and $R^{2b}$ is F. $R^{2a}$ is H.

(f) $R^7$ is C(O)$R^5$. $R^7$ is H. $R^7$ is C($R^5$)$_2$$R^6$ and $R^6$ is phenyl or substituted phenyl. $R^7$ is CH$_2$$R^6$ and $R^6$ is phenyl. $R^7$ is CH$_2$$R^6$ and $R^6$ is substituted phenyl. $R^7$ is C($R^5$)$_2$$R^6$ and each $R^5$ and $R^6$ is independently phenyl or substituted phenyl. $R^7$ is Si($R^3$)$_3$. $R^7$ is Si($R^3$)$_2$(t-butyl) wherein each $R^3$ is CH$_3$. $R^7$ is Si($R^3$)$_2$(t-butyl) wherein each $R^3$ is independently phenyl or substituted phenyl. $R^7$ is tetrahydro-2H-pyran-2-yl. $R^7$ is C($R^5$)$_2$$R^6$ wherein each $R^5$ and $R^6$ is independently phenyl or substituted phenyl and each $R^{2a}$ and $R^{2b}$ is O$R^4$ wherein the two $R^4$ taken together are —C(CH$_3$)$_2$—. $R^7$ is Si($R^3$)$_3$ and each $R^{2a}$ and $R^{2b}$ is O$R^4$ wherein the two $R^4$ taken together are —C(CH$_3$)$_2$—. $R^7$ is Si($R^3$)$_2$(t-butyl) wherein each $R^3$ is CH$_3$ and each $R^{2a}$ and $R^{2b}$ is O$R^4$ wherein the two $R^4$ taken together are —C(CH$_3$)$_2$—. $R^7$ is Si($R^3$)$_2$(t-butyl) wherein each $R^3$ is independently phenyl or substituted phenyl and each $R^{2a}$ and $R^{2b}$ is O$R^4$ wherein the two $R^4$ taken together are —C(CH$_3$)$_2$—. $R^7$ is tetrahydro-2H-pyran-2-yl and each $R^{2a}$ and $R^{2b}$ is O$R^4$ wherein the two $R^4$ taken together are —C(CH$_3$)$_2$—. $R^7$ is C(O)$R^5$ and each $R^{2a}$ and $R^{2b}$ is O$R^4$ wherein the two $R^4$ taken together are —C(CH$_3$)$_2$—. $R^7$ is C($R^5$)$_2$$R^6$ wherein each $R^5$ and $R^6$ is independently phenyl or substituted phenyl and each $R^{2a}$ and $R^{2b}$ is O$R^4$ wherein the two $R^4$ taken together are —CH($R^{19}$)— wherein $R^{19}$ is phenyl or substituted phenyl. $R^7$ is Si($R^3$)$_3$ and each $R^{2a}$ and $R^{2b}$ is O$R^4$ wherein the two $R^4$ taken together are —CH($R^{19}$)— wherein $R^{19}$ is phenyl or substituted phenyl. $R^7$ is Si($R^3$)$_2$(t-butyl) wherein each $R^3$ is CH$_3$ and each $R^{2a}$ and $R^{2b}$ is $OR^4$ wherein the two $R^4$ taken together are —CH($R^{19}$)— wherein $R^{19}$ is phenyl or substituted phenyl. $R^7$ is $Si(R^3)_2$(t-butyl) wherein each $R^3$ is independently phenyl or substituted phenyl and each $R^{2a}$ and $R^{2b}$ is $OR^4$ wherein the two $R^4$ taken together are —CH($R^{19}$)— wherein $R^{19}$ is phenyl or substituted phenyl. $R^7$ is tetrahydro-2H-pyran-2-yl and each $R^{2a}$ and $R^{2b}$ is $OR^4$ wherein the two $R^4$ taken together are —CH($R^{19}$)— wherein $R^{19}$ is phenyl or substituted phenyl. $R^7$ is $C(O)R^5$ and each $R^{2a}$ and $R^{2b}$ is $OR^4$ wherein the two $R^4$ taken together are —CH($R^{19}$)— wherein $R^{19}$ is phenyl or substituted phenyl. $R^7$ is $C(O)R^5$ wherein $R^5$ is phenyl or substituted phenyl and $R^{2b}$ is F.

(g) The cyanide reagent is $(R^3)_3SiCN$. The cyanide reagent is $(CH_3)_3SiCN$. The cyanide reagent is $R^5C(O)CN$. The cyanide reagent is $R^5C(O)CN$ wherein $R^5$ is $(C_1$-$C_8)$ alkoxy or $(C_1$-$C_8)$ substituted alkoxy.

(h) The Lewis acid comprises boron. The Lewis acid comprises $BF_3$ or $BCl_3$. The Lewis acid is $BF_3$—$O(R^{13})_2$, $BF_3$—$S(R^{13})_2$, $BCl_3$—$O(R^{13})_2$ or $BCl_3$—$S(R^{13})_2$ wherein each $R^{13}$ is independently $(C_1$-$C_8)$ alkyl, $(C_1$-$C_8)$ substituted alkyl, $(C_2$-$C_8)$alkenyl, $(C_2$-$C_8)$ substituted alkenyl, $(C_2$-$C_8)$ alkynyl, $(C_2$-$C_8)$ substituted alkynyl, $C_6$-$C_{20}$ aryl, $C_6$-$C_{20}$ substituted aryl, $C_2$-$C_{20}$ heterocyclyl, $C_2$-$C_{20}$ substituted heterocyclyl, $C_7$-$C_{20}$ arylalkyl, or $C_7$-$C_{20}$ substituted arylalkyl; wherein each $(C_1$-$C_8)$alkyl, $(C_2$-$C_8)$alkenyl, $(C_2$-$C_8)$ alkynyl or aryl$(C_1$-$C_8)$alkyl of each $R^{13}$ is, independently, optionally substituted with one or more halogens and wherein one or more of the non-terminal carbon atoms of each said $(C_1$-$C_8)$alkyl is optionally replaced with —O— or —S(O)$_n$—; or two $R^{13}$ when taken together with the oxygen to which they are both attached form a 3 to 7 membered heterocyclic ring wherein one carbon atom of said heterocyclic ring can optionally be replaced with —O— or —S(O)$_n$—. The Lewis acid is $BF_3$—$O(R^{13})_2$ and $R^{13}$ is $(C_1$-$C_8)$ alkyl. The Lewis acid is $(R^{20})_3CS(O)_2OSi(R^3)_3$ wherein at least two $R^{20}$ are halo. The Lewis acid is $(R^{20})_3CS(O)_2OSi(CH_3)_3$ wherein at least two $R^{20}$ are fluorine. The Lewis acid is trimethylsilyltriflate. The Lewis acid is a transition metal triflate. The Lewis acid is a lanthanide triflate. The Lewis acid is an alkaline metal triflate. The Lewis acid is a triflate of aluminum, gallium, indium, thallium, tin, lead or bismuth. The Lewis acid comprises a transition metal or salt thereof. The Lewis acid comprises titanium or a salt thereof. The Lewis acid comprises $TiCl_4$. The Lewis acid comprises a lanthanide or a salt thereof. The Lewis acid comprises scandium or a salt thereof. The Lewis acid comprises vanadium or a salt thereof. The Lewis acid comprises tin or a salt thereof. The Lewis acid comprises $SnCl_4$. The Lewis acid comprises zinc or a salt thereof. The Lewis acid comprises $ZnCl_2$. The Lewis acid comprises samarium or a salt thereof. The Lewis acid comprises nickel or a salt thereof. The Lewis acid comprises copper or a salt thereof. The Lewis acid comprises aluminum or a salt thereof. The Lewis acid comprises gold or a salt thereof.

(i) $R^{18}$ is $(C_1$-$C_8)$alkyl or substituted $(C_1$-$C_8)$alkyl. $R^{18}$ is $(C_1$-$C_8)$alkyl. $R^{18}$ is methyl.

In another embodiment of the method of preparing a compound of Formula Ib, the compound of Formula Ib is represented by Formula Ic

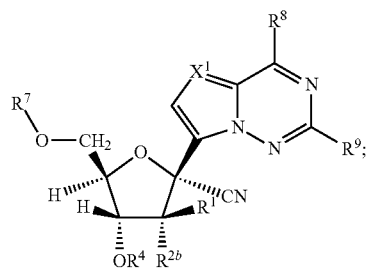

Formula Ic or a salt thereof; and the compound of Formula IIb is represented by Formula IIc

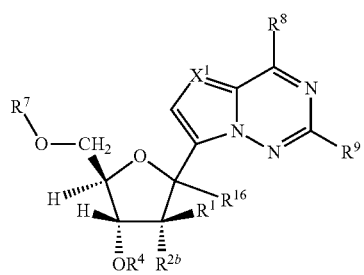

Formula IIc or a salt thereof;
wherein:
$R^{16}$ is OH or $OR^{18}$;
$R^{18}$ is optionally substituted $(C_1$-$C_8)$ alkyl;
the Lewis acid is $(R^{20})_3CS(O)_2OSi(R^3)_3$ or a metal salt of $(R^{20})_3CS(O)_2OH$;
at least two $R^{20}$ are halogen; and
said metal is selected from the group consisting aluminum, gallium, indium, thallium, tin, lead, bismuth, an alkaline earth metal, a transition metal and a lanthanide; and
the remaining variables are defined as for Formula IIb. The following are additional independent aspects of this embodiment:

(a) $R^1$ is H. $R^1$ is $CH_3$.
(b) $X^1$ is C—$R^{10}$. $X^1$ is C—H. $X^1$ is N.
(c) $R^8$ is $NR^{11}R^{12}$. $R^8$ is $OR^{11}$. $R^8$ is $SR^{11}$
(d) $R^9$ is H. $R^9$ is $NR^{11}R^{12}$. $R^9$ is $SR^{11}$.
(e) $R^{2b}$ is $OR^4$. $R^{2b}$ is F. $R^{2b}$ is F and $R^4$ is $C(O)R^5$. $R^{2b}$ is F and $R^4$ is $C(O)R^5$ wherein $R^5$ is phenyl or substituted phenyl. $R^{2b}$ is $OR^4$ wherein $R^4$ is $C(R^5)_2R^6$ and $R^6$ is phenyl or substituted phenyl. $R^{2b}$ is $OR^4$ wherein $R^4$ is $CH_2R^6$ and $R^6$ is phenyl. $R^{2b}$ is $OR^4$ wherein $R^4$ is $CH_2R^6$ and $R^6$ is substituted phenyl. Each $OR^4$ and $R^{2b}$ is OH. $R^{2b}$ is $OR^4$ wherein each $R^4$ is independently $C(R^5)_2R^6$ and $R^6$ is phenyl or substituted phenyl. $R^{2b}$ is $OR^4$ wherein each $R^4$ is $CH_2R^6$ and $R^6$ is phenyl. $R^{2b}$ is $OR^4$ wherein each $R^4$ is $CH_2R^6$ and each $R^6$ is independently substituted phenyl. $R^{2b}$ is $OR^4$ wherein the two $R^4$ taken together are —C($R^{19})_2$—. $R^{2b}$ is $OR^4$ wherein the two $R^4$ taken together are —C($CH_3)_2$—. $R^{2b}$ is $OR^4$ wherein the two $R^4$ taken together are —CH($R^{19}$)—. $R^{2b}$ is $OR^4$ wherein the two $R^4$ taken together are —CH($R^{19}$)— wherein $R^{19}$ is phenyl or substituted phenyl. $R^4$ is $C(R^5)_2R^6$, $R^6$ is phenyl or substituted phenyl and $R^{2b}$ is F.

(f) $R^7$ is $C(O)R^5$. $R^7$ is H. $R^7$ is $C(R^5)_2R^6$ and $R^6$ is phenyl or substituted phenyl. $R^7$ is $CH_2R^6$ and $R^6$ is phenyl. $R^7$ is $CH_2R^6$ and $R^6$ is substituted phenyl. $R^7$ is $C(R^5)_2R^6$ and each $R^5$ and $R^6$ is independently phenyl or substituted phenyl. $R^7$ is $Si(R^3)_3$. $R^7$ is $Si(R^3)_2$(t-butyl) wherein each $R^3$ is $CH_3$. $R^7$ is $Si(R^3)_2$(t-butyl) wherein each $R^3$ is independently phenyl or substituted phenyl. $R^7$ is tetrahydro-2H-pyran-2-yl. $R^7$ is $C(R^5)_2R^6$ wherein each $R^5$ and $R^6$ is independently phenyl or substituted phenyl and $R^{2b}$ is $OR^4$ wherein the two $R^4$ taken together are —$C(CH_3)_2$—. $R^7$ is $Si(R^3)_3$ and $R^{2b}$ is $OR^4$ wherein the two $R^4$ taken together are —$C(CH_3)_2$—. $R^7$ is $Si(R^3)_2$(t-butyl) wherein each $R^3$ is $CH_3$ and $R^{2b}$ is $OR^4$ wherein the two $R^4$ taken together are —$C(CH_3)_2$—. $R^7$ is $Si(R^3)_2$(t-butyl) wherein each $R^3$ is independently phenyl or substituted phenyl and $R^{2b}$ is $OR^4$ wherein the two $R^4$ taken together are —$C(CH_3)_2$—. $R^7$ is tetrahydro-2H-pyran-2-yl and $R^{2b}$ is $OR^4$ wherein the two $R^4$ taken together are —$C(CH_3)_2$—. $R^7$ is $C(O)R^5$ and $R^{2b}$ is $OR^4$ wherein the two $R^4$ taken together are —$C(CH_3)_2$—. $R^7$ is $C(R^5)_2R^6$ wherein each $R^5$ and $R^6$ is independently phenyl or substituted phenyl and $R^{2b}$ is $OR^4$ wherein the two $R^4$ taken together are —$CH(R^{19})$— wherein $R^{19}$ is phenyl or substituted phenyl. $R^7$ is $Si(R^3)_3$ and $R^{2b}$ is $OR^4$ wherein the two $R^4$ taken together are —$CH(R^{19})$— wherein $R^{19}$ is phenyl or substituted phenyl. $R^7$ is $Si(R^3)_2$(t-butyl) wherein each $R^3$ is $CH_3$ and $R^{2b}$ is $OR^4$ wherein the two $R^4$ taken together are —$CH(R^{19})$— wherein $R^{19}$ is phenyl or substituted phenyl. $R^7$ is $Si(R^3)_2$(t-butyl) wherein each $R^3$ is independently phenyl or substituted phenyl and $R^{2b}$ is $OR^4$ wherein the two $R^4$ taken together are —$CH(R^{19})$— wherein $R^{19}$ is phenyl or substituted phenyl. $R^7$ is tetrahydro-2H-pyran-2-yl and $R^{2b}$ is $OR^4$ wherein the two $R^4$ taken together are —$CH(R^{19})$— wherein $R^{19}$ is phenyl or substituted phenyl. $R^7$ is $C(O)R^5$ and $R^{2b}$ is $OR^4$ wherein the two $R^4$ taken together are —$CH(R^{19})$— wherein $R^{19}$ is phenyl or substituted phenyl. $R^7$ is $C(O)R^5$ wherein $R^5$ is phenyl or substituted phenyl and $R^{2b}$ is F. $R^7$ is H, $R^{2b}$ is $OR^4$, each $R^4$ is H and $R^{16}$ is $OR^{18}$. $R^7$ is H, $R^{2b}$ is $OR^4$, each $R^4$ is H and $R^{16}$ is $OR^{18}$ wherein $R^{18}$ is optionally substituted ($C_1$-$C_8$) alkyl.

(g) The cyanide reagent is $(R^3)_3SiCN$. The cyanide reagent is $(CH_3)_3SiCN$. The cyanide reagent is $R^5C(O)CN$. The cyanide reagent is $R^5C(O)CN$ wherein $R^5$ is ($C_1$-$C_8$) alkoxy or ($C_1$-$C_8$) substituted alkoxy.

(h) The Lewis acid is $(R^{20})_3CS(O)_2OSi(R^3)_3$ wherein at least two $R^{20}$ are halo. The Lewis acid is $(R^{20})_3CS(O)_2OSi(CH_3)_3$ wherein at least two $R^{20}$ are fluorine. The Lewis acid is trimethylsilyltriflate. The Lewis acid is a transition metal salt of $(R^{20})_3CS(O)_2OH$ wherein at least two $R^{20}$ are halo. The Lewis acid is a transition metal salt of $(R^{20})_3CS(O)_2OH$ wherein at least two $R^{20}$ are fluorine. The Lewis acid is a transition metal triflate. The Lewis acid is a lanthanide salt of $(R^{20})_3CS(O)_2OH$ wherein at least two $R^{20}$ are halo. The Lewis acid is a lanthanide salt of $(R^{20})_3CS(O)_2OH$ wherein at least two $R^{20}$ are fluorine. The Lewis acid is a lanthanide triflate. The Lewis acid is an alkaline earth metal salt of $(R^{20})_3CS(O)_2OH$ wherein at least two $R^{20}$ are halo. The Lewis acid is a alkaline earth metal salt of $(R^{20})_3CS(O)_2OH$ wherein at least two $R^{20}$ are fluorine. The Lewis acid is an alkaline earth metal triflate. The Lewis acid is a aluminum, gallium, indium, thallium, tin, lead or bismuth salt of $(R^{20})_3CS(O)_2OH$ wherein at least two $R^{20}$ are halo. The Lewis acid is a aluminum, gallium, indium, thallium, tin, lead or bismuth salt of $(R^{20})_3CS(O)_2OH$ wherein at least two $R^{20}$ are fluorine. The Lewis acid is a triflate of aluminum, gallium, indium, thallium, tin, lead or bismuth. The Lewis acid is a triflate of indium.

In another embodiment of the method of preparing a compound of Formula Ic from a compound of Formula IIc, each $X^1$ is CH and each $R^8$ is $NR^{11}R^{12}$. In another aspect of this embodiment, each $R^8$ is $NH_2$. In another aspect of this embodiment, each $R^9$ is H. In another aspect of this embodiment, each $R^8$ is $NH_2$ and each $R^9$ is H. In another aspect of this embodiment, the Lewis acid is $(R^{20})_3CS(O)_2OSi(CH_3)_3$ wherein at least two $R^{20}$ are fluorine. In another aspect of this embodiment, the Lewis acid is trimethylsilyl triflate. In another aspect of this embodiment, the Lewis acid is a transition metal triflate. In another aspect of this embodiment, the Lewis acid is a lanthanide triflate. In another aspect of this embodiment, the Lewis acid is an alkaline earth metal triflate. In another aspect of this embodiment, the Lewis acid is a triflate of aluminum, gallium, indium, thallium, tin, lead or bismuth. In another aspect of this embodiment, the Lewis acid is a triflate of indium. In another aspect of this embodiment, the cyanide reagent is $(R^3)_3SiCN$. In another aspect of this embodiment, the cyanide reagent is $(CH_3)_3SiCN$. In another aspect of this embodiment, the Lewis acid is $(R^{20})_3CS(O)_2OSi(CH_3)_3$ wherein at least two $R^{20}$ are fluorine and the cyanide reagent is $(R^3)_3SiCN$. In another aspect of this embodiment, the Lewis acid is trimethylsilyl triflate and the cyanide reagent is $(R^3)_3SiCN$. In another aspect of this embodiment, the Lewis acid is trimethylsilyl triflate and the cyanide reagent is $(CH_3)_3SiCN$. In another aspect of this embodiment, $R^7$ is $C(O)R^5$. In another aspect of this embodiment, $R^7$ is H. In another aspect of this embodiment, $R^7$ is $CH_2R^6$ and $R^6$ is phenyl or substituted phenyl. In another aspect of this embodiment, $R^7$ is $Si(R^3)_3$. In another aspect of this embodiment, $R^7$ is tetrahydro-2H-pyran-2-yl. In another aspect of this embodiment, $R^7$ is $Si(R^3)_3$ and $R^{2b}$ is $OR^4$ wherein the two $R^4$ taken together are —$C(CH_3)_2$—. In another aspect of this embodiment, $R^7$ is tetrahydro-2H-pyran-2-yl and $R^{2b}$ is $OR^4$ wherein the two $R^4$ taken together are —$C(CH_3)_2$—. In another aspect of this embodiment, $R^7$ is $C(O)R^5$ and $R^{2b}$ is $OR^4$ wherein the two $R^4$ taken together are —$C(CH_3)_2$—. In another aspect of this embodiment, $R^7$ is $C(O)R^5$ wherein $R^5$ is phenyl or substituted phenyl and $R^{2b}$ is F. In another aspect of this embodiment, $R^7$ is H, $R^{2b}$ is $OR^4$, each $R^4$ is H and $R^{16}$ is $OR^{18}$. In another aspect of this embodiment, $R^7$ is H, $R^{2b}$ is $OR^4$, each $R^4$ is H and $R^{16}$ is $OR^{18}$ wherein $R^{18}$ is optionally substituted ($C_1$-$C_8$) alkyl.

In another embodiment of the method of preparing a compound of Formula Ic from a compound of Formula IIc, each $X^1$ is CH, each $R^1$ is H or ($C_1$-$C_8$)alkyl, each $R^8$ is $NH_2$ and each $R^9$ is H. In another aspect of this embodiment, the Lewis acid is $(R^{20})_3CS(O)_2OSi(CH_3)_3$ wherein at least two $R^{20}$ are fluorine. In another aspect of this embodiment, the Lewis acid is trimethylsilyl triflate. In another aspect of this embodiment, the Lewis acid is a transition metal triflate. In another aspect of this embodiment, the Lewis acid is a lanthanide triflate. In another aspect of this embodiment, the Lewis acid is an alkaline earth metal triflate. In another aspect of this embodiment, the Lewis acid is a triflate of aluminum, gallium, indium, thallium, tin, lead or bismuth. In another aspect of this embodiment, the Lewis acid is a triflate of indium. In another aspect of this embodiment, the cyanide reagent is $(R^3)_3SiCN$. In another aspect of this embodiment, the cyanide reagent is $(CH_3)_3SiCN$. In another aspect of this embodiment, the Lewis acid is $(R^{20})_3CS(O)_2OSi(CH_3)_3$ wherein at least two $R^{20}$ are fluorine and the cyanide reagent is $(R^3)_3SiCN$. In another aspect of this embodiment, the Lewis acid is trimethylsilyl triflate and the cyanide reagent is $(R^3)_3SiCN$. In another aspect of this embodiment, the Lewis acid is trimethylsilyl triflate and the cyanide reagent is $(CH_3)_3SiCN$. In another aspect of this embodiment, $R^7$ is $C(O)R^5$. In another aspect of this embodiment, $R^7$ is H. In another aspect of this embodiment, $R^7$ is $CH_2R^6$ and $R^6$ is phenyl or substituted phenyl. In another aspect of this embodiment, $R^7$ is $Si(R^3)_3$. In another aspect of this embodiment, $R^7$ is tetrahydro-2H-pyran-2-yl. In another aspect of this embodiment, $R^7$ is $Si(R^3)_3$ and $R^{2b}$ is $OR^4$ wherein the two $R^4$ taken together are $—C(CH_3)_2—$. In another aspect of this embodiment, $R^7$ is tetrahydro-2H-pyran-2-yl and $R^{2b}$ is $OR^4$ wherein the two $R^4$ taken together are $—C(CH_3)_2—$. In another aspect of this embodiment, $R^7$ is $C(O)R^5$ and $R^{2b}$ is $OR^4$ wherein the two $R^4$ taken together are $—C(CH_3)_2—$. In another aspect of this embodiment, $R^7$ is $C(O)R^5$ wherein $R^5$ is phenyl or substituted phenyl and $R^{2b}$ is F. In another aspect of this embodiment, $R^7$ is H, $R^{2b}$ is $OR^4$, each $R^4$ is H and $R^{16}$ is $OR^{18}$. In another aspect of this embodiment, $R^7$ is H, $R^{2b}$ is $OR^4$, each $R^4$ is H and $R^{16}$ is $OR^{18}$ wherein $R^{18}$ is optionally substituted ($C_1$-$C_8$) alkyl.

Typically, the method of preparing compounds of Formula I, Ib or Ic from a compound of Formula II, IIb or IIc, respectively, are preformed in a suitable aprotic solvent at about −78 to 80° C. for about 10 minutes about 3 days. Non-limiting examples of suitable aprotic solvents include $CH_2Cl_2$, acetonitrile, $CH_2ClCH_2Cl$ or other halocarbon solvents. More typically, the method is performed at about −20 to about 65° C. for about 10 minutes to 4 hours. The mole ratio of the compound of Formula II, IIb or IIc to cyanide reagent is about 1:1 to 1:10, more typically about 1:2 to 1:6. The mole ratio of the compound of Formula II, IIb or IIc to Lewis acid is about 1:0.1 to about 1:10, more typically about 1:0.7 to about 1:6.

The conversion of the compounds of Formula II, IIb or IIc to a compound of Formula I, Ib or Ic, respectively, is promoted by Lewis acids. Many Lewis acids may promote this conversion including many that are commercially available. Non-limiting examples of Lewis acids comprising boron that are suitable for promoting this conversion are boron trifluoride etherates of methyl, ethyl, propyl, and butyl ethers; boron trifluoride-tert-butyl methyl etherate; boron trifluoride and boron trifluoride methyl sulfide complex. Non-limiting examples of Lewis acids comprising trialkylsilyl groups that are suitable for promoting this conversion are tri-($C_1$-$C_{12}$ alkyl)silyl-polyfluoro($C_1$-$C_{12}$)alkylsulfonates, trimethylsilyl polyfluoro($C_1$-$C_{12}$)alkylsulfonates, trimethylsilyl trifluoromethanesulfonate, tert-butyldimethylsilyl trifluoromethanesulfonate and triethylsilyl trifluoromethanesulfonate. Additional non-limiting examples of Lewis acids suitable for promoting this conversion are transition metal polyfluoro($C_1$-$C_{12}$)alkylsulfonates, lanthanide polyfluoro($C_1$-$C_{12}$)alkylsulfonates, alkaline earth metal polyfluoro($C_1$-$C_{12}$)alkylsulfonates, polyfluoro($C_1$-$C_{12}$)alkylsulfonates of aluminium, gallium, indium, thallium, tin, lead and bismuth, $TiCl_4$, $AlCl_3$, $ZnCl_2$, $ZnI_2$, $SnCl_4$, $InCl_3$, Sc(trifluoromethanesulfonate)$_3$, Sn(trifluoromethanesulfonate)$_2$, $InBr_3$, indium (trifluoromethanesulfonate)$_3$, $AuCl_3$, montmorilite clays, Cu(trifluoromethanesulfonate)$_2$, vanadyl trifluoromethanesulfonate, and salen complexes of Ti and Vn (Belokon, et al., Tetrahedron 2001, 771). In a preferred embodiment, the Lewis acid is trimethylsilyl trifluoromethanesulfonate. In another preferred embodiment, the Lewis acid is trimethylsilyl trifluoromethanesulfonate and the yield of the compound of Formula I, Ib or Ic is about 50% or greater. In another preferred embodiment, the Lewis acid is trimethylsilyl trifluoromethanesulfonate and the yield of the compound of Formula I, Ib or Ic is about 70% or greater. In another preferred embodiment, the Lewis acid is trimethylsilyl trifluoromethanesulfonate and the yield of the compound of Formula I, Ib or Ic is about 90% or greater. In another preferred embodiment, the Lewis acid is trimethylsilyl trifluoromethanesulfonate and the ratio of β to α anomer of the compound of formula I, Ib, or Ic is about 3.5 to 1 or greater. In another preferred embodiment, the Lewis acid is trimethylsilyl trifluoromethanesulfonate and the ratio of β to α anomer of the compound of Formula I, Ib, or Ic is about 4 to 1 or greater. In another preferred embodiment, the Lewis acid is trimethylsilyl trifluoromethanesulfonate and the ratio of β to α anomer of the compound of formula I, Ib, or Ic is about 5 to 1 or greater. In another preferred embodiment, the Lewis acid is trimethylsilyl trifluoromethanesulfonate and the ratio of β to α anomer of the compound of formula I, Ib, or Ic is about 6 to 1 or greater. In another preferred embodiment, the Lewis acid is trimethylsilyl trifluoromethanesulfonate and the ratio of β to α anomer of the compound of formula I, Ib, or Ic is about 8 to 1 or greater. In another preferred embodiment, the Lewis acid is trimethylsilyl trifluoromethanesulfonate and the ratio of β to α anomer of the compound of formula I, Ib, or Ic is about 10 to 1 or greater.

In another embodiment, provided is a method of preparing a compound of Formula II or IIb wherein $R^{16}$ is $—OC(O)R^{18}$, the method comprising:

(c) providing a compound of Formula II or IIb wherein $R^{16}$ is OH; and (d) treating the compound of Formula II or IIb wherein $R^{16}$ is OH with $YC(O)R^{18}$ wherein Y is selected from halogen, cyano, imidazol-1-yl; pyrazol-1-yl, $—O—C(O)R^{18}$ or $—O—C(O)OR^{18}$;

thereby forming a compound of Formula II or IIb wherein $R^{16}$ is $—OC(O)R^{18}$.

In another embodiment, the method of preparing the compound of Formula II or IIb wherein $R^{16}$ is $OC(O)R^{18}$ has the following additional independent aspects.

(a) $R^1$ is H. $R^1$ is $CH_3$.

(b) $X^1$ is $C—R^{10}$. $X^1$ is $C—H$. $X^1$ is N.

(c) $R^8$ is $NR^{11}R^{12}$. $R^8$ is $OR^{11}$. $R^8$ is $SR^{11}$ (d) $R^9$ is H. $R^9$ is $NR^{11}R^{12}$. $R^9$ is $SR^{11}$ (e) $R^{2b}$ is $OR^4$. $R^{2b}$ is F. Each $R^{2a}$ and $R^{2b}$ is independently $OR^4$. $R^{2a}$ is $OR^4$ and $R^{2b}$ is F. $R^{2a}$ is $OR^4$, $R^{2b}$ is F and $R^4$ is $C(O)R^5$. $R^{2a}$ is $OR^4$, $R^{2b}$ is F and $R^4$ is $C(O)R^5$ wherein $R^5$ is phenyl or substituted phenyl. $R^{2b}$ is $OR^4$ wherein $R^4$ is $C(R^5)_2R^6$ and $R^6$ is phenyl or substituted phenyl. $R^{2b}$ is $OR^4$ wherein $R^4$ is $CH_2R^6$ and $R^6$ is phenyl. $R^{2b}$ is $OR^4$ wherein $R^4$ is $CH_2R^6$ and $R^6$ is substituted phenyl. Each $R^{2a}$ and $R^{2b}$ is $OR^4$ wherein each $R^4$ is independently $C(R^5)_2R^6$ and $R^6$ is phenyl or substituted phenyl. Each $R^{2a}$ and $R^{2b}$ is $OR^4$ wherein each $R^4$ is $CH_2R^6$ and $R^6$ is phenyl. Each $R^{2a}$ and $R^{2b}$ is $OR^4$ wherein each $R^4$ is $CH_2R^6$ and each $R^6$ is independently substituted phenyl. Each $R^{2a}$ and $R^{2b}$ is $OR^4$ wherein the two $R^4$ taken together are $—C(R^{19})_2—$. Each $R^{2a}$ and $R^{2b}$ is $OR^4$ wherein the two $R^4$ taken together are $—C(CH_3)_2—$. Each $R^{2a}$ and $R^{2b}$ is $OR^4$ wherein the two $R^4$ taken together are $—CH(R^{19})—$. Each $R^{2a}$ and $R^{2b}$ is $OR^4$ wherein the two $R^4$ taken together are $—CH(R^{19})—$ wherein $R^{19}$ is phenyl or substituted phenyl. $R^{2a}$ is $OR^4$ wherein $R^4$ is $C(R^5)_2R^6$, $R^6$ is phenyl or substituted phenyl and $R^{2b}$ is F. $R^{2a}$ is H.

(f) $R^7$ is $C(O)R^5$. $R^7$ is $C(R^5)_2R^6$ and $R^6$ is phenyl or substituted phenyl. $R^7$ is $CH_2R^6$ and $R^6$ is phenyl. $R^7$ is $CH_2R^6$ and $R^6$ is substituted phenyl. $R^7$ is $C(R^5)_2R^6$ and each $R^5$ and $R^6$ is independently phenyl or substituted phenyl. $R^7$ is $Si(R^3)_3$. $R^7$ is $Si(R^3)_2$(t-butyl) wherein each $R^3$ is $CH_3$. $R^7$ is $Si(R^3)_2$(t-butyl) wherein each $R^3$ is independently phenyl or substituted phenyl. $R^7$ is tetrahydro-2H-pyran-2-yl. $R^7$ is $C(R^5)_2R^6$ wherein each $R^5$ and $R^6$ is independently phenyl or substituted phenyl and each $R^{2a}$ and $R^{2b}$ is $OR^4$ wherein the two $R^4$ taken together are $—C(CH_3)_2—$. $R^7$ is $Si(R^3)_3$ and each $R^{2a}$ and $R^{2b}$ is $OR^4$ wherein the two $R^4$ taken together are —C(CH$_3$)$_2$—. $R^7$ is Si(R$^3$)$_2$(t-butyl) wherein each $R^3$ is CH$_3$ and each $R^{2a}$ and $R^{2b}$ is $OR^4$ wherein the two $R^4$ taken together are —C(CH$_3$)$_2$—. $R^7$ is Si(R$^3$)$_2$(t-butyl) wherein each $R^3$ is independently phenyl or substituted phenyl and each $R^{2a}$ and $R^{2b}$ is $OR^4$ wherein the two $R^4$ taken together are —C(CH$_3$)$_2$—. $R^7$ is tetrahydro-2H-pyran-2-yl and each $R^{2a}$ and $R^{2b}$ is $OR^4$ wherein the two $R^4$ taken together are —C(CH$_3$)$_2$—. $R^7$ is C(O)R$^5$ and each $R^{2a}$ and $R^{2b}$ is $OR^4$ wherein the two $R^4$ taken together are —C(CH$_3$)$_2$—. $R^7$ is C(R$^5$)$_2$R$^6$ wherein each R$^5$ and R$^6$ is independently phenyl or substituted phenyl and each $R^{2a}$ and $R^{2b}$ is $OR^4$ wherein the two $R^4$ taken together are —CH(R$^{19}$)— wherein R$^{19}$ is phenyl or substituted phenyl. $R^7$ is Si(R$^3$)$_3$ and each $R^{2a}$ and $R^{2b}$ is $OR^4$ wherein the two $R^4$ taken together are —CH(R$^{19}$)— wherein R$^{19}$ is phenyl or substituted phenyl. $R^7$ is Si(R$^3$)$_2$(t-butyl) wherein each R$^3$ is CH$_3$ and each $R^{2a}$ and $R^{2b}$ is $OR^4$ wherein the two $R^4$ taken together are —CH(R$^{19}$)— wherein R$^{19}$ is phenyl or substituted phenyl. $R^7$ is Si(R$^3$)$_2$(t-butyl) wherein each R$^3$ is independently phenyl or substituted phenyl and each $R^{2a}$ and $R^{2b}$ is $OR^4$ wherein the two $R^4$ taken together are —CH(R$^{19}$)— wherein R$^{19}$ is phenyl or substituted phenyl. $R^7$ is tetrahydro-2H-pyran-2-yl and each $R^{2a}$ and $R^{2b}$ is $OR^4$ wherein the two $R^4$ taken together are —CH(R$^{19}$)— wherein R$^{19}$ is phenyl or substituted phenyl. $R^7$ is C(O)R$^5$ and each $R^{2a}$ and $R^{2b}$ is $OR^4$ wherein the two $R^4$ taken together are —CH(R$^{19}$)— wherein R$^{19}$ is phenyl or substituted phenyl. $R^7$ is C(O)R$^5$ wherein R$^5$ is phenyl or substituted phenyl and $R^{2b}$ is F.

(g) $R^{18}$ is (C$_1$-C$_8$)alkyl or substituted (C$_1$-C$_8$)alkyl. $R^{18}$ is (C$_1$-C$_8$)alkyl. $R^{18}$ is methyl.

In one embodiment, the mole ratio of the compound of Formula II, IIb or IIc wherein $R^{16}$ is OH to YC(O)R$^{18}$ is about 1:1 to about 1:10, preferably about 1:1 to about 1:6.5. Typically, the compound of Formula II, IIb or IIc wherein $R^{16}$ is OH is treated with YC(O)R$^{18}$ in an aprotic solvent such as, but not limited to, pyridine, THF or ether at about −30 to about 125° C. for about 30 minutes to about 24 hours. In one embodiment, Y is halogen. In another embodiment, Y is Cl. In another embodiment, Y is cyano. In another embodiment, Y is imidazol-1-yl. In another embodiment, Y is pyrazol-1-yl. In another embodiment, Y is —O—C(O)R$^{18}$. In another embodiment, Y is —O—C(O)OR$^{18}$. In a particular embodiment, $R^{18}$ is C$_1$-C$_6$ alkyl. In another particular embodiment, $R^{18}$ is CH$_3$. In another embodiment, $R^{18}$ is C$_1$-C$_6$ alkyl and Y is —O—C(O)R$^{18}$. In another embodiment, $R^{18}$ is CH$_3$ and Y—O—C(O)R$^{18}$.

The reaction of the compound of Formula II, IIb or IIc wherein $R^{16}$ is OH with YC(O)R$^{18}$ may be catalyzed or accelerated in the presence of a suitable base. Non-limiting examples of suitable bases include triethylamine, di-isopropylethylamine, pyridine, 4-dimethylaminopyridine, DBU, NaH and KH. The mole ratio of YC(O)R$^{18}$ to base is typically about 1:1 to 1:4.

In another embodiment, provided is a method of preparing a compound of Formula II wherein $R^{16}$ is OH,
the method comprising:
(e) providing a compound of Formula III:

Formula III (f) treating the compound of Formula III with an organometallic compound of Formula IV:

Formula IV wherein M is MgX$^3$ or Li and X$^3$ is halogen;

thereby forming a compound of Formula II wherein $R^{16}$ is OH;

provided that when M is Li, the compound of Formula II is not a compound of Formula VII Formula VII wherein $R^{17}$ is OH; and (a) $X^1$ is CH, $R^1$ is CH$_3$, $R^8$ is NH$_2$ and $R^9$ is NH$_2$ or H; or (b) $X^1$ is CH, $R^1$ is CH$_3$, $R^8$ is OH and $R^9$ is NH$_2$; or (c) $X^1$ is CH, each $R^1$ and $R^9$ is H and $R^8$ is NH$_2$; or (d) $X^1$ is N, $R^1$ is CH$_3$, $R^8$ is NH$_2$, and $R^9$ is H, NH$_2$ or SCH$_3$; or (e) $X^1$ is N, $R^1$ is CH$_3$, $R^8$ is SCH$_3$ or NHCH$_3$, and $R^9$ is SCH$_3$; or (f) $X^1$ is N, $R^1$ is CH$_3$, $R^8$ is OCH$_3$, and $R^9$ is SCH$_3$, SO$_2$CH$_3$ or NH$_2$.

In another embodiment of the method of preparing a compound of Formula II wherein $R^{16}$ is OH, the compound of Formula II is Formula IIb wherein $R^{16}$ is OH and the compound of Formula III is a compound of Formula IIIb:

Formula IIIb provided that when M is Li, the compound of Formula IIb is not a compound of Formula VII Formula VII

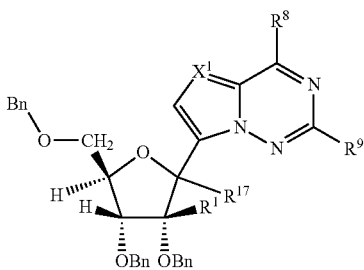

wherein $R^{17}$ is OH; and
(a) $X^1$ is CH, $R^1$ is $CH_3$, $R^8$ is $NH_2$ and $R^9$ is $NH_2$ or H; or
(b) $X^1$ is CH, $R^1$ is $CH_3$, $R^8$ is OH and $R^9$ is $NH_2$; or
(c) $X^1$ is CH, each $R^1$ and $R^9$ is H and $R^8$ is $NH_2$; or
(d) $X^1$ is N, $R^1$ is $CH_3$, $R^8$ is $NH_2$, and $R^9$ is H, $NH_2$ or $SCH_3$; or
(e) $X^1$ is N, $R^1$ is $CH_3$, $R^8$ is $SCH_3$ or $NHCH_3$, and $R^9$ is $SCH_3$; or
(f) $X^1$ is N, $R^1$ is $CH_3$, $R^8$ is $OCH_3$, and $R^9$ is $SCH_3$, $SO_2CH_3$ or $NH_2$.

The following are additional independent aspects of this embodiment:
(a) $R^1$ is H. $R^1$ is $CH_3$.
(b) $R^{2b}$ is $OR^4$. $R^{2b}$ is F. Each $R^{2a}$ and $R^{2b}$ is independently $OR^4$. $R^{2a}$ is $OR^4$ and $R^{2b}$ is F. $R^{2a}$ is $OR^4$, $R^{2b}$ is F and $R^4$ is $C(O)R^5$. $R^{2a}$ is $OR^4$, $R^{2b}$ is F and $R^4$ is $C(O)R^5$ wherein $R^5$ is phenyl or substituted phenyl. $R^{2b}$ is $OR^4$ wherein $R^4$ is $C(R^5)_2R^6$ and $R^6$ is phenyl or substituted phenyl. $R^{2b}$ is $OR^4$ wherein $R^4$ is $CH_2R^6$ and $R^6$ is phenyl. $R^{2b}$ is $OR^4$ wherein $R^4$ is $CH_2R^6$ and $R^6$ is substituted phenyl. Each $R^{2a}$ and $R^{2b}$ is OH. Each $R^{2a}$ and $R^{2b}$ is $OR^4$ wherein each $R^4$ is independently $C(R^5)_2R^6$ and $R^6$ is phenyl or substituted phenyl. Each $R^{2a}$ and $R^{2b}$ is $OR^4$ wherein each $R^4$ is $CH_2R^6$ and $R^6$ is phenyl. Each $R^{2a}$ and $R^{2b}$ is $OR^4$ wherein each $R^4$ is $CH_2R^6$ and each $R^6$ is independently substituted phenyl. Each $R^{2a}$ and $R^{2b}$ is $OR^4$ wherein the two $R^4$ taken together are —$C(R^{19})_2$—. Each $R^{2a}$ and $R^{2b}$ is $OR^4$ wherein the two $R^4$ taken together are —$C(CH_3)_2$—. Each $R^{2a}$ and $R^{2b}$ is $OR^4$ wherein the two $R^4$ taken together are —$CH(R^{19})$—. Each $R^{2a}$ and $R^{2b}$ is $OR^4$ wherein the two $R^4$ taken together are —$CH(R^{19})$— wherein $R^{19}$ is phenyl or substituted phenyl. $R^{2a}$ is $OR^4$ wherein $R^4$ is $C(R^5)_2R^6$, $R^6$ is phenyl or substituted phenyl and $R^{2b}$ is F. $R^{2a}$ is H.
(c) $R^7$ is $C(O)R^5$. $R^7$ is H. $R^7$ is $C(R^5)_2R^6$ and $R^6$ is phenyl or substituted phenyl. $R^7$ is $CH_2R^6$ and $R^6$ is phenyl. $R^7$ is $CH_2R^6$ and $R^6$ is substituted phenyl. $R^7$ is $C(R^5)_2R^6$ and each $R^5$ and $R^6$ is independently phenyl or substituted phenyl. $R^7$ is $Si(R^3)_3$. $R^7$ is $Si(R^3)_2$(t-butyl) wherein each $R^3$ is $CH_3$. $R^7$ is $Si(R^3)_2$(t-butyl) wherein each $R^3$ is independently phenyl or substituted phenyl. $R^7$ is tetrahydro-2H-pyran-2-yl. $R^7$ is $C(R^5)_2R^6$ wherein each $R^5$ and $R^6$ is independently phenyl or substituted phenyl and each $R^{2a}$ and $R^{2b}$ is $OR^4$ wherein the two $R^4$ taken together are —$C(CH_3)_2$—. $R^7$ is $Si(R^3)_3$ and each $R^{2a}$ and $R^{2b}$ is $OR^4$ wherein the two $R^4$ taken together are —$C(CH_3)_2$—. $R^7$ is $Si(R^3)_2$(t-butyl) wherein each $R^3$ is $CH_3$ and each $R^{2a}$ and $R^{2b}$ is $OR^4$ wherein the two $R^4$ taken together are —$C(CH_3)_2$—. $R^7$ is $Si(R^3)_2$(t-butyl) wherein each $R^3$ is independently phenyl or substituted phenyl and each $R^{2a}$ and $R^{2b}$ is $OR^4$ wherein the two $R^4$ taken together are —$C(CH_3)_2$—. $R^7$ is tetrahydro-2H-pyran-2-yl and each $R^{2a}$ and $R^{2b}$ is $OR^4$ wherein the two $R^4$ taken together are —$C(CH_3)_2$—. $R^7$ is $C(O)R^5$ and each $R^{2a}$ and $R^{2b}$ is $OR^4$ wherein the two $R^4$ taken together are —$C(CH_3)_2$—. $R^7$ is $C(R^5)_2R^6$ wherein each $R^5$ and $R^6$ is independently phenyl or substituted phenyl and each $R^{2a}$ and $R^{2b}$ is $OR^4$ wherein the two $R^4$ taken together are —$CH(R^{19})$— wherein $R^{19}$ is phenyl or substituted phenyl. $R^7$ is $Si(R^3)_3$ and each $R^{2a}$ and $R^{2b}$ is $OR^4$ wherein the two $R^4$ taken together are —$CH(R^{19})$— wherein $R^{19}$ is phenyl or substituted phenyl. $R^7$ is $Si(R^3)_2$(t-butyl) wherein each $R^3$ is $CH_3$ and each $R^{2a}$ and $R^{2b}$ is $OR^4$ wherein the two $R^4$ taken together are —$CH(R^{19})$— wherein $R^{19}$ is phenyl or substituted phenyl. $R^7$ is $Si(R^3)_2$(t-butyl) wherein each $R^3$ is independently phenyl or substituted phenyl and each $R^{2a}$ and $R^{2b}$ is $OR^4$ wherein the two $R^4$ taken together are —$CH(R^{19})$— wherein $R^{19}$ is phenyl or substituted phenyl. $R^7$ is tetrahydro-2H-pyran-2-yl and each $R^{2a}$ and $R^{2b}$ is $OR^4$ wherein the two $R^4$ taken together are —$CH(R^{19})$— wherein $R^{19}$ is phenyl or substituted phenyl. $R^7$ is $C(O)R^5$ and each $R^{2a}$ and $R^{2b}$ is $OR^4$ wherein the two $R^4$ taken together are —$CH(R^{19})$— wherein $R^{19}$ is phenyl or substituted phenyl. $R^7$ is $C(O)R^5$ wherein $R^5$ is phenyl or substituted phenyl and $R^{2b}$ is F.

(d) $X^1$ is C—$R^{10}$. $X^1$ is C—H. $X^1$ is N.
(e) $R^8$ is $NR^{11}R^{12}$. $R^8$ is $OR^{11}$. $R^8$ is $SR^1$.
(f) $R^9$ is H. $R^9$ is $NR^{11}R^{12}$. $R^9$ is $SR^{11}$.
(g) Each $R^{11}$ or $R^{12}$ is independently $(C_1-C_8)$alkyl, —$C(=O)(C_1-C_8)$alkyl, —$S(O)_n(C_1-C_8)$alkyl, aryl$(C_1-C_8)$alkyl or $Si(R^3)_3$; or $R^{11}$ and $R^{12}$ taken together with a nitrogen to which they are both attached form a 3 to 7 membered heterocyclic ring; or $R^{11}$ and $R^{12}$ taken together are —$Si(R^3)_2(X^2)_mSi(R^3)_2$—. Each $R^{11}$ or $R^{12}$ is independently $(C_1-C_8)$alkyl. Each $R^{11}$ or $R^{12}$ is independently $Si(R^3)_3$. Each $R^{11}$ or $R^{12}$ is independently $Si(R^3)_3$ wherein at least two of $R^3$ are $CH_3$ or phenyl. Each $R^{11}$ or $R^{12}$ is independently $Si(CH_3)_3$. Each $R^{11}$ and $R^{12}$ of $NR^{11}R^{12}$ is independently selected from $Si(R^3)_3$ or $R^{11}$ and $R^{12}$ of $NR^{11}R^{12}$ taken together are —$Si(R^3)_2(X^2)_mSi(R^3)_2$—. Each $R^{11}$ and $R^{12}$ of $NR^{11}R^{12}$ is independently selected from $Si(R^3)_3$ or $R^{11}$ and $R^{12}$ of $NR^{11}R^{12}$ taken together are —$Si(R^3)_2(X^2)_m Si(R^3)_2$—; and each $R^3$ is methyl.
(h) M is $MgX^3$. M is Li.

In another embodiment of the method of preparing a compound of Formula IIb wherein $R^{16}$ is OH, the compound of Formula IIb is Formula IIc and the compound of Formula IIIb is a compound of Formula IIIc:

Formula IIIc

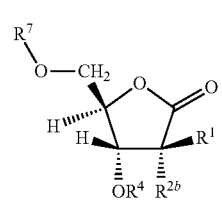

provided that when M is Li, the compound of Formula IIc is not a compound of Formula VII Formula VII

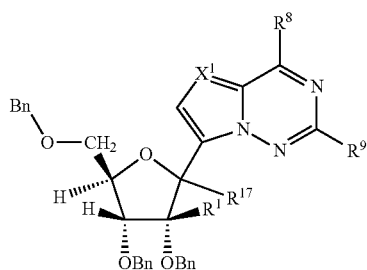

wherein R$^{17}$ is OH; and
(a) X$^1$ is CH, R$^1$ is CH$_3$, R$^8$ is NH$_2$ and R$^9$ is NH$_2$ or H; or
(b) X$^1$ is CH, R$^1$ is CH$_3$, R$^8$ is OH and R$^9$ is NH$_2$; or
(c) X$^1$ is CH, each R$^1$ and R$^9$ is H and R$^8$ is NH$_2$; or
(d) X$^1$ is N, R$^1$ is CH$_3$, R$^8$ is NH$_2$, and R$^9$ is H, NH$_2$ or SCH$_3$; or
(e) X$^1$ is N, R$^1$ is CH$_3$, R$^8$ is SCH$_3$ or NHCH$_3$, and R$^9$ is SCH$_3$; or
(f) X$^1$ is N, R$^1$ is CH$_3$, R$^8$ is OCH$_3$, and R$^9$ is SCH$_3$, SO$_2$CH$_3$ or NH$_2$.

The following are additional independent aspects of this embodiment:
(a) R$^1$ is H. R$^1$ is CH$_3$.
(b) R$^{2b}$ is OR$^4$. R$^{2b}$ is F. R$^{2b}$ is F and R$^4$ is C(O)R$^5$. R$^{2b}$ is F and R$^4$ is C(O)R$^5$ wherein R$^5$ is phenyl or substituted phenyl. R$^{2b}$ is OR$^4$ wherein R$^4$ is C(R$^5$)$_2$R$^6$ and R$^6$ is phenyl or substituted phenyl. R$^{2b}$ is OR$^4$ wherein R$^4$ is CH$_2$R$^6$ and R$^6$ is phenyl. R$^{2b}$ is OR$^4$ wherein R$^4$ is CH$_2$R$^6$ and R$^6$ is substituted phenyl. Each OR$^4$ and R$^{2b}$ is OH. R$^{2b}$ is OR$^4$ wherein each R$^4$ is independently C(R$^5$)$_2$R$^6$ and R$^6$ is phenyl or substituted phenyl. R$^{2b}$ is OR$^4$ wherein each R$^4$ is CH$_2$R$^6$ and R$^6$ is phenyl. R$^{2b}$ is OR$^4$ wherein each R$^4$ is CH$_2$R$^6$ and each R$^6$ is independently substituted phenyl. R$^{2b}$ is OR$^4$ wherein the two R$^4$ taken together are —C(R$^{19}$)$_2$—. R$^{2b}$ is OR$^4$ wherein the two R$^4$ taken together are —C(CH$_3$)$_2$—. R$^{2b}$ is OR$^4$ wherein the two R$^4$ taken together are —CH(R$^{19}$)—. R$^{2b}$ is OR$^4$ wherein the two R$^4$ taken together are —CH(R$^{19}$)— wherein R$^{19}$ is phenyl or substituted phenyl. R$^4$ is C(R$^5$)$_2$R$^6$, R$^6$ is phenyl or substituted phenyl and R$^{2b}$ is F.
(c) R$^7$ is C(O)R$^5$. R$^7$ is H. R$^7$ is C(R$^5$)$_2$R$^6$ and R$^6$ is phenyl or substituted phenyl. R$^7$ is CH$_2$R$^6$ and R$^6$ is phenyl. R$^7$ is CH$_2$R$^6$ and R$^6$ is substituted phenyl. R$^7$ is C(R$^5$)$_2$R$^6$ and each R$^5$ and R$^6$ is independently phenyl or substituted phenyl. R$^7$ is Si(R$^3$)$_3$. R$^7$ is Si(R$^3$)$_2$(t-butyl) wherein each R$^3$ is CH$_3$. R$^7$ is Si(R$^3$)$_2$(t-butyl) wherein each R$^3$ is independently phenyl or substituted phenyl. R$^7$ is tetrahydro-2H-pyran-2-yl. R$^7$ is C(R$^5$)$_2$R$^6$ wherein each R$^5$ and R$^6$ is independently phenyl or substituted phenyl and R$^{2b}$ is OR$^4$ wherein the two R$^4$ taken together are —C(CH$_3$)$_2$—. R$^7$ is Si(R$^3$)$_3$ and R$^{2b}$ is OR$^4$ wherein the two R$^4$ taken together are —C(CH$_3$)$_2$—. R$^7$ is Si(R$^3$)$_2$(t-butyl) wherein each R$^3$ is CH$_3$ and R$^{2b}$ is OR$^4$ wherein the two R$^4$ taken together are —C(CH$_3$)$_2$—. R$^7$ is Si(R$^3$)$_2$(t-butyl) wherein each R$^3$ is independently phenyl or substituted phenyl and R$^{2b}$ is OR$^4$ wherein the two R$^4$ taken together are —C(CH$_3$)$_2$—. R$^7$ is tetrahydro-2H-pyran-2-yl and R$^{2b}$ is OR$^4$ wherein the two R$^4$ taken together are —C(CH$_3$)$_2$—. R$^7$ is C(O)R$^5$ and R$^{2b}$ is OR$^4$ wherein the two R$^4$ taken together are —C(CH$_3$)$_2$—. R$^7$ is C(R$^5$)$_2$R$^6$ wherein each R$^5$ and R$^6$ is independently phenyl or substituted phenyl and R$^{2b}$ is OR$^4$ wherein the two R$^4$ taken together are —CH(R$^{19}$)— wherein R$^{19}$ is phenyl or substituted phenyl. R$^7$ is Si(R$^3$)$_3$ and R$^{2b}$ is OR$^4$ wherein the two R$^4$ taken together are —CH(R$^{19}$)— wherein R$^{19}$ is phenyl or substituted phenyl. R$^7$ is Si(R$^3$)$_2$(t-butyl) wherein each R$^3$ is CH$_3$ and R$^{2b}$ is OR$^4$ wherein the two R$^4$ taken together are —CH(R$^{19}$)— wherein R$^{19}$ is phenyl or substituted phenyl. R$^7$ is Si(R$^3$)$_2$(t-butyl) wherein each R$^3$ is independently phenyl or substituted phenyl and R$^{2b}$ is OR$^4$ wherein the two R$^4$ taken together are —CH(R$^{19}$)— wherein R$^{19}$ is phenyl or substituted phenyl. R$^7$ is tetrahydro-2H-pyran-2-yl and R$^{2b}$ is OR$^4$ wherein the two R$^4$ taken together are —CH(R$^{19}$)— wherein R$^{19}$ is phenyl or substituted phenyl. R$^7$ is C(O)R$^5$ and R$^{2b}$ is OR$^4$ wherein the two R$^4$ taken together are —CH(R$^{19}$)— wherein R$^{19}$ is phenyl or substituted phenyl. R$^7$ is C(O)R$^5$ wherein R$^5$ is phenyl or substituted phenyl and R$^{2b}$ is F.

(d) X$^1$ is C—R$^{10}$. X$^1$ is C—H. X$^1$ is N.
(e) R$^8$ is NR$^{11}$R$^{12}$. R$^8$ is OR$^{11}$. R$^8$ is SR$^{11}$
(f) R$^9$ is H. R$^9$ is NR$^{11}$R$^{12}$. R$^9$ is SR$^{11}$
(g) Each R$^{11}$ or R$^{12}$ is independently (C$_1$-C$_8$)alkyl, —C(=O)(C$_1$-C$_8$)alkyl, —S(O)$_n$(C$_1$-C$_8$)alkyl, aryl(C$_1$-C$_8$)alkyl or Si(R$^3$)$_3$; or R$^{11}$ and R$^{12}$ taken together with a nitrogen to which they are both attached form a 3 to 7 membered heterocyclic ring; or R$^{11}$ and R$^{12}$ taken together are —Si(R$^3$)$_2$(X$^2$)$_m$Si(R$^3$)$_2$—. Each R$^{11}$ or R$^{12}$ is independently (C$_1$-C$_8$)alkyl. Each R$^{11}$ or R$^{12}$ is independently Si(R$^3$)$_3$. Each R$^{11}$ or R$^{12}$ is independently Si(R$^3$)$_3$ wherein at least two of R$^3$ are CH$_3$ or phenyl. Each R$^1$ or R$^{12}$ is independently Si(CH$_3$)$_3$. Each R$^1$ and R$^{12}$ of NR$^{11}$R$^{12}$ is independently selected from Si(R$^3$)$_3$ or R$^{11}$ and R$^{12}$ of NR$^{11}$R$^{12}$ taken together are —Si(R$^3$)$_2$(X$^2$)$_m$Si(R$^3$)$_2$—. Each R$^{11}$ and R$^{12}$ of NR$^{11}$R$^{12}$ is independently selected from Si(R$^3$)$_3$ or R$^{11}$ and R$^{12}$ of NR$^{11}$R$^{12}$ taken together are —Si(R$^3$)$_2$(X$^2$)$_m$Si(R$^3$)$_2$—; and each R$^3$ is methyl.
(h) M is MgX$^3$. M is Li.

In another embodiment, the method of preparing a compound of Formula I further comprises the method of preparing a compound of Formula II wherein R$^{16}$ is OH.

In another embodiment, the method of preparing a compound of Formula Ib further comprises a method for preparing the compound of Formula IIb wherein R$^{16}$ is OH.

In another embodiment, the method of preparing a compound of Formula Ic further comprises the method for preparing a compound of Formula IIc wherein R$^{16}$ is OH.

Typically, the method of preparing a compound of Formula II, IIb or IIc wherein R$^{16}$ is OH from a compound of Formula III, IIIb or IIIc, respectively, is performed in a suitable aprotic solvent at about −100 to about to abut 50 OC for about 5 minutes to 24 hours. Non-limiting examples of suitable aprotic solvents include THF, dioxane and ether. More typically, the suitable solvent is THF and the preferred temperature is about −78 to 0° C. The mole ratio of the compound of Formula IV to the compound of Formula III, IIIb or IIIc is about 1:2 to 2:1; preferably about 1:1.

In another embodiment, the method of preparing a compound of Formula II, IIb or IIc wherein R$^{16}$ is OH from a compound of Formula III, IIIb or IIIc, respectively, further comprises a method of preparing a compound of Formula IV wherein M is MgX$^3$ or Li and X$^3$ is halogen, the method comprising:

(g) providing a compound of Formula V:

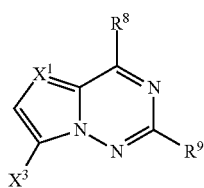

Formula V wherein $X^3$ is Cl, Br or I and (h) treating the compound of Formula V with an organometallic reagent comprising an organomagnesium or organolithium compound;

thereby forming a compound of Formula IV.

In another embodiment, the method of preparing a compound of Formula IV from a compound of Formula V comprises the following independent aspects:

(a) $X^1$ is C—$R^{10}$. $X^1$ is C—H. $X^1$ is N.

(b) $R^8$ is $NR^{11}R^{12}$. $R^8$ is $OR^{11}$. $R^8$ is $SR^{11}$ (c) $R^9$ is H. $R^9$ is $NR^{11}R^{12}$. $R^9$ is $SR^{11}$ (d) Each $R^{11}$ or $R^{12}$ is independently $(C_1$-$C_8)$alkyl, —C(=O)$(C_1$-$C_8)$alkyl, —S(O)$_n(C_1$-$C_8)$alkyl, aryl$(C_1$-$C_8)$alkyl or Si$(R^3)_3$; or $R^{11}$ and $R^{12}$ taken together with a nitrogen to which they are both attached form a 3 to 7 membered heterocyclic ring; or $R^{11}$ and $R^{12}$ taken together are —Si$(R^3)_2(X^2)_m$Si$(R^3)_2$—. Each $R^{11}$ or $R^{12}$ is independently $(C_1$-$C_8)$alkyl. Each $R^{11}$ or $R^{12}$ is independently Si$(R^3)_3$. Each $R^{11}$ or $R^{12}$ is independently Si$(R^3)_3$ wherein at least two of $R^3$ are $CH_3$ or phenyl. Each $R^{11}$ or $R^{12}$ is independently Si$(CH_3)_3$. Each $R^{11}$ and $R^{12}$ of $NR^{11}R^{12}$ is independently selected from Si$(R^3)_3$ or $R^{11}$ and $R^{12}$ of $NR^{11}R^{12}$ taken together are —Si$(R^3)_2(X^2)_m$Si$(R^3)_2$—. Each $R^{11}$ and $R^{12}$ of $NR^{11}R^{12}$ is independently selected from Si$(R^3)_3$ or $R^{11}$ and $R^{12}$ of $NR^{11}R^{12}$ taken together are —Si$(R^3)_2(X^2)_m$Si$(R^3)_2$—; and each $R^3$ is methyl.

(e) $X^3$ is $C_1$. $X^3$ is Br. $X^3$ is I.

In one embodiment, the method of preparing a compound of Formula IV comprises treating a compound of Formula V with a organomagnesium compound. Typically, the transmetalation reaction is performed in a suitable aprotic solvent at about −78 to about to abut 50° C. for about 5 minutes to 24 hours. Non-limiting examples of suitable aprotic solvents include THF, dioxane and ether. In one embodiment, the mole ratio of the compound of Formula V to organomagnesium compound is about 1:1 to about 1:3, preferably about 1:2. In one embodiment, the organomagnesium compound comprises an alkylmagnesium chloride, bromide, or iodide. In another embodiment, the organomagnesium compound comprises 2-propylmagnesium chloride. In one embodiment, the organomagnesium compound comprises an alkylmagnesium chloride, bromide, or iodide and lithium chloride. In another embodiment, the organomagnesium compound comprises 2-propylmagnesium chloride and lithium chloride. In another embodiment, the organomagnesium compound is 2-propylmagnesium chloride and lithium chloride in about a 1:1 mole ratio. In a preferred embodiment, the organomagnesium compound comprises 2-propylmagnesium chloride and lithium chloride in a 1:1 mole ratio and the $X^3$ of Formula IV is Br or I.

In another aspect wherein the compound of Formula IV is prepared by treating a compound of Formula V with a organomagnesium compound, the compound of Formula V may be treated with more than one organomagnesium compound. This procedure would be preferable when the compound of Formula V comprises a substituent with an acidic hydrogen. Non-limiting examples of the substituents with acidic hydrogens are $NH_2$, OH, SH, NH$(C_1$-$C_6$ alkyl) and the like. One skilled in the art will recognize that the acidic hydrogen group of the substituent of the compound of Formula V will consume one mole equivalent of the organomagnesium compound. The organomagnesium compound consumed may be different from the organomagnesium compound that produces the transmetalation reaction. For example, but not by way of limitation, treating the compound of Formula V with about one mole equivalent of methylmagnesium chloride would neutralize an acidic hydrogen of NH$(C_1$-$C_6$ alkyl), OH, or SH substituent by forming a magnesium salt and the $X^3$ group (Cl, Br, or I group) of the compound of Formula V may be transmetalated with another organomagnesium compound such as 2-propylmagnesium chloride or 2-propylmagnesium chloride and lithium chloride. Similarly, if additional acidic hydrogens are present, an additional about equivalent amount of organomagnesium compound would be required to neutralize each additional acidic hydrogen, e.g., each additional $NH_2$ substituent would require about two additional equivalents of organomagnesium compound. Typically, the transmetalation reactions of this aspect are performed in a suitable aprotic solvent at about −78 to about to abut 50° C. for about 5 minutes to 24 hours. Non-limiting examples of suitable aprotic solvents include THF, dioxane and ether. In one embodiment, the compound of Formula IV is prepared by treating the compound of Formula V with about one mole equivalent of a first organomagnesium compound for each acidic hydrogen in a substitutent followed by treatment with a second organomagnesium compound to transmetallate the $X^3$ group of Formula V. In one embodiment, the mole ratio of the first organomagnesium compound to each acid hydrogen in a substituent of a molecule of Formula V is about 1:1 to about 1:1.4 and the mole ratio of the second organomagnesium compound to the compound of Formula V is about 1:0.8 to about 1:2. In one embodiment, the first organomagnesium compound comprises an alkylmagnesium chloride, bromide, or iodide. In another embodiment, the first organomagnesium compound comprises methylmagnesium chloride. In another embodiment, the second organomagnesium compound comprises an alkylmagnesium chloride, bromide, or iodide. In another embodiment, the second alkylmagnesium compound comprises 2-propylmagnesium chloride. In one embodiment, the second organomagnesium compound comprises an alkylmagnesium chloride, bromide, or iodide and lithium chloride. In another embodiment the second organomagnesium compound is 2-propylmagnesium chloride and lithium chloride in a 1:1 mole ratio. In a preferred embodiment, the first organomagnesium compound is methylmagnesium chloride and the second organomagnesium compound comprises 2-propylmagnesium chloride. In another preferred embodiment the first organomagnesium compound is methylmagnesium chloride and the second organomagnesium compound is 2-propylmagnesium chloride and lithium chloride in a 1:1 mole ratio. In another preferred embodiment the first organomagnesium compound is methylmagnesium chloride, the second organomagnesium compound is 2-propylmagnesium chloride and lithium chloride in about 1:1 mole ratio, and the $X^3$ of Formula V is Br or I. In another preferred embodiment the first organomagnesium compound is methylmagnesium chloride, the second organomagnesium compound is 2-propylmagnesium chloride and lithium chloride in about 1:1 mole ratio, the $X^3$ of Formula V is Br or I. and $R^8$ is $NH_2$.

The magnesium salts of the substituents of Formula V discussed above may be converted to a protected form of the substituent such as, but not limited to, a silyl protected substituent. Subsequently, the $X^3$ group (Cl, Br, or I group) of the compound of Formula V may be transmetalated with the same or a different organomagnesium compound such as 2-propylmagnesium chloride or 2-propylmagnesium chloride and lithium chloride. Similarly, if additional acidic hydrogens are present, an additional about one equivalent amount of organomagnesium compound would be required to neutralize each additional acidic hydrogen, e.g., each additional $NH_2$ substituent would require about two additional equivalents of organomagnesium compound and the resulting magnesium salts could be converted to protecting groups, such as but not limited to, silyl protecting groups. Non-limiting examples of the resulting protected substituents would be $OSi(R^3)_3$, $SSi(R^3)_3$, $N[Si(R^3)_3][C_1-C_6 \text{ alkyl}]$, $N[Si(R^3)_2(CH_2)_2 \text{ } Si(R^3)_2]$ and $N[Si(R^3)_3]_2$. All such intermediates with protected substituents are within the scope of the instant invention. Non-limiting examples of silylating reagents to convert the intermediate magnesium salt of the substituents to protected substituents include $X^3Si(R^3)_3$, $X^3Si(R^3)_2(CH_2)_2 \text{ } Si(R^3)_2X^3$ and $(R^{20})_3CS(O)_2OSi(R^3)_3$; more specifically $ClSi(R^3)_3$, $ClSi(R^3)_2(CH_2)_2 \text{ } Si(R^3)_2Cl$ and $CF_3S(O)_2OSi(R^3)_3$; and most specifically $ClSi(CH_3)_3$, $ClSi(CH_3)_2(CH_2)_2 \text{ } Si(CH_3)_2Cl$ and $CF_3S(O)_2OSi(CH_3)_3$. These silylating reagents may be present before the addition of the initial organometallic agent if the temperature of the reaction is sufficiently controlled or they may be added after conversion of the substituent to the magnesium salt.

Typically, the conversion of substituents of Formula V with acidic hydrogens to protected substituents are performed in a suitable aprotic solvent at about −78 to about to abut 50° C. for about 5 minutes to 24 hours. Non-limiting examples of suitable aprotic solvents include THF, dioxane and ether.

In one embodiment, the compound of Formula IV is prepared by treating the compound of Formula V comprising substituents with acidic hydrogens with about one mole equivalent of a first organomagnesium compound for each acidic hydrogen in a substituent, treatment with about 1-1.4 equivalents of protecting group reagent for each acid hydrogen, and treatment with 1-2 equivalents of the same or a different organomagnesium compound to transmetallate the $X^3$ group of Formula V.

In another embodiment, the compound of Formula IV is prepared by treating a mixture of compound of Formula V and about 1-1.4 equivalents of protecting group reagent per acidic hydrogen in Formula V with about 1-1.4 equivalents of a first organomagnesium compound for each acid hydrogen in a substituent, followed by treatment with 1-2 equivalents of the same or a different organomagnesium compound to transmetallate the $X^3$ group of Formula V.

In another embodiment, the compound of Formula IV is prepared by treating a mixture of compound of Formula V and about 1-1.4 equivalents of protecting reagent per acidic hydrogen in Formula V with about 1-1.4 equivalents of a organomagnesium compound for each acid hydrogen in a substitutent and an additional 1-2 equivalents of organomagnesium compound to transmetallate the $X^3$ group of Formula V. In another aspect of this embodiment, the $X^3$ of Formula V is Br or I and $R^8$ of Formula V is $NH_2$.

In another embodiment, the method of preparing a compound of Formula I or Formula Ib further comprises a method of preparing a compound of Formula IV wherein M is Li by treating a compound of Formula V with an organolithium compound. Typically, the transmetalation reaction is performed in a suitable aprotic solvent at about −100 to about to abut 20 OC for about 5 minutes to 24 hours. Non-limiting examples of suitable aprotic solvents include THF and ether. In one aspect of this embodiment, the mole ratio of the compound of Formula V to organolithium compound is about 1:1 to about 1:3, preferably about 1:1.4. In another aspect of this embodiment, the organolithium compound comprises an alkyllithium compound. In another aspect of this embodiment, the organolithium compound comprises n-butyllithium. In another aspect of this embodiment, the organolithium compound comprises iso-butyllithium. In another aspect of this embodiment, the organolithium compound comprises tert-butyllithium. In a preferred aspect of this embodiment, the organolithium compound comprises an alkyllithium compound and the $X^3$ of Formula V is Br or I.

In another embodiment wherein the compound of Formula IV is prepared by treating a compound of Formula V with an organolithium compound, the compound of Formula V may be treated with more than one mole equivalent of organolithium compound. This procedure would be preferable when the compound of Formula V is comprised of a substituent with an acidic hydrogen. Non-limiting examples of the substituents with acidic hydrogens are $NH_2$, OH, SH, $NH(C_1-C_6 \text{ alkyl})$ and the like. One skilled in the art will recognize that the acidic hydrogen group of the substituent of the compound of Formula V will consume one mole equivalent of the organolithium compound. For example, but not by way of limitation, treating the compound of Formula V with about one mole equivalent of organolithium compound would neutralize an acidic hydrogen of $NH(C_1-C_6 \text{ alkyl})$, OH, or SH substituent by forming a lithium salt and the $X^3$ group (Cl, Br, or I group) of the compound of Formula V may be transmetalated with another mole equivalent of organolithium compound. Similarly, if additional acidic hydrogens are present, an additional about equivalent amount of organolithium compound would be required to neutralize each additional acidic hydrogen, e.g., each additional $NH_2$ substituent would require about two additional equivalents of organolithium compound. Typically, the transmetalation reactions of this aspect are performed in a suitable aprotic solvent at about −100 to about to abut 20° C. for about 5 minutes to 24 hours. Non-limiting examples of suitable aprotic solvents include THF, dioxane and ether. In one embodiment, the mole ratio of the organolithium compound to the each acid hydrogen in a substituent of a molecule of Formula V is about 1:1 to about 1:1.4 and the mole ratio of the additional amount of organolithium compound to the compound of Formula V is about 1:0.8 to about 1:1.4. In another aspect of this embodiment, the organolithium compound comprises an alkyllithium compound. In another embodiment, the organolithium compound comprises n-butyllithium. In another embodiment, the organolithium compound comprises iso-butyllithium. In another embodiment, the organolithium compound comprises tert-butyllithium. In a preferred embodiment, the organolithium compound comprises a $(C_1-C_6)$alkyllithium compound and the $X^3$ of Formula V is Br or I.

The lithium salts of the substituents of Formula V discussed above may be converted to a protected form of the substituent such as, but not limited to, a silyl protected substituent. Subsequently, the $X^3$ group (Cl, Br, or I group) of the compound of Formula V may be transmetalated with the same or a different organolithium compound. Similarly, if additional acidic hydrogens are present, an additional about one equivalent amount of organolithium compound would be required to neutralize each additional acidic hydrogen, e.g., each additional $NH_2$ substituent would require about two additional equivalents of organolithium compound and the resulting lithium salts could be converted to protecting groups, such as but not limited to, silyl protecting groups. Non-limiting examples of the resulting protected substituents would be $OSi(R^3)_3$, $SSi(R^3)_3$, $N[Si(R^3)_3][C_1\text{-}C_6$ alkyl], $N[Si(R^3)_2(CH_2)_2 Si(R^3)_2]$ and $N[Si(R^3)_3]_2$. All such intermediates with protected substituents are within the scope of the instant invention. Non-limiting examples of silylating reagents to convert the intermediate lithium salt of the substituents to protected substituents include $X^3Si(R^3)_3$, $X^3Si(R^3)_2(CH_2)_2 Si(R^3)_2X^3$ and $(R^{20})_3CS(O)_2OSi(R^3)_3$; more specifically $ClSi(R^3)_3$, $ClSi(R^3)_2(CH_2)_2 Si(R^3)_2Cl$ and $CF_3S(O)_2OSi(R^3)_3$, and most specifically $ClSi(CH_3)_3$, $ClSi(CH_3)_2(CH_2)_2 Si(CH_3)_2C_1$ and $CF_3S(O)_2OSi(CH_3)_3$. These silylating reagents may be present before the addition of the initial organometallic agent if the temperature of the reaction is sufficiently controlled or they may be added after conversion of the substituent to the lithium salt.

Typically, the conversion of substituents of Formula V with acid hydrogens to protected substituents are performed in a suitable aprotic solvent at about −100 to about to abut 20° C. for about 5 minutes to 24 hours. Non-limiting examples of suitable aprotic solvents include THF, dioxane and ether.

In one embodiment, the compound of Formula IV is prepared by treating the compound of Formula V comprising substituents with acid hydrogens with about 1-1.4 mole equivalent of a organolithium compound for each acid hydrogen in a substitutent, treatment with about 1-1.4 equivalents of protecting group reagent for each acid hydrogen, and treatment with 1-1.4 equivalents of the same or a different organolithium compound to transmetallate the $X^3$ group of Formula V.

In another embodiment, the compound of Formula IV is prepared by treating a mixture of compound of Formula V and about 1-1.4 equivalents of protecting group reagent per acidic hydrogen in Formula V with about 1-1.4 equivalents of a first organolithium compound for each acid hydrogen in a substituent, followed by treatment with 1-1.4 equivalents of the same or a different organolithium compound to transmetallate the $X^3$ group of Formula V.

In another embodiment, the compound of Formula IV is prepared by treating a mixture of compound of Formula V and about 1-1.4 equivalents of protecting reagent per acidic hydrogen in Formula V with about 1-1.4 equivalents of a organolithium compound for each acid hydrogen in a substitutent and an additional 1-1.4 equivalents of organolithium compound to transmetallate the $X^3$ group of Formula V. In another aspect of this embodiment, the $X^3$ of Formula V is Br or I. and $R^8$ of Formula V is $NH_2$. In another aspect of this embodiment, the organolithium compound comprises an alkyllithium compound. In another embodiment, the organolithium compound comprises n-butyllithium. In another embodiment, the organolithium compound comprises iso-butyllithium. In another embodiment, the organolithium compound comprises tert-butyllithium. In a preferred embodiment, the organolithium compound comprises a $(C_1\text{-}C_6)$alkyllithium compound and the $X^3$ of Formula V is Br or I. In another embodiment, the protecting group reagent is a silylating reagent. In another embodiment, the protecting group reagent is $X^3Si(R^3)_3$ or $(R^{20})_3CS(O)_2OSi(R^3)_3$. In another embodiment, the protecting group reagent is ClSi $(R^3)_3$ or $CF_3S(O)_2OSi(R^3)_3$. In another embodiment, the protecting group reagent is $ClSi(CH_3)_3$ or $CF_3S(O)_2OSi(CH_3)_3$.

In another embodiment, provided are useful intermediates for the syntheses of compounds of Formula I represented by Formula VI. In one embodiment, $R^{17}$ is OH.

In another embodiment, $R^{17}$ is $—OC(O)R^{18}$. In another embodiment, $R^{17}$ is $—OC(O)OR^{18}$. In another embodiment, $R^{17}$ is $OR^{18}$.

In another embodiment, provided is a compound of Formula IIb represented by Formula VIb:

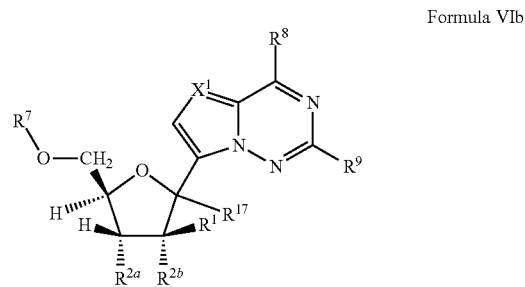

Formula VIb or an acceptable salt, thereof;
wherein the variables are defined as for Formula VI.

In one embodiment of the compound of Formula VIb, $R^{17}$ is OH. The following are additional independent aspects of this embodiment:

(a) $R^1$ is H. $R^1$ is $CH_3$.
(b) $X^1$ is C—$R^{10}$. $X^1$ is C—H. $X^1$ is N.
(c) $R^8$ is $NR^{11}R^{12}$. $R^8$ is $OR^{11}$. $R^8$ is $SR^{11}$
(d) $R^9$ is H. $R^9$ is $NR^{11}R^{12}$. $R^9$ is $SR^{11}$
(e) $R^{2b}$ is $OR^4$. $R^{2b}$ is F. Each $R^{2a}$ and $R^{2b}$ is independently $OR^4$. $R^{2a}$ is $OR^4$ and $R^{2b}$ is F. $R^{2a}$ is $OR^4$, $R^{2b}$ is F and $R^4$ is $C(O)R^5$. $R^{2a}$ is $OR^4$, $R^{2b}$ is F and $R^4$ is $C(O)R^5$ wherein $R^5$ is phenyl or substituted phenyl. $R^{2b}$ is $OR^4$ wherein $R^4$ is $C(R^5)_2R^6$ and $R^6$ is phenyl or substituted phenyl. $R^{2b}$ is $OR^4$ wherein $R^4$ is $CH_2R^6$ and $R^6$ is phenyl. $R^{2b}$ is $OR^4$ wherein $R^4$ is $CH_2R^6$ and $R^6$ is substituted phenyl. Each $R^{2a}$ and $R^{2b}$ is $OR^4$ wherein each $R^4$ is independently $C(R^5)_2R^6$ and $R^6$ is phenyl or substituted phenyl. Each $R^{2a}$ and $R^{2b}$ is $OR^4$ wherein each $R^4$ is $CH_2R^6$ and $R^6$ is phenyl. Each $R^{2a}$ and $R^{2b}$ is $OR^4$ wherein each $R^4$ is $CH_2R^6$ and each $R^6$ is independently substituted phenyl. Each $R^{2a}$ and $R^{2b}$ is $OR^4$ wherein the two $R^4$ taken together are $—C(R^{19})_2—$. Each $R^{2a}$ and $R^{2b}$ is $OR^4$ wherein the two $R^4$ taken together are $—C(CH_3)_2—$. Each $R^{2a}$ and $R^{2b}$ is $OR^4$ wherein the two $R^4$ taken together are $—CH(R^{19})—$. Each $R^{2a}$ and $R^{2b}$ is $OR^4$ wherein the two $R^4$ taken together are $—CH(R^{19})—$ wherein $R^{19}$ is phenyl or substituted phenyl. $R^{2a}$ is $OR^4$ wherein $R^4$ is $C(R^5)_2R^6$, $R^6$ is phenyl or substituted phenyl and $R^{2b}$ is F. $R^{2a}$ is H.

(f) $R^7$ is $C(O)R^5$. $R^7$ is $C(R^5)_2R^6$ and $R^6$ is phenyl or substituted phenyl. $R^7$ is $CH_2R^6$ and $R^6$ is phenyl. $R^7$ is $CH_2R^6$ and $R^6$ is substituted phenyl. $R^7$ is $C(R^5)_2R^6$ and each $R^5$ and $R^6$ is independently phenyl or substituted phenyl. $R^7$ is $Si(R^3)_3$. $R^7$ is $Si(R^3)_2$(t-butyl) wherein each $R^3$ is $CH_3$. $R^7$ is $Si(R^3)_2$(t-butyl) wherein each $R^3$ is independently phenyl or substituted phenyl. $R^7$ is tetrahydro-2H-pyran-2-yl. $R^7$ is $C(R^5)_2R^6$ wherein each $R^5$ and $R^6$ is independently phenyl or substituted phenyl and each $R^{2a}$ and $R^{2b}$ is $OR^4$ wherein the two $R^4$ taken together are $—C(CH_3)_2—$. $R^7$ is $Si(R^3)_3$ and each $R^{2a}$ and $R^{2b}$ is $OR^4$ wherein the two $R^4$ taken together are $—C(CH_3)_2—$. $R^7$ is $Si(R^3)_2$(t-butyl) wherein each $R^3$ is CH$_3$ and each R$^{2a}$ and R$^{2b}$ is OR$^4$ wherein the two R$^4$ taken together are —C(CH$_3$)$_2$—. R$^7$ is Si(R$^3$)$_2$(t-butyl) wherein each R$^3$ is independently phenyl or substituted phenyl and each R$^{2a}$ and R$^{2b}$ is OR$^4$ wherein the two R$^4$ taken together are —C(CH$_3$)$_2$—. R$^7$ is tetrahydro-2H-pyran-2-yl and each R$^{2a}$ and R$^{2b}$ is OR$^4$ wherein the two R$^4$ taken together are —C(CH$_3$)$_2$—. R$^7$ is C(O)R$^5$ and each R$^{2a}$ and R$^{2b}$ is OR$^4$ wherein the two R$^4$ taken together are —C(CH$_3$)$_2$—. R$^7$ is C(R$^5$)$_2$R$^6$ wherein each R$^5$ and R$^6$ is independently phenyl or substituted phenyl and each R$^{2a}$ and R$^{2b}$ is OR$^4$ wherein the two R$^4$ taken together are —CH(R$^{19}$)— wherein R$^{19}$ is phenyl or substituted phenyl. R$^7$ is Si(R$^3$)$_3$ and each R$^{2a}$ and R$^{2b}$ is OR$^4$ wherein the two R$^4$ taken together are —CH(R$^{19}$)— wherein R$^{19}$ is phenyl or substituted phenyl. R$^7$ is Si(R$^3$)$_2$(t-butyl) wherein each R$^3$ is CH$_3$ and each R$^{2a}$ and R$^{2b}$ is OR$^4$ wherein the two R$^4$ taken together are —CH(R$^{19}$)— wherein R$^{19}$ is phenyl or substituted phenyl. R$^7$ is Si(R$^3$)$_2$(t-butyl) wherein each R$^3$ is independently phenyl or substituted phenyl and each R$^{2a}$ and R$^{2b}$ is OR$^4$ wherein the two R$^4$ taken together are —CH(R$^{19}$)— wherein R$^{19}$ is phenyl or substituted phenyl. R$^7$ is tetrahydro-2H-pyran-2-yl and each R$^{2a}$ and R$^{2b}$ is OR$^4$ wherein the two R$^4$ taken together are —CH(R$^{19}$)— wherein R$^{19}$ is phenyl or substituted phenyl. R$^7$ is C(O)R$^5$ and each R$^{2a}$ and R$^{2b}$ is OR$^4$ wherein the two R$^4$ taken together are —CH(R$^{19}$)— wherein R$^{19}$ is phenyl or substituted phenyl. R$^7$ is C(O)R$^5$ wherein R$^5$ is phenyl or substituted phenyl and R$^{2b}$ is F.

(g) R$^1$ is H, X$^1$ is CH, and R$^8$ is NR$^{11}$R$^{12}$. R$^1$ is H, X$^1$ is CH, and R$^8$ is NH$_2$. R$^1$ is CH$_3$, X$^1$ is CH, and R$^8$ is NR$^{11}$R$^{12}$. R$^1$ is CH$_3$, X$^1$ is CH, and R$^8$ is NH$_2$. R$^1$ is H, X$^1$ is N, and R$^8$ is NR$^{11}$R$^{12}$. R$^1$ is H, X$^1$ is N, and R$^8$ is NH$_2$. R$^1$ is CH$_3$, X$^1$ is N, and R$^8$ is NR$^{11}$R$^{12}$. R$^1$ is CH$_3$, X$^1$ is N, and R$^8$ is NH$_2$. R$^1$ is H, X$^1$ is CH, and R$^9$ is NR$^{11}$R$^{12}$. R$^1$ is H, X$^1$ is CH, and R$^9$ is NH$_2$. R$^1$ is H, X$^1$ is CH, and R$^9$ is SR$^{11}$. R$^1$ is H, X$^1$ is CH, and R$^9$ is SH. R$^1$ is H, X$^1$ is CH, and R$^9$ is H. R$^1$ is CH$_3$, X$^1$ is CH, and R$^9$ is NR$^{11}$R$^{12}$. R$^1$ is CH$_3$, X$^1$ is CH, and R$^9$ is NH$_2$. R$^1$ is CH$_3$, X$^1$ is CH, and R$^9$ is SR$^{11}$. R$^1$ is CH$_3$, X$^1$ is CH, and R$^9$ is SH. R$^1$ is CH$_3$, X$^1$ is CH, and R$^9$ is H.

(h) R$^1$ is H, X$^1$ is CH, and R$^8$ is OR$^{11}$. R$^1$ is H, X$^1$ is CH, and R$^8$ is OH. R$^1$ is CH$_3$, X$^1$ is CH, and R$^8$ is OR$^{11}$. R$^1$ is CH$_3$, X$^1$ is CH, and R$^8$ is OH. R$^1$ is H, X$^1$ is N, and R$^8$ is OR$^{11}$. R$^1$ is H, X$^1$ is N, and R$^8$ is OH. R$^1$ is CH$_3$, X$^1$ is N, and R$^8$ is OR$^{11}$. R$^1$ is CH$_3$, X$^1$ is N, and R$^8$ is OH.

(i) R$^1$ is H, X$^1$ is CH, and R$^8$ is SR$^{11}$. R$^1$ is H, X$^1$ is CH, and R$^8$ is SH. R$^1$ is CH$_3$, X$^1$ is CH, and R$^8$ is SR$^{11}$. R$^1$ is CH$_3$, X$^1$ is CH, and R$^8$ is SH. R$^1$ is H, X$^1$ is N, and R$^8$ is SR$^{11}$. R$^1$ is H, X$^1$ is N, and R$^8$ is SH. R$^1$ is CH$_3$, X$^1$ is N, and R$^8$ is SR$^{11}$. R$^1$ is CH$_3$, X$^1$ is N, and R$^8$ is SH.

(j) R$^1$ is H, X$^1$ is CH, R$^9$ is H and R$^8$ is NR$^{11}$R$^{12}$. R$^1$ is H, X$^1$ is CH, R$^9$ is H and R$^8$ is NH$_2$. R$^1$ is CH$_3$, X$^1$ is CH, R$^9$ is H and R$^8$ is NR$^{11}$R$^{12}$. R$^1$ is CH$_3$, X$^1$ is CH, R$^9$ is H and R$^8$ is NH$_2$. R$^1$ is H, X$^1$ is N, R$^9$ is H and R$^8$ is NR$^{11}$R$^{12}$. R$^1$ is H, X$^1$ is N, R$^9$ is H and R$^8$ is NH$_2$. R$^1$ is CH$_3$, X$^1$ is N, R$^9$ is H and R$^8$ is NR$^{11}$R$^{12}$. R$^1$ is CH$_3$, X$^1$ is N, R$^9$ is H and R$^8$ is NH$_2$. R$^1$ is H, X$^1$ is CH, R$^9$ is NR$^{11}$R$^{12}$ and R$^8$ is NR$^{11}$R$^{12}$. R$^1$ is H, X$^1$ is CH, R$^9$ is NR$^{11}$R$^{12}$ and R$^8$ is NH$_2$. R$^1$ is CH$_3$, X$^1$ is CH, R$^9$ is NR$^{11}$R$^{12}$ and R$^8$ is NR$^{11}$R$^{12}$. R$^1$ is CH$_3$, X$^1$ is CH, R$^9$ is NR$^{11}$R$^{12}$ and R$^8$ is NH$_2$. R$^1$ is H, X$^1$ is N, R$^9$ is NR$^{11}$R$^{12}$ and R$^8$ is NR$^{11}$R$^{12}$. R$^1$ is H, X$^1$ is N, R$^9$ is NR$^{11}$R$^{12}$ and R$^8$ is NH$_2$. R$^1$ is CH$_3$, X$^1$ is N, R$^9$ is NR$^{11}$R$^{12}$ and R$^8$ is NR$^{11}$R$^{12}$. R$^1$ is CH$_3$, X$^1$ is N, R$^9$ is NR$^{11}$R$^{12}$ and R$^8$ is NH$_2$.

(k) R$^1$ is H, X$^1$ is CH, and R$^8$ and R$^9$ are independently SR$^{11}$. R$^1$ is CH$_3$, X$^1$ is CH, and R$^8$ and R$^9$ are independently SR$^{11}$. R$^1$ is H, X$^1$ is N, and R$^8$ and R$^9$ are independently SR$^{11}$. R$^1$ is CH$_3$, X$^1$ is N, and R$^8$ and R$^9$ are independently SR$^{11}$ In one embodiment of the compound of Formula VIb, R$^{17}$ is —OR$^{18}$. The following are additional independent aspects of this embodiment:

(a) R$^1$ is H. R$^1$ is CH$_3$.

(b) X$^1$ is C—R$^{10}$. X$^1$ is C—H. X$^1$ is N.

(c) R$^8$ is NR$^{11}$R$^{12}$. R$^8$ is OR$^{11}$. R$^8$ is SR$^{11}$ (d) R$^9$ is H. R$^9$ is NR$^{11}$R$^{12}$. R$^9$ is SR$^{11}$ (e) R$^{2b}$ is OR$^4$. R$^{2b}$ is F. Each R$^{2a}$ and R$^{2b}$ is independently OR$^4$. R$^{2a}$ is OR$^4$ and R$^{2b}$ is F. R$^{2a}$ is OR$^4$, R$^{2b}$ is F and R$^4$ is C(O)R$^5$. R$^{2a}$ is OR$^4$, R$^{2b}$ is F and R$^4$ is C(O)R$^5$ wherein R$^5$ is phenyl or substituted phenyl. R$^{2b}$ is OR$^4$ wherein R$^4$ is C(R$^5$)$_2$R$^6$ and R$^6$ is phenyl or substituted phenyl. R$^{2b}$ is OR$^4$ wherein R$^4$ is CH$_2$R$^6$ and R$^6$ is phenyl. R$^{2b}$ is OR$^4$ wherein R$^4$ is CH$_2$R$^6$ and R$^6$ is substituted phenyl. Each R$^{2a}$ and R$^{2b}$ is OR$^4$ wherein each R$^4$ is independently C(R$^5$)$_2$R$^6$ and R$^6$ is phenyl or substituted phenyl. Each R$^{2a}$ and R$^{2b}$ is OR$^4$ wherein each R$^4$ is CH$_2$R$^6$ and R$^6$ is phenyl. Each R$^{2a}$ and R$^{2b}$ is OR$^4$ wherein each R$^4$ is CH$_2$R$^6$ and each R$^6$ is independently substituted phenyl. Each R$^{2a}$ and R$^{2b}$ is OR$^4$ wherein the two R$^4$ taken together are —C(R$^{19}$)$_2$—. Each R$^{2a}$ and R$^{2b}$ is OR$^4$ wherein the two R$^4$ taken together are —C(CH$_3$)$_2$—. Each R$^{2a}$ and R$^{2b}$ is OR$^4$ wherein the two R$^4$ taken together are —CH(R$^{19}$)—. Each R$^{2a}$ and R$^{2b}$ is OR$^4$ wherein the two R$^4$ taken together are —CH(R$^{19}$)— wherein R$^{19}$ is phenyl or substituted phenyl. R$^{2a}$ is OR$^4$ wherein R$^4$ is C(R$^5$)$_2$R$^6$, R$^6$ is phenyl or substituted phenyl and R$^{2b}$ is F. R$^{2a}$ is H.

(f) R$^7$ is C(O)R$^5$. R$^7$ is C(R$^5$)$_2$R$^6$ and R$^6$ is phenyl or substituted phenyl. R$^7$ is CH$_2$R$^6$ and R$^6$ is phenyl. R$^7$ is CH$_2$R$^6$ and R$^6$ is substituted phenyl. R$^7$ is C(R$^5$)$_2$R$^6$ and each R$^5$ and R$^6$ is independently phenyl or substituted phenyl. R$^7$ is Si(R$^3$)$_3$. R$^7$ is Si(R$^3$)$_2$(t-butyl) wherein each R$^3$ is CH$_3$. R$^7$ is Si(R$^3$)$_2$(t-butyl) wherein each R$^3$ is independently phenyl or substituted phenyl. R$^7$ is tetrahydro-2H-pyran-2-yl. R$^7$ is C(R$^5$)$_2$R$^6$ wherein each R$^5$ and R$^6$ is independently phenyl or substituted phenyl and each R$^{2a}$ and R$^{2b}$ is OR$^4$ wherein the two R$^4$ taken together are —C(CH$_3$)$_2$—. R$^7$ is Si(R$^3$)$_3$ and each R$^{2a}$ and R$^{2b}$ is OR$^4$ wherein the two R$^4$ taken together are —C(CH$_3$)$_2$—. R$^7$ is Si(R$^3$)$_2$(t-butyl) wherein each R$^3$ is CH$_3$ and each R$^{2a}$ and R$^{2b}$ is OR$^4$ wherein the two R$^4$ taken together are —C(CH$_3$)$_2$—. R$^7$ is Si(R$^3$)$_2$(t-butyl) wherein each R$^3$ is independently phenyl or substituted phenyl and each R$^{2a}$ and R$^{2b}$ is OR$^4$ wherein the two R$^4$ taken together are —C(CH$_3$)$_2$—. R$^7$ is tetrahydro-2H-pyran-2-yl and each R$^{2a}$ and R$^{2b}$ is OR$^4$ wherein the two R$^4$ taken together are —C(CH$_3$)$_2$—. R$^7$ is C(O)R$^5$ and each R$^{2a}$ and R$^{2b}$ is OR$^4$ wherein the two R$^4$ taken together are —C(CH$_3$)$_2$—. R$^7$ is C(R$^5$)$_2$R$^6$ wherein each R$^5$ and R$^6$ is independently phenyl or substituted phenyl and each R$^{2a}$ and R$^{2b}$ is OR$^4$ wherein the two R$^4$ taken together are —CH(R$^{19}$)— wherein R$^{19}$ is phenyl or substituted phenyl. R$^7$ is Si(R$^3$)$_3$ and each R$^{2a}$ and R$^{2b}$ is OR$^4$ wherein the two R$^4$ taken together are —CH(R$^{19}$)— wherein R$^{19}$ is phenyl or substituted phenyl. R$^7$ is Si(R$^3$)$_2$(t-butyl) wherein each R$^3$ is CH$_3$ and each R$^{2a}$ and R$^{2b}$ is OR$^4$ wherein the two R$^4$ taken together are —CH(R$^{19}$)— wherein R$^{19}$ is phenyl or substituted phenyl. R$^7$ is Si(R$^3$)$_2$(t-butyl) wherein each R$^3$ is independently phenyl or substituted phenyl and each R$^{2a}$ and R$^{2b}$ is OR$^4$ wherein the two R$^4$ taken together are —CH(R$^{19}$)— wherein R$^{19}$ is phenyl or substituted phenyl. R$^7$ is tetrahydro-2H-pyran-2-yl and each R$^{2a}$ and R$^{2b}$ is OR$^4$ wherein the two R$^4$ taken together are —CH(R$^{19}$)— wherein R$^{19}$ is phenyl or substituted phenyl. R$^7$ is C(O)R$^5$ and each R$^{2a}$ and R$^{2b}$ is OR$^4$ wherein the two R$^4$ taken together are —CH(R$^{19}$)— wherein R$^{19}$ is phenyl or substituted phenyl. R$^7$ is C(O)R$^5$ wherein R$^5$ is phenyl or substituted phenyl and R$^{2b}$ is F.

(g) $R^{18}$ is $(C_1-C_8)$alkyl or substituted $(C_1-C_8)$alkyl. $R^{18}$ is $(C_1-C_8)$alkyl. $R^{18}$ is methyl.

(h) $R^1$ is H, $X^1$ is CH, and $R^8$ is $NR^{11}R^{12}$. $R^1$ is H, $X^1$ is CH, and $R^8$ is $NH_2$. $R^1$ is $CH_3$, $X^1$ is CH, and $R^8$ is $NR^{11}R^{12}$. $R^1$ is $CH_3$, $X^1$ is CH, and $R^8$ is $NH_2$. $R^1$ is H, $X^1$ is N, and $R^8$ is $NR^{11}R^{12}$. $R^1$ is H, $X^1$ is N, and $R^8$ is $NH_2$. $R^1$ is $CH_3$, $X^1$ is N, and $R^8$ is $NR^{11}R^{12}$. $R^1$ is $CH_3$, $X^1$ is N, and $R^8$ is $NH_2$. $R^1$ is H, $X^1$ is CH, and $R^9$ is $NR^{11}R^{12}$. $R^1$ is H, $X^1$ is CH, and $R^9$ is $NH_2$. $R^1$ is H, $X^1$ is CH, and $R^9$ is $SR^{11}$. $R^1$ is H, $X^1$ is CH, and $R^9$ is SH. $R^1$ is H, $X^1$ is CH, and $R^9$ is H. $R^1$ is $CH_3$, $X^1$ is CH, and $R^9$ is $NR^{11}R^{12}$. $R^1$ is $CH_3$, $X^1$ is CH, and $R^9$ is $NH_2$. $R^1$ is $CH_3$, $X^1$ is CH, and $R^9$ is $SR^{11}$. $R^1$ is $CH_3$, $X^1$ is CH, and $R^9$ is SH. $R^1$ is $CH_3$, $X^1$ is CH, and $R^9$ is H.

(i) $R^1$ is H, $X^1$ is CH, and $R^8$ is $OR^{11}$. $R^1$ is H, $X^1$ is CH, and $R^8$ is OH. $R^1$ is $CH_3$, $X^1$ is CH, and $R^8$ is $OR^{11}$. $R^1$ is $CH_3$, $X^1$ is CH, and $R^8$ is OH. $R^1$ is H, $X^1$ is N, and $R^8$ is $OR^{11}$. $R^1$ is H, $X^1$ is N, and $R^8$ is OH. $R^1$ is $CH_3$, $X^1$ is N, and $R^8$ is $OR^{11}$. $R^1$ is $CH_3$, $X^1$ is N, and $R^8$ is OH.

(j) $R^1$ is H, $X^1$ is CH, and $R^8$ is $SR^{11}$. $R^1$ is H, $X^1$ is CH, and $R^8$ is SH. $R^1$ is $CH_3$, $X^1$ is CH, and $R^8$ is $SR^{11}$. $R^1$ is $CH_3$, $X^1$ is CH, and $R^8$ is SH. $R^1$ is H, $X^1$ is N, and $R^8$ is $SR^{11}$. $R^1$ is H, $X^1$ is N, and $R^8$ is SH. $R^1$ is $CH_3$, $X^1$ is N, and $R^8$ is $SR^{11}$. $R^1$ is $CH_3$, $X^1$ is N, and $R^8$ is SH.

(k) $R^1$ is H, $X^1$ is CH, $R^9$ is H and $R^8$ is $NR^{11}R^{12}$. $R^1$ is H, $X^1$ is CH, $R^9$ is H and $R^8$ is $NH_2$. $R^1$ is $CH_3$, $X^1$ is CH, $R^9$ is H and $R^8$ is $NR^{11}R^{12}$. $R^1$ is $CH_3$, $X^1$ is CH, $R^9$ is H and $R^8$ is $NH_2$. $R^1$ is H, $X^1$ is N, $R^9$ is H and $R^8$ is $NR^{11}R^{12}$. R is H, $X^1$ is N, $R^9$ is H and $R^8$ is $NH_2$. $R^1$ is $CH_3$, $X^1$ is N, $R^9$ is H and $R^8$ is $NR^{11}R^{12}$. $R^1$ is $CH_3$, $X^1$ is N, $R^9$ is H and $R^8$ is $NH_2$. $R^1$ is H, $X^1$ is CH, $R^9$ is $NR^{11}R^{12}$ and $R^8$ is $NR^{11}R^{12}$. $R^1$ is H, $X^1$ is CH, $R^9$ is $NR^{11}R^{12}$ and $R^8$ is $NH_2$. $R^1$ is $CH_3$, $X^1$ is CH, $R^9$ is $NR^{11}R^{12}$ and $R^8$ is $NR^{11}R^{12}$. $R^1$ is $CH_3$, $X^1$ is CH, $R^9$ is $NR^{11}R^{12}$ and $R^8$ is $NH_2$. $R^1$ is H, $X^1$ is N, $R^9$ is $NR^{11}R^{12}$ and $R^8$ is $NR^{11}R^{12}$. $R^1$ is H, $X^1$ is N, $R^9$ is $NR^{11}R^{12}$ and $R^8$ is $NH_2$. $R^1$ is $CH_3$, $X^1$ is N, $R^9$ is $NR^{11}R^{12}$ and $R^8$ is $NR^{11}R^{12}$. $R^1$ is $CH_3$, $X^1$ is N, $R^9$ is $NR^{11}R^{12}$ and $R^8$ is $NH_2$.

(l) $R^1$ is H, $X^1$ is CH, and $R^8$ and $R^9$ are independently $SR^{11}$. $R^1$ is $CH_3$, $X^1$ is CH, and $R^8$ and $R^9$ are independently $SR^{11}$. $R^1$ is H, $X^1$ is N, and $R^8$ and $R^9$ are independently $SR^{11}$. $R^1$ is $CH_3$, $X^1$ is N, and $R^8$ and $R^9$ are independently $SR^{11}$ In another embodiment, the compound of Formula VIb is a compound of Formula VIc

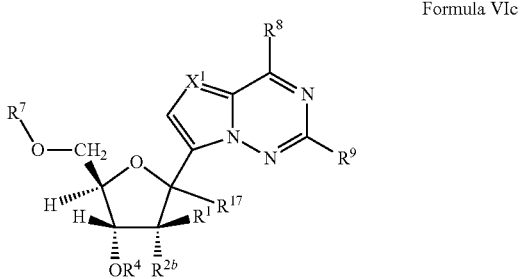

Formula VIc or an acceptable salt thereof,
wherein:
$R^{2b}$ is $OR^4$ or F;
each $R^4$ is independently $-CH_2R^6$ or $C(O)R^5$ wherein $R^5$ is phenyl or substituted phenyl;
$R^7$ is $Si(R^3)_3$, $C(O)R^5$ or $-C(R^5)_2R^6$ wherein each $R^5$ is independently H, phenyl, or substituted phenyl;

$R^6$ is phenyl or substituted phenyl; and
the remaining variables are defined as in Formula VI.

In one aspect of this embodiment, $R^{2b}$ is $OR^4$. In another aspect of this embodiment, $R^{2b}$ is F. In another aspect of this embodiment, $R^7$ is $-CH_2R^6$. In another aspect of this embodiment, $R^7$ is $C(O)R^5$ wherein $R^5$ is phenyl or substituted phenyl. In another aspect of this embodiment, $R^{2b}$ is F and each $R^4$ and $R^7$ is $C(O)R^5$ wherein each $R^5$ is independently phenyl or substituted phenyl. In another aspect of this embodiment, $R^{17}$ is OH. In another aspect of this embodiment, $R^{17}$ is $OR^{18}$. In another aspect of this embodiment, $R^{17}$ is $-OC(O)R^{18}$. In another aspect of this embodiment, $R^{17}$ is $-OC(O)CH_3$. In another aspect of this embodiment, $R^{17}$ is ethoxy or methoxy. In another aspect of this embodiment, $X^1$ is $C-R^{10}$. In another aspect of this embodiment, $X^1$ is $C-H$. In another aspect of this embodiment, $X^1$ is N. In another aspect of this embodiment, $R^1$ is H. In another aspect of this embodiment, $R^1$ is $CH_3$. In another aspect of this embodiment, $R^{17}$ is OH and $X^1$ is $C-R^{10}$. In another aspect of this embodiment, $R^{17}$ is $-OC(O)R^{18}$ and $X^1$ is $C-R^{10}$. In another aspect of this embodiment, $R^{17}$ is $-OC(O)CH_3$ and $X^1$ is $C-R^{10}$. In another aspect of this embodiment, $R^{17}$ is $OR^{18}$ and $X^1$ is $C-R^{10}$. In another aspect of this embodiment, $R^{17}$ is OH and $X^1$ is $C-H$. In another aspect of this embodiment, $R^{17}$ is $-OC(O)R^{18}$ and $X^1$ is $C-H$. In another aspect of this embodiment, $R^{17}$ is $-OC(O)CH_3$ and $X^1$ is $C-H$. In another aspect of this embodiment, $R^{17}$ is $OR^{18}$ and $X^1$ is $C-H$. In another aspect of this embodiment, $R^{17}$ is OH and $X^1$ is N. In another aspect of this embodiment, $R^{17}$ is $-OC(O)R^{18}$ and $X^1$ is N. In another aspect of this embodiment, $R^{17}$ is $-OC(O)CH_3$ and $X^1$ is N. In another aspect of this embodiment, $R^{17}$ is $OR^{18}$ and $X^1$ is N. In another aspect of this embodiment, $R^{17}$ is OH, $R^1$ is H, and $X^1$ is $C-R^{10}$. In another aspect of this embodiment, $R^{17}$ is $-OC(O)R^{18}$, $R^1$ is H and $X^1$ is $C-R^{10}$. In another aspect of this embodiment, $R^{17}$ is $-OC(O)CH_3$ $R^1$ is H and $X^1$ is $C-R^{10}$. In another aspect of this embodiment, $R^{17}$ is $OR^{18}$, $R^1$ is H and $X^1$ is $C-R^{10}$. In another aspect of this embodiment, $R^{17}$ is OH, $R^1$ is H and $X^1$ is $C-H$. In another aspect of this embodiment, $R^{17}$ is $-OC(O)R^{18}$, $R^1$ is H and $X^1$ is $C-H$. In another aspect of this embodiment, $R^{17}$ is $-OC(O)CH_3$, $R^1$ is H and $X^1$ is $C-H$. In another aspect of this embodiment, $R^{17}$ is $OR^{18}$, $R^1$ is H and $X^1$ is $C-H$. In another aspect of this embodiment, $R^{17}$ is OH, $R^1$ is H and $X^1$ is N. In another aspect of this embodiment, $R^{17}$ is $-OC(O)R^1$, $R^1$ is H and $X^1$ is N. In another aspect of this embodiment, $R^{17}$ is $-OC(O)CH_3$, $R^1$ is H and $X^1$ is N. In another aspect of this embodiment, $R^{17}$ is $OR^{18}$, $R^1$ is H and $X^1$ is N. In another aspect of this embodiment, $R^{17}$ is OH, $R^1$ is $CH_3$, and $X^1$ is $C-R^{10}$. In another aspect of this embodiment, $R^{17}$ is $-OC(O)R^{18}$, $R^1$ is $CH_3$ and $X^1$ is $C-R^{10}$. In another aspect of this embodiment, $R^{17}$ is $-OC(O)CH_3$ $R^1$ is $CH_3$ and $X^1$ is $C-R^{10}$. In another aspect of this embodiment, $R^{17}$ is $OR^{18}$, $R^1$ is $CH_3$ and $X^1$ is $C-R^{10}$. In another aspect of this embodiment, $R^{17}$ is OH, $R^1$ is $CH_3$ and $X^1$ is $C-H$. In another aspect of this embodiment, $R^{17}$ is $-OC(O)R^{18}$, $R^1$ is $CH_3$ and $X^1$ is $C-H$. In another aspect of this embodiment, $R^{17}$ is $-OC(O)CH_3$, $R^1$ is $CH_3$ and $X^1$ is $C-H$. In another aspect of this embodiment, $R^{17}$ is $OR^{18}$, $R^1$ is $CH_3$ and $X^1$ is $C-H$. In another aspect of this embodiment, $R^{17}$ is OH, $R^1$ is $CH_3$ and $X^1$ is N. In another aspect of this embodiment, $R^{17}$ is $-OC(O)R^{18}$, $R^1$ is $CH_3$ and $X^1$ is N. In another aspect of this embodiment, $R^{17}$ is $-OC(O)CH_3$, $R^1$ is $CH_3$ and $X^1$ is N. In another aspect of this embodiment, $R^{17}$ is $OR^{18}$, $R^1$ is $CH_3$ and $X^1$ is N.

In another embodiment, the compound of Formula VIb is a compound of Formula VId

Formula VId

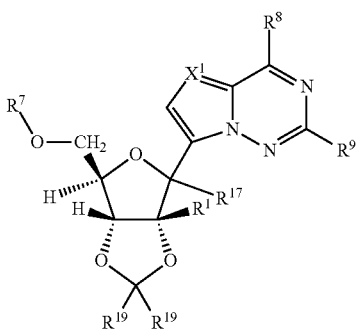

or an acceptable salt thereof,
wherein:
each $R^{19}$ is independently H, phenyl, substituted phenyl, or methyl and $R^7$ is —$C(R^5)_2R^6$, $Si(R^3)_3$, $C(O)R^5$, or

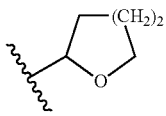

and the remaining variables are defined as in Formula VI. In one aspect of this embodiment, $R^7$ is $CH_2R^6$ wherein $R^6$ is phenyl or substituted phenyl. In one aspect of this embodiment, $R^7$ is $C(R^5)_2R^6$ wherein each $R^5$ or $R^6$ is independently phenyl or substituted phenyl. In one aspect of this embodiment, $R^7$ is $Si(R^3)_3$. In one aspect of this embodiment, $R^7$ is $Si(R^3)_2$(t-butyl) wherein each $R^3$ is independently phenyl or substituted phenyl. In one aspect of this embodiment, $R^7$ is $Si(R^3)_2$(t-butyl) wherein each $R^3$ is methyl. In one aspect of this embodiment, $R^7$ is $C(O)R^5$. In one aspect of this embodiment, $R^7$ is $C(O)CH_3$. In one aspect of this embodiment, $R^7$ is tetrahydro-2H-pyran-2-yl. In one aspect of this embodiment, each $R^{19}$ is $CH_3$. In one aspect of this embodiment, one of $R^{19}$ is H and the other of $R^{19}$ is phenyl or substituted phenyl. In one aspect of this embodiment, $R^7$ is $CH_2R^6$ wherein $R^6$ is phenyl or substituted phenyl each $R^{19}$ is $CH_3$. In one aspect of this embodiment, $R^7$ is $C(R^5)_2R^6$ wherein each $R^5$ or $R^6$ is independently phenyl or substituted phenyl and each $R^{19}$ is $CH_3$. In one aspect of this embodiment, $R^7$ is $Si(R^3)_3$ and each $R^{19}$ is $CH_3$. In one aspect of this embodiment, $R^7$ is $Si(R^3)_2$(t-butyl) wherein each $R^3$ is independently phenyl or substituted phenyl and each $R^{19}$ is $CH_3$. In one aspect of this embodiment, $R^7$ is $Si(R^3)_2$(t-butyl) wherein each $R^3$ is methyl and each $R^{19}$ is $CH_3$. In one aspect of this embodiment, $R^7$ is $C(O)R^5$ and each $R^{19}$ is $CH_3$. In one aspect of this embodiment, $R^7$ is $C(O)CH_3$ and each $R^{19}$ is $CH_3$. In one aspect of this embodiment, $R^7$ is tetrahydro-2H-pyran-2-yl and each $R^{19}$ is $CH_3$.

In another embodiment of Formula VId, $R^{17}$ is OH. In another embodiment of Formula VId, $R^{17}$ is —$OC(O)R^{18}$. In another embodiment of Formula VId, $R^{17}$ is —$OC(O)CH_3$. In another embodiment of Formula VId, $R^{17}$ is $OR^{18}$. In another aspect of this embodiment, $X^1$ is C—$R^{10}$. In another embodiment of Formula VId, $X^1$ is C—H. In another embodiment of Formula VId, $X^1$ is N. In another embodiment of Formula VId, $R^1$ is H. In another embodiment of Formula VId, $R^1$ is $CH_3$. In another embodiment of Formula VId, $R^{17}$ is OH and $X^1$ is C—$R^{10}$. In another embodiment of Formula VId, $R^{17}$ is —$OC(O)R^{18}$ and $X^1$ is C—$R^{10}$. In another embodiment of Formula VId, $R^{17}$ is —$OC(O)CH_3$ and $X^1$ is C—$R^{10}$. In another embodiment of Formula VId, $R^{17}$ is $OR^{18}$ and $X^1$ is C—$R^{10}$. In another embodiment of Formula VId, $R^{17}$ is OH and $X^1$ is C—H. In another embodiment of Formula VId, $R^{17}$ is —$OC(O)R^{18}$ and $X^1$ is C—H. In another embodiment of Formula VId, $R^{17}$ is —$OC(O)CH_3$ and $X^1$ is C—H. In another embodiment of Formula VId, $R^{17}$ is $OR^{18}$ and $X^1$ is C—H. In another embodiment of Formula VId, $R^{17}$ is OH and $X^1$ is N. In another embodiment of Formula VId, $R^{17}$ is —$OC(O)R^{18}$ and $X^1$ is N. In another embodiment of Formula VId, $R^{17}$ is —$OC(O)CH_3$ and $X^1$ is N. In another embodiment of Formula VId, $R^{17}$ is $OR^{18}$ and $X^1$ is N. In another embodiment of Formula VId, $R^{17}$ is OH, $R^1$ is H, and $X^1$ is C—$R^{10}$. In another embodiment of Formula VId, $R^{17}$ is —$OC(O)R^{18}$, $R^1$ is H and $X^1$ is C—$R^{10}$. In another embodiment of Formula VId, $R^{17}$ is —$OC(O)CH_3$ $R^1$ is H and $X^1$ is C—$R^{10}$. In another embodiment of Formula VId, $R^{17}$ is $OR^{18}$, $R^1$ is H and $X^1$ is C—$R^{10}$. In another embodiment of Formula VId, $R^{17}$ is OH, $R^1$ is H and $X^1$ is C—H. In another aspect of this embodiment, $R^{17}$ is —$OC(O)R^{18}$, $R^1$ is H and $X^1$ is C—H. In another embodiment of Formula VId, $R^{17}$ is —$OC(O)CH_3$, $R^1$ is H and $X^1$ is C—H. In another embodiment of Formula VId, $R^{17}$ is $OR^{18}$, $R^1$ is H and $X^1$ is C—H. In another embodiment of Formula VId, $R^1$ is H and $X^1$ is N. In another embodiment of Formula VId, $R^{17}$ is —$OC(O)R^{18}$, $R^1$ is H and $X^1$ is N. In another embodiment of Formula VId, $R^{17}$ is —$OC(O)CH_3$, $R^1$ is H and $X^1$ is N. In another embodiment of Formula VId, $R^{17}$ is $OR^{18}$, $R^1$ is H and $X^1$ is N. In another embodiment of Formula VId, $R^{17}$ is OH, $R^1$ is $CH_3$, and $X^1$ is C—$R^{10}$. In another embodiment of Formula VId, $R^{17}$ is —$OC(O)R^{18}$, $R^1$ is $CH_3$ and $X^1$ is C—$R^{10}$. In another embodiment of Formula VId, $R^{17}$ is —$OC(O)CH_3$ $R^1$ is $CH_3$ and $X^1$ is C—$R^{10}$. In another embodiment of Formula VId, $R^{17}$ is $OR^{18}$, $R^1$ is $CH_3$ and $X^1$ is C—$R^{10}$. In another embodiment of Formula VId, $R^{17}$ is OH, $R^1$ is $CH_3$ and $X^1$ is C—H. In another embodiment of Formula VId, $R^{17}$ is —$OC(O)R^{18}$, $R^1$ is $CH_3$ and $X^1$ is C—H. In another embodiment of Formula VId, $R^{17}$ is —$OC(O)CH_3$, $R^1$ is $CH_3$ and $X^1$ is C—H. In another embodiment of Formula VId, $R^{17}$ is $OR^{18}$, $R^1$ is $CH_3$ and $X^1$ is C—H. In another embodiment of Formula VId, $R^{17}$ is OH, $R^1$ is $CH_3$ and $X^1$ is N. In another embodiment of Formula VId, $R^{17}$ is —$OC(O)R^{18}$, $R^1$ is $CH_3$ and $X^1$ is N. In another embodiment of Formula VId, $R^{17}$ is —$OC(O)CH_3$, $R^1$ is $CH_3$ and $X^1$ is N. In another embodiment of Formula VId, $R^{17}$ is $OR^{18}$, $R^1$ is $CH_3$ and $X^1$ is N.

In another embodiment, the compound of Formula VIb is

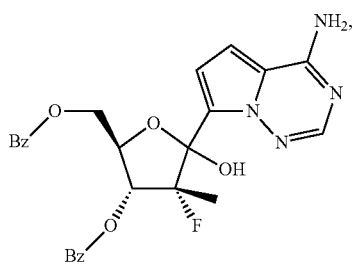

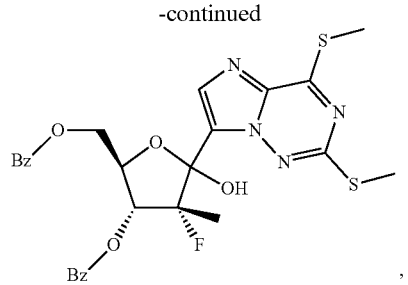
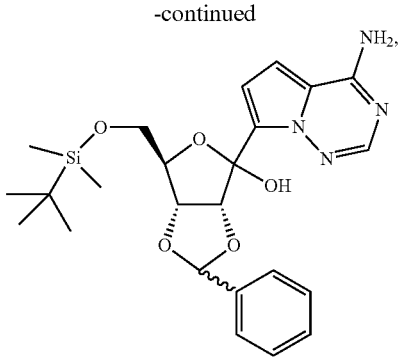
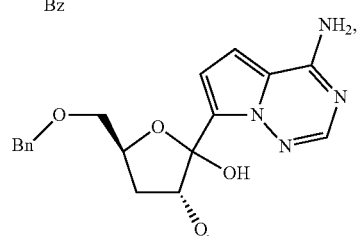
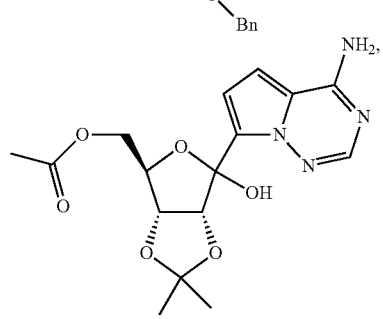
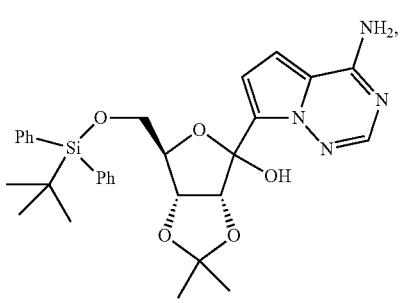
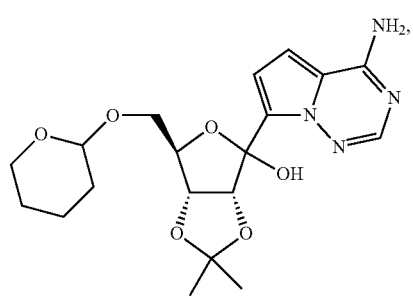
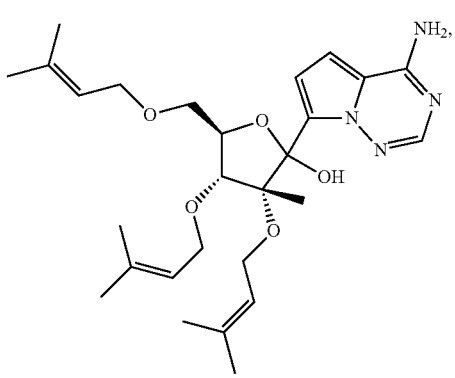
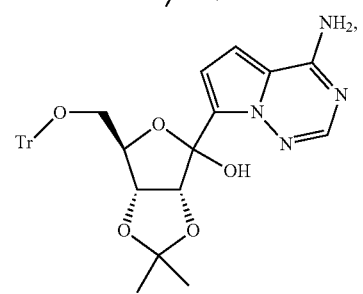
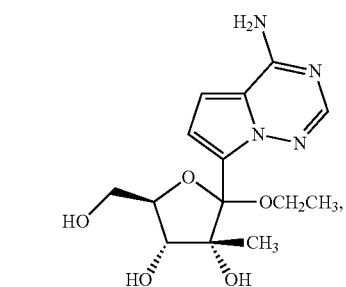
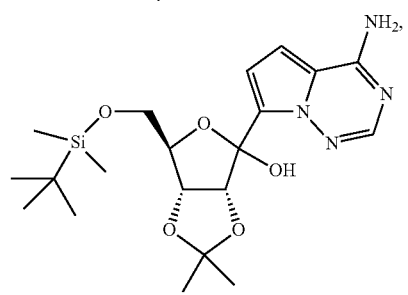
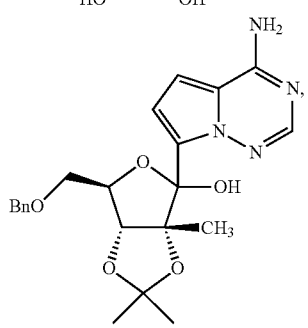

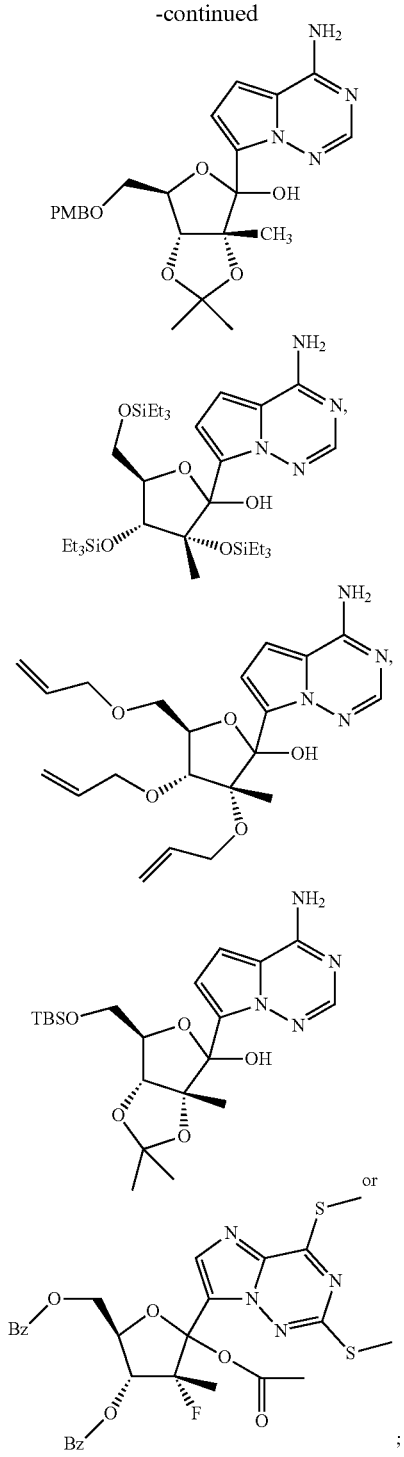

or an acceptable salt thereof.

Definitions

Unless stated otherwise, the following terms and phrases as used herein are intended to have the following meanings:

When trade names are used herein, applicants intend to independently include the tradename product and the active ingredient(s) of the tradename product.

As used herein, "a compound of the invention" or "a compound of Formula I" means a compound of Formula I or an acceptable salt, thereof. Similarly, with respect to isolatable intermediates, the phrase "a compound of Formula (number)" means a compound of that formula and an acceptable salts, thereof.

"Alkyl" is hydrocarbon containing normal, secondary, tertiary or cyclic carbon atoms. For example, an alkyl group can have 1 to 20 carbon atoms (i.e., $C_1$-$C_{20}$ alkyl), 1 to 8 carbon atoms (i.e., $C_1$-$C_8$ alkyl), or 1 to 6 carbon atoms (i.e., $C_1$-$C_6$ alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), and octyl (—$(CH_2)_7CH_3$).

"Alkoxy" means a group having the formula —O-alkyl, in which an alkyl group, as defined above, is attached to the parent molecule via an oxygen atom. The alkyl portion of an alkoxy group can have 1 to 20 carbon atoms (i.e., $C_1$-$C_{20}$ alkoxy), 1 to 12 carbon atoms (i.e., $C_1$-$C_{12}$ alkoxy), or 1 to 6 carbon atoms (i.e., $C_1$-$C_6$ alkoxy). Examples of suitable alkoxy groups include, but are not limited to, methoxy (—O—$CH_3$ or —OMe), ethoxy (—$OCH_2CH_3$ or —OEt), t-butoxy (—O—$C(CH_3)_3$ or —OtBu) and the like.

"Haloalkyl" is an alkyl group, as defined above, in which one or more hydrogen atoms of the alkyl group is replaced with a halogen atom. The alkyl portion of a haloalkyl group can have 1 to 20 carbon atoms (i.e., $C_1$-$C_{20}$ haloalkyl), 1 to 12 carbon atoms (i.e., $C_1$-$C_{12}$ haloalkyl), or 1 to 6 carbon atoms (i.e., $C_1$-$C_6$ alkyl). Examples of suitable haloalkyl groups include, but are not limited to, —$CF_3$, —$CHF_2$, —$CFH_2$, —$CH_2CF_3$, and the like. The term "haloalkyl" includes "polyfluoroalkyl". The term "polyfluoroalkyl" is an alkyl group, as defined above, in which two or more hydrogen atoms of the alkyl group is replaced with a fluorine atom.

"Alkenyl" is a hydrocarbon containing normal, secondary, tertiary or cyclic carbon atoms with at least one site of unsaturation, i.e. a carbon-carbon, $sp^2$ double bond. For example, an alkenyl group can have 2 to 20 carbon atoms (i.e., $C_2$-$C_{20}$ alkenyl), 2 to 8 carbon atoms (i.e., $C_2$-$C_8$ alkenyl), or 2 to 6 carbon atoms (i.e., $C_2$-$C_6$ alkenyl). Examples of suitable alkenyl groups include, but are not limited to, ethylene or vinyl (—CH=$CH_2$), allyl (—$CH_2$CH=$CH_2$), cyclopentenyl (—$C_5H_7$), and 5-hexenyl (—$CH_2CH_2CH_2CH_2$CH=$CH_2$).

"Alkynyl" is a hydrocarbon containing normal, secondary, tertiary or cyclic carbon atoms with at least one site of unsaturation, i.e. a carbon-carbon, sp triple bond. For example, an alkynyl group can have 2 to 20 carbon atoms (i.e., $C_2$-$C_{20}$ alkynyl), 2 to 8 carbon atoms (i.e., $C_2$-$C_8$ alkyne), or 2 to 6 carbon atoms (i.e., $C_2$-$C_6$ alkynyl).

Examples of suitable alkynyl groups include, but are not limited to, acetylenic (—C≡CH), propargyl (—CH$_2$C≡CH), and the like.

"Alkylene" refers to a saturated, branched or straight chain or cyclic hydrocarbon radical having two monovalent radical centers derived by the removal of two hydrogen atoms from the same or two different carbon atoms of a parent alkane. For example, an alkylene group can have 1 to 20 carbon atoms, 1 to 10 carbon atoms, or 1 to 6 carbon atoms. Typical alkylene radicals include, but are not limited to, methylene (—CH$_2$—), 1,1-ethyl (—CH(CH$_3$)—), 1,2-ethyl (—CH$_2$CH$_2$—), 1,1-propyl (—CH(CH$_2$CH$_3$)—), 1,2-propyl (—CH$_2$CH(CH$_3$)—), 1,3-propyl (—CH$_2$CH$_2$CH$_2$—), 1,4-butyl (—CH$_2$CH$_2$CH$_2$CH$_2$—), and the like.

"Alkenylene" refers to an unsaturated, branched or straight chain or cyclic hydrocarbon radical having two monovalent radical centers derived by the removal of two hydrogen atoms from the same or two different carbon atoms of a parent alkene.

For example, and alkenylene group can have 1 to 20 carbon atoms, 1 to 10 carbon atoms, or 1 to 6 carbon atoms. Typical alkenylene radicals include, but are not limited to, 1,2-ethylene (—CH═CH—).

"Alkynylene" refers to an unsaturated, branched or straight chain or cyclic hydrocarbon radical having two monovalent radical centers derived by the removal of two hydrogen atoms from the same or two different carbon atoms of a parent alkyne. For example, an alkynylene group can have 1 to 20 carbon atoms, 1 to 10 carbon atoms, or 1 to 6 carbon atoms. Typical alkynylene radicals include, but are not limited to, acetylene (—C≡C—), propargyl (—CH$_2$C≡C—), and 4-pentynyl (—CH$_2$CH$_2$CH$_2$C≡C—).

"Amino" refers generally to a nitrogen radical which can be considered a derivative of ammonia, having the formula —N(X)$_2$, where each "X" is independently H, substituted or unsubstituted alkyl, substituted or unsubstituted carbocyclyl, substituted or unsubstituted heterocyclyl, etc. The hybridization of the nitrogen is approximately sp$^3$. Nonlimiting types of amino include —NH$_2$, —N(alkyl)$_2$, —NH(alkyl), —N(carbocyclyl)$_2$, —NH(carbocyclyl), —N(heterocyclyl)$_2$, —NH(heterocyclyl), —N(aryl)$_2$, —NH(aryl), —N(alkyl)(aryl), —N(alkyl)(heterocyclyl), —N(carbocyclyl)(heterocyclyl), —N(aryl)(heteroaryl), —N(alkyl)(heteroaryl), etc. The term "alkylamino" refers to an amino group substituted with at least one alkyl group. Nonlimiting examples of amino groups include —NH$_2$, —NH(CH$_3$), —N(CH$_3$)$_2$, —NH(CH$_2$CH$_3$), —N(CH$_2$CH$_3$)$_2$, —NH(phenyl), —N(phenyl)$_2$, —NH(benzyl), —N(benzyl)$_2$, etc. Substituted alkylamino refers generally to alkylamino groups, as defined above, in which at least one substituted alkyl, as defined herein, is attached to the amino nitrogen atom. Non-limiting examples of substituted alkylamino includes —NH(alkylene-C(O)—OH), —NH(alkylene-C(O)—O-alkyl), —N(alkylene-C(O)—OH)$_2$, —N(alkylene-C(O)—O-alkyl)$_2$, etc.

"Aryl" means an aromatic hydrocarbon radical derived by the removal of one hydrogen atom from a single carbon atom of a parent aromatic ring system. For example, an aryl group can have 6 to 20 carbon atoms, 6 to 14 carbon atoms, or 6 to 10 carbon atoms. Typical aryl groups include, but are not limited to, radicals derived from benzene (e.g., phenyl), substituted benzene, naphthalene, anthracene, biphenyl, and the like.

"Arylalkyl" refers to an acyclic alkyl radical in which one of the hydrogen atoms bonded to a carbon atom, typically a terminal or sp$^3$ carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group can comprise 7 to 20 carbon atoms, e.g., the alkyl moiety is 1 to 6 carbon atoms and the aryl moiety is 6 to 14 carbon atoms.

"Arylalkenyl" refers to an acyclic alkenyl radical in which one of the hydrogen atoms bonded to a carbon atom, typically a terminal or sp$^3$ carbon atom, but also an sp$^2$ carbon atom, is replaced with an aryl radical. The aryl portion of the arylalkenyl can include, for example, any of the aryl groups disclosed herein, and the alkenyl portion of the arylalkenyl can include, for example, any of the alkenyl groups disclosed herein. The arylalkenyl group can comprise 8 to 20 carbon atoms, e.g., the alkenyl moiety is 2 to 6 carbon atoms and the aryl moiety is 6 to 14 carbon atoms.

"Arylalkynyl" refers to an acyclic alkynyl radical in which one of the hydrogen atoms bonded to a carbon atom, typically a terminal or sp$^3$ carbon atom, but also an sp carbon atom, is replaced with an aryl radical. The aryl portion of the arylalkynyl can include, for example, any of the aryl groups disclosed herein, and the alkynyl portion of the arylalkynyl can include, for example, any of the alkynyl groups disclosed herein. The arylalkynyl group can comprise 8 to 20 carbon atoms, e.g., the alkynyl moiety is 2 to 6 carbon atoms and the aryl moiety is 6 to 14 carbon atoms.

The term "substituted" in reference to alkyl, alkylene, aryl, arylalkyl, alkoxy, heterocyclyl, heteroaryl, carbocyclyl, etc., for example, "substituted alkyl", "substituted alkylene", "substituted aryl", "substituted arylalkyl", "substituted heterocyclyl", and "substituted carbocyclyl", unless otherwise indicated, means alkyl, alkylene, aryl, arylalkyl, heterocyclyl, carbocyclyl respectively, in which one or more hydrogen atoms are each independently replaced with a non-hydrogen substituent. Typical substituents include, but are not limited to, —X, —R$^b$, —O—, ═O, —OR$^b$, —SR$^b$, —S—, —NR$^b{}_2$, —N+R$^b{}_3$, ═NR$^b$, —CX$_3$, —CN, —OCN, —SCN, —N═C═O, —NCS, —NO, —NO$_2$, ═N$_2$, —N$_3$, —NHC(═O)R$^b$, —OC(═O)R$^b$, —NHC(═O)NR$^b{}_2$, —S(═O)$_2$—, —S(═O)$_2$OH, —S(═O)$_2$ R$^b$, —OS(═O)$_2$OR$^b$, —S(═O)$_2$NR$^b{}_2$, —S(═O)R$^b$, —OP(═O)(OR$^b$)$_2$, —P(═O)(OR$^b$)$_2$, —P(═O)(O—)$_2$, —P(═O)(OH)$_2$, —P(O)(OR$^b$)(O—), —C(═O)R$^b$, —C(═O)X, —C(S)R$^b$, —C(O)OR$^b$, —C(O)O—, —C(S)OR$^b$, —C(O)SR$^b$, —C(S)SR$^b$, —C(O)NR$^b{}_2$, —C(S)NR$^b{}_2$, —C(═NR$^b$)NR$^b{}_2$, where each X is independently a halogen: F, Cl, Br, or I; and each R$^b$ is independently H, alkyl, aryl, arylalkyl, a heterocycle, or a protecting group or prodrug moiety. Alkylene, alkenylene, and alkynylene groups may also be similarly substituted. Unless otherwise indicated, when the term "substituted" is used in conjunction with groups such as arylalkyl, which have two or more moieties capable of substitution, the substituents can be attached to the aryl moiety, the alkyl moiety, or both.

"Heterocycle" or "heterocyclyl" as used herein includes by way of example and not limitation those heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and *J. Am. Chem. Soc.* (1960) 82:5566. In one specific embodiment of the invention "heterocycle" includes a "carbocycle" as defined herein, wherein one or more (e.g. 1, 2, 3, or 4) carbon atoms have been replaced with a heteroatom (e.g. O, N, or S). The terms "heterocycle" or "heterocyclyl" includes saturated rings, partially unsaturated rings, and aromatic rings (i.e., heteroaromatic rings). Substituted heterocyclyls include, for example, heterocyclic rings substituted with any of the substituents disclosed herein including carbonyl groups. A non-limiting example of a carbonyl substituted heterocyclyl is:

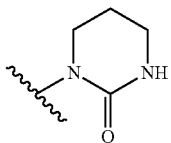 [SMILES: *N1CCCNC1=O]

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl:

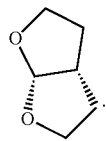

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Heteroaryl" refers to an aromatic heterocyclyl having at least one heteroatom in the ring. Non-limiting examples of suitable heteroatoms which can be included in the aromatic ring include oxygen, sulfur, and nitrogen. Non-limiting examples of heteroaryl rings include all of those aromatic rings listed in the definition of "heterocyclyl", including pyridinyl, pyrrolyl, oxazolyl, indolyl, isoindolyl, purinyl, furanyl, thienyl, benzofuranyl, benzothiophenyl, carbazolyl, imidazolyl, thiazolyl, isoxazolyl, pyrazolyl, isothiazolyl, quinolyl, isoquinolyl, pyridazyl, pyrimidyl, pyrazyl, etc.

"Carbocycle" or "carbocyclyl" refers to a saturated (i.e., cycloalkyl), partially unsaturated (e.g., cycloakenyl, cycloalkadienyl, etc.) or aromatic ring having 3 to 7 carbon atoms as a monocycle, 7 to 12 carbon atoms as a bicycle, and up to about 20 carbon atoms as a polycycle. Monocyclic carbocycles have 3 to 7 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system, or spiro-fused rings. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and phenyl. Non-limiting examples of bicyclo carbocycles includes naphthyl, tetrahydronapthalene, and decaline.

"Carbocyclylalkyl" refers to to an acyclic akyl radical in which one of the hydrogen atoms bonded to a carbon atom is replaced with a carbocyclyl radical as described herein. Typical, but non-limiting, examples of carbocyclylalkyl groups include cyclopropylmethyl, cyclopropylethyl, cyclobutylmethyl, cyclopentylmethyl and cyclohexylmethyl.

"Heteroarylalkyl" refers to an alkyl group, as defined herein, in which a hydrogen atom has been replaced with a heteroaryl group as defined herein. Non-limiting examples of heteroaryl alkyl include —CH$_2$-pyridinyl, —CH$_2$-pyrrolyl, —CH$_2$-oxazolyl, —CH$_2$-indolyl, —CH$_2$-isoindolyl, —CH$_2$-purinyl, —CH$_2$-furanyl, —CH$_2$-thienyl, —CH$_2$-benzofuranyl, —CH$_2$-benzothiophenyl, —CH$_2$-carbazolyl, —CH$_2$-imidazolyl, —CH$_2$-thiazolyl, —CH$_2$-isoxazolyl, —CH$_2$-pyrazolyl, —CH$_2$-isothiazolyl, —CH$_2$-quinolyl, —CH$_2$-isoquinolyl, —CH$_2$-pyridazyl, —CH$_2$-pyrimidyl, —CH$_2$-pyrazyl, —CH(CH$_3$)-pyridinyl, —CH(CH$_3$)-pyrrolyl, —CH(CH$_3$)-oxazolyl, —CH (CH$_3$)-indolyl, —CH (CH$_3$)-isoindolyl, —CH(CH$_3$)-purinyl, —CH(CH$_3$)-furanyl, —CH(CH$_3$)-thienyl, —CH(CH$_3$)-benzofuranyl, —CH (CH$_3$)-benzothiophenyl, —CH(CH$_3$)-carbazolyl —CH (CH$_3$)-imidazolyl, —CH(CH$_3$)-thiazolyl, —CH(CH$_3$)-isoxazolyl, —CH(CH$_3$)-pyrazolyl, —CH(CH$_3$)-isothiazolyl, —CH(CH$_3$)-quinolyl, —CH(CH$_3$)-isoquinolyl, —CH(CH$_3$)-pyridazyl, —CH(CH$_3$)-pyrimidyl, —CH (CH$_3$)-pyrazyl, etc.

The term "optionally substituted" in reference to a particular moiety of the compound of Formula I, Ib, Ic, II, IIb, IIc, III, IIIb, IIIc, IV, V, VI, or VIb-d (e.g., an optionally substituted aryl group) refers to a moiety wherein all substitutents are hydrogen or wherein one or more of the hydrogens of the moiety may be replaced by substituents such as those listed under the definition of "substituted" or as otherwise indicated.

The term "optionally replaced" in reference to a particular moiety of the compound of Formula I, Ib, Ic, II, IIb, IIc, III, IIIb, IIIc, IV, V, VI, or VIb-d (e.g., the carbon atoms of said ($C_1$-$C_8$)alkyl may be optionally replaced by —O—, —S—, or —$NR^a$—) means that one or more of the methylene groups of the ($C_1$-$C_8$)alkyl may be replaced by 0, 1, 2, or more of the groups specified (e.g., —O—, —S—, or —$NR^a$—).

The term "non-terminal carbon atom(s)" in reference to an alkyl, alkenyl, alkynyl, alkylene, alkenylene, or alkynylene moiety refers to the carbon atoms in the moiety that intervene between the first carbon atom of the moiety and the last carbon atom in the moiety. Therefore, by way of example and not limitation, in the alkyl moiety —$CH_2$(C*)$H_2$(C*)$H_2CH_3$ or alkylene moiety —$CH_2$(C*)$H_2$(C*)$H_2CH_2$— the C* atoms would be considered to be the non-terminal carbon atoms.

The term "transition metal" or "transition element" is defined following the nomenclature of the Interarational Union of Pure and Applied Chemistry in the *Compendium of Chemical Terminology*, Internet edition.

The term "lanthanide" means the elements La, Ce, Pr, Nd, Pm, Sm, Eu, Gd, Tb, Dy, Ho, Er, Tm, Yb and Lu.

The term "alkaline earth or alkaline earth metal" means the elements Be, Mg, Ca, Sr, Ba and Ra.

The transition metals, lanthanides, alkaline earth metals and other metals such as aluminum, gallium, indium, thallium, tin, lead or bismuth referred to herein may form salts with acidic compounds. For example, they may form salts of triflic acid ($CF_3SO_2OH$). Many of these metals can exist in multiple oxidation states and thus form more than one salt with acid compounds. When reference is made to a salt of a metal, all such oxidation states are contemplated as being included in this invention so long as they are stable oxidation states of the metal.

The term "treating", in reference to the method claims described herein, means combining the reagents described in the claim under conditions wherein a reaction occurs. A non-limiting example is "treating a compound of Formula IIIb with a compound of Formula IV" would mean combining the compound of Formula IIIb with a compound of Formula IV" under conditions wherein the two molecules would react. The ordering of the combining step, i.e., adding a compound of Formula IIIb to a compound of Formula IV or adding a compound of Formula IV to a compound of Formula IIIb, is dependent upon the substituents and stability of the respective compounds being combined. The choice of the order of combination would be well understood by one skilled in the art based on the knowledge imparted with the instant disclosure. Both orders of combining the reagents are encompassed by the instant invention.

Unless otherwise specified, the carbon atoms of the compounds of Formula I, Ib, Ic, II, IIb, IIc, III, IIIb, IIIc, IV, V, VI, or VIb-d are intended to have a valence of four. In some chemical structure representations where carbon atoms do not have a sufficient number of variables attached to produce a valence of four, the remaining carbon substituents needed to provide a valence of four should be assumed to be hydrogen. For example,

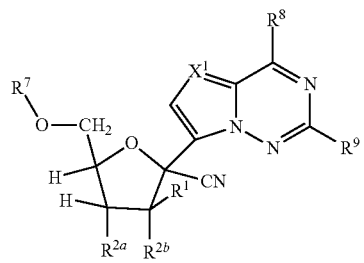

has the same meaning as

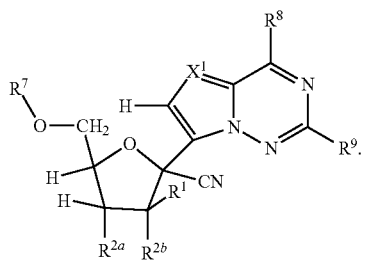

"Protecting group" refers to a moiety of a compound that masks or alters the properties of a functional group or the properties of the compound as a whole. The chemical substructure of a protecting group varies widely. One function of a protecting group is to serve as an intermediate in the synthesis of the parental drug substance. Chemical protecting groups and strategies for protection/deprotection are well known in the art. See: "Protective Groups in Organic Chemistry", Theodora W. Greene (John Wiley & Sons, Inc., New York, 1991. Protecting groups are often utilized to mask the reactivity of certain functional groups, to assist in the efficiency of desired chemical reactions, e.g. making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools.

It is to be noted that all enantiomers, diastereomers, and racemic mixtures, tautomers, polymorphs, pseudopolymorphs of compounds within the scope of Formula I, Ib, Ic, II, IIb, IIc, III, IIIb, IIIc, IV, V, VI, or VIb-d and acceptable salts thereof are embraced by the present invention. All mixtures of such enantiomers and diastereomers are within the scope of the present invention.

A compound of Formula I, Ib, Ic, II, IIb, IIc, III, IIIb, IIIc, IV, V, VI, or VIb-d and acceptable salts thereof may exist as different polymorphs or pseudopolymorphs. As used herein, crystalline polymorphism means the ability of a crystalline compound to exist in different crystal structures. The crystalline polymorphism may result from differences in crystal packing (packing polymorphism) or differences in packing between different conformers of the same molecule (conformational polymorphism). As used herein, crystalline pseudopolymorphism means the ability of a hydrate or solvate of a compound to exist in different crystal structures. The pseudopolymorphs of the instant invention may exist due to differences in crystal packing (packing pseudopolymorphism) or due to differences in packing between different conformers of the same molecule (conformational pseudopolymorphism). The instant invention comprises all polymorphs and pseudopolymorphs of the compounds of Formula I, Ib, Ic, II, IIb, IIc, III, IIIb, IIIc, IV, V, VI, or VIb-d and their acceptable salts.

A compound of Formula I, Ib, Ic, II, IIb, IIc, III, IIIb, IIIc, IV, V, VI, or VIb-d and acceptable salts thereof may also exist as an amorphous solid. As used herein, an amorphous solid is a solid in which there is no long-range order of the positions of the atoms in the solid. This definition applies as well when the crystal size is two nanometers or less. Additives, including solvents, may be used to create the amorphous forms of the instant invention. The instant invention comprises all amorphous forms of the compounds of Formula I, Ib, Ic, II, IIb, IIc, III, IIIb, IIIc, IV, V, VI, or VIb-d and their acceptable salts.

The modifier "about" used in connection with a quantity is inclusive of the stated value and has the meaning dictated by the context (e.g., includes the degree of error associated with measurement of the particular quantity).

The compounds of the invention, exemplified by Formula I, Ib, Ic, II, IIb, IIc, III, IIIb, IIIc, IV, V, VI, or VIb-d may have chiral centers, e.g. chiral carbon or phosphorus atoms. The compounds of the invention thus include racemic mixtures of all stereoisomers, including enantiomers, diastereomers, and atropisomers. In addition, the compounds of the invention include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures are separated into their individual, substantially optically pure isomers through well-known techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l, D and L, or (+) and (−) are employed to designate the sign of rotation of plane-polarized light by the compound, with S, (−), or l meaning that the compound is levorotatory while a compound prefixed with R, (+), or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The compounds of Formula I, Ib, Ic, II, IIb, IIc, VI, and VIb-d are nucleosides with an anomeric carbon atom at position 1 of the carbohydrate ring. A non-limiting example would be Formula VIb wherein the $R^{17}$ substituent is in the 1 position of the carbohydrate. Thus Formula VIb is actually a representation of at least two compounds of Formula VIb1 (β riboside) and VIb2 (α riboside) with respect to the anomeric carbon atom. It is intended that Formula I, Ib, II, IIb, VI, and VIb-d are inclusive of both anomeric carbon isomers.

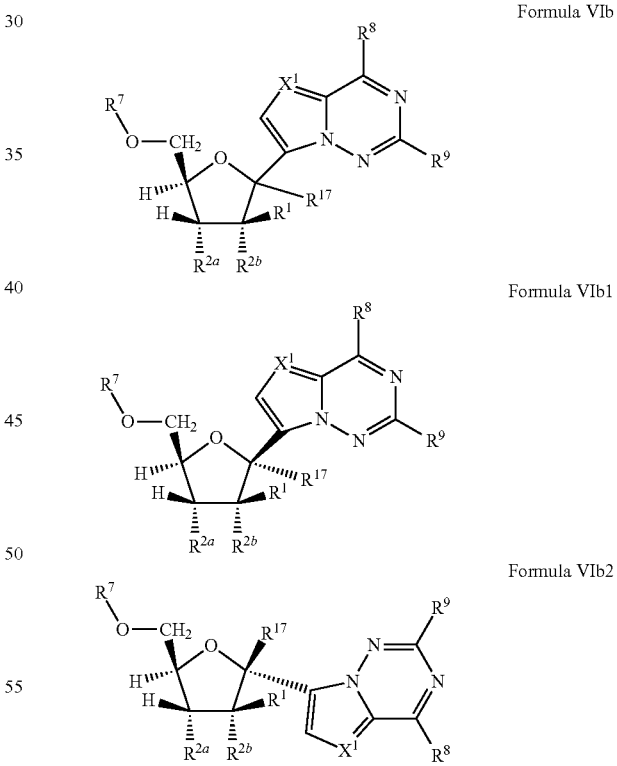

Formula VIb

Formula VIb1

Formula VIb2

The method of preparing a compound of Formula I, Ib or Ic from a compound of Formula II, IIb, or IIc, respectively, provides different ratios of the β riboside to α riboside depending upon the reaction conditions and particularly the Lewis acid used to promote the reaction. In preferred embodiments, the amount of β riboside exceeds the amount of α riboside. In one preferred embodiment, the ratio of β riboside to α riboside is at least about 3:1; in another preferred embodiment, the ratio is at least about 3.5:1; in another preferred embodiment, the ratio is at least about 4:1; in another preferred embodiment, the ratio is at least about 5:1; in another preferred embodiment, the ratio is at least about 6:1; in another preferred embodiment, the ratio is at least about 7:1; in another preferred embodiment, the ratio is at least about 8:1; and in a particular preferred embodiment, the ratio is at least 9:1 or more.

Whenever a compound described herein is substituted with more than one of the same designated group, e.g., "R" or "$R^1$", then it will be understood that the groups may be the same or different, i.e., each group is independently selected. Wavy lines, ～～～, indicate the site of covalent bond attachments to the adjoining substructures, groups, moieties, or atoms.

The compounds of the invention can also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

One skilled in the art will recognize that the pyrrolo[1,2-f][1,2,4]triazinyl and imidazo[1,2-f][1,2,4]triazinyl heterocycles can exist in tautomeric forms. For example, but not by way of limitation, structures (a) and (b) can have equivalent tautomeric forms as shown below:

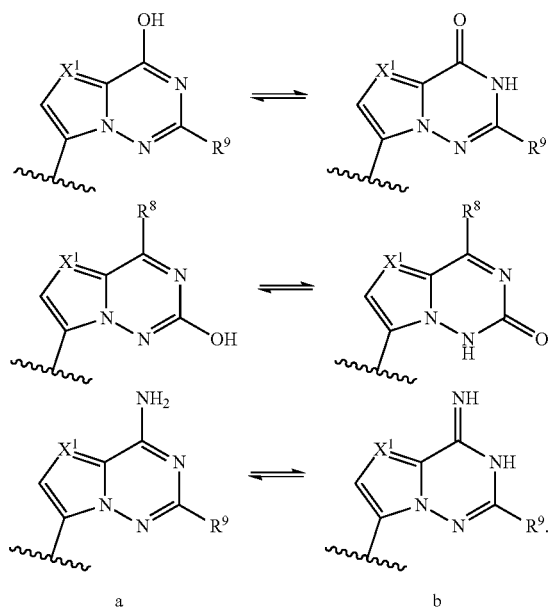

a    b

All possible tautomeric forms of the heterocycles in all of the embodiments disclosed herein are within the scope of the invention.

All publications, patents, and patent documents cited herein above are incorporated by reference herein, as though individually incorporated by reference.

Examples

Certain abbreviations and acronyms are used in describing the experimental details. Although most of these would be understood by one skilled in the art, Table 1 contains a list of many of these abbreviations and acronyms.

TABLE 1

List of abbreviations and acronyms.

| Abbreviation | Meaning |
| --- | --- |
| $Ac_2O$ | acetic anhydride |
| AIBN | 2,2'-azobis(2-methylpropionitrile) |
| Bn | unsubstituted benzyl |
| BnBr | benzylbromide |
| BSA | bis(trimethylsilyl)acetamide |
| Bz | benzoyl |
| BzCl | benzoyl chloride |
| CDI | carbonyl diimidazole |
| DABCO | 1,4-diazabicyclo[2.2.2]octane |
| DBN | 1,5-diazabicyclo[4.3.0]non-5-ene |
| DDQ | 2,3-dichloro-5,6-dicyano-1,4-benzoquinone |
| DBU | 1,5-diazabicyclo[5.4.0]undec-5-ene |
| DCA | dichloroacetamide |
| DCC | dicyclohexylcarbodiimide |
| DCM | dichloromethane |
| DMAP | 4-dimethylaminopyridine |
| DME | 1,2-dimethoxyethane |
| DMTCl | dimethoxytrityl chloride |
| DMSO | dimethylsulfoxide |
| DMTr | 4,4'-dimethoxytrityl |
| DMF | dimethylformamide |
| EtOAc | ethyl acetate |
| ESI | electrospray ionization |
| HMDS | hexamethyldisilazane |
| HPLC | High pressure liquid chromatography |
| LDA | lithium diisopropylamide |
| LRMS | low resolution mass spectrum |
| MCPBA | meta-chloroperbenzoic acid |
| MeCN | acetonitrile |
| MeOH | methanol |
| MMTC | mono methoxytrityl chloride |
| m/z or m/e | mass to charge ratio |
| $MH^+$ | mass plus 1 |
| $MH^-$ | mass minus 1 |
| MsOH | methanesulfonic acid |
| MS or ms | mass spectrum |
| NBS | N-bromosuccinimide |
| PMB | para-methoxybenzyl |
| Ph | phenyl |
| rt or r.t. | room temperature |
| TBAF | tetrabutylammonium fluoride |
| TMSCl | chlorotrimethylsilane |
| TMSBr | bromotrimethylsilane |
| TMSI | iodotrimethylsilane |
| TMSOTf | (trimethylsilyl)trifluoromethylsulfonate |
| TEA | triethylamine |
| TBA | tributylamine |
| TBAP | tributylammonium pyrophosphate |
| TBSCl | t-butyldimethylsilyl chloride |
| TEAB | triethylammonium bicarbonate |
| TFA | trifluoroacetic acid |
| TLC or tlc | thin layer chromatography |
| Tr | triphenylmethyl |
| Tol | 4-methylbenzoyl |
| Turbo Grignard | 1:1 mixture of isopropylmagnesium chloride and lithium chloride |
| δ | parts per million down field from tetramethylsilane |

Compound 1c

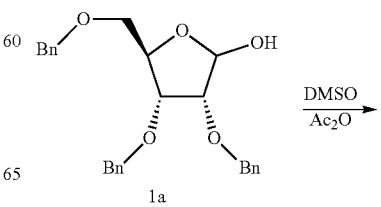

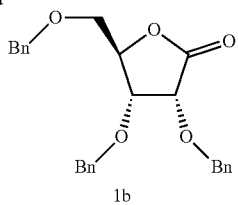

1b

Compound 1a (prepared according to J. Org. Chem., 1961, 26, 4605; 10.0 g, 23.8 mmol) was dissolved in anhydrous DMSO (30 mL) and placed under nitrogen. Acetic anhydride (20 mL) was added, and the mixture was stirred for 48 h at room temperature. When the reaction was complete by LC/MS, it was poured onto 500 mL ice water and stirred for 20 min. The aqueous layer was extracted with ethyl acetate (3×200 mL). The organic extracts were combined and washed with water (3×200 mL). The aqueous layers were discarded and the organic was dried over anhydrous MgSO$_4$ and evaporated to dryness. The residue was taken up in DCM and loaded onto a silica gel column. The final product 1b was purified by elution with 25% EtOAc/hexanes; 96% yield. $^1$H-NMR (CD$_3$CN): δ □□3.63-3.75 (m, 2H), 4.27 (d, 1H), 4.50-4.57 (m, 3H), 4.65 (s, 3H), 4.69-4.80 (m, 2H), 7.25 (d, 2H), 7.39 (m, 13H).

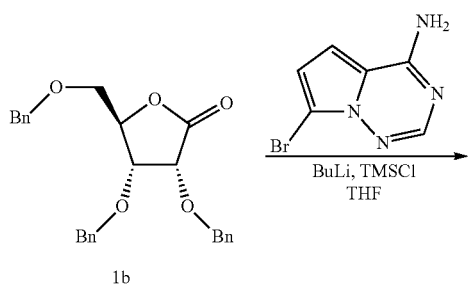

1b

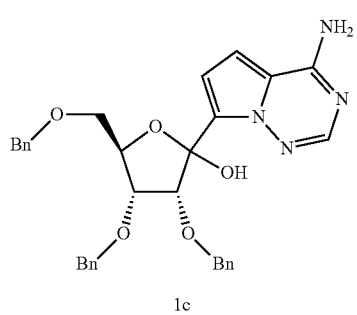

1c

7-Bromo-pyrrolo[2,1-f][1,2,4]triazin-4-ylamine (prepared according to WO2007/056170, 0.5 g, 2.4 mmol) was suspended in anhydrous THF (10 mL). Under nitrogen with stirring, TMSCl (0.668 mL, 5.28 mml) was added and the mixture was stirred for 20 min. at room temperature. The reaction was then cooled to −78° C. and a solution of BuLi (6.0 mL, 1.6 M in hexanes) was added slowly. The reaction was stirred for 10 min. at −78° C. and then a solution of the lactone 1b (1.0 g, 2.4 mmol in THF) was added via syringe. When the reaction was complete by LC/MS, acetic acid (0.5 mL) was added to quench the reaction. Solvents were removed by rotary evaporation and the residue was taken up in a mixture of 50:50 dichloromethane/water (100 mL). The organic layer was collected and washed with 50 mL additional water, dried over anhydrous MgSO$_4$ and filtered. Evaporation and purification by column chromatography (0-50% EtOAc: hexanes) provided a 1:1 mixture of anomers ic; 25% yield. LC/MS (m/z: 553, M+H+).

Compound 2c

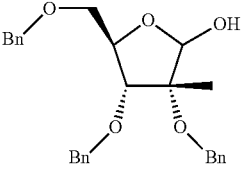

2a

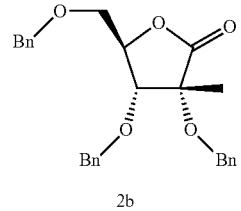

2b

To a dry, argon purged round bottom flask (100 mL) were added anhydrous DMSO (6 mL) and anhydrous acetic anhydride (4 mL, 42.4 mmol). Compound 2a (1.0 g, 2.3 mmol) was then added and the reaction mixture was allowed to stir at room temperature until complete disappearance of the starting material. After 17 h, the flask was placed into an ice bath and sat. NaHCO$_3$ (6 mL) was added to neutralize the reaction mixture. The organic material was then extracted using EtOAc (3×10 mL) and the combined organic layers were dried using MgSO$_4$. The solvent was removed under reduced pressure and the crude material was purified using flash silica gel chromatography (hexanes/EtOAc). 955 mg (96%) of the desired material 2b was isolated. LC/MS=433.2 (M+H$^+$). $^1$H NMR (300 MHz, CDCl$_3$): δ 7.33 (m, 15H), 4.80 (d, 1H), 4.64 (m, 6H), 4.06 (d, 1H), 3.79 (dd, 1H), 3.64 (dd, 1H), 1.54 (s, 3H).

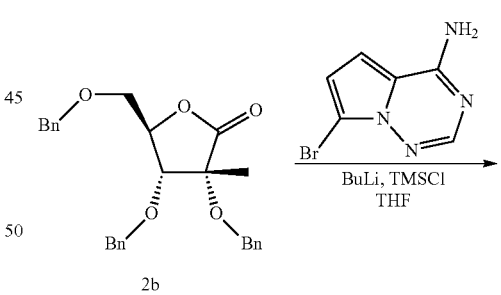

2b

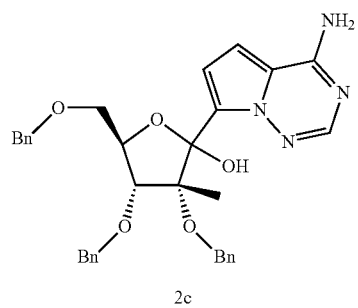

2c

To a dry, argon purged round bottom flask (100 mL) were added 7-bromo-pyrrolo[2,1-f][1,2,4]triazin-4-ylamine (234 mg, 1.10 mmol) and anhydrous THF (1.5 mL). TMSCl (276 µL, 2.2 mmol) was then added and the reaction mixture stirred for 2 h. The flask was placed into a dry ice/acetone bath (~–78° C.) and BuLi (2.5 mL, 4.0 mmol, 1.6 M in hexanes) was added dropwise. After 1 h, a solution of 2b (432 mg, 1.0 mmol) in THF was cooled to 0° C. and then added to the reaction flask dropwise. 5 After 1 h of stirring at −78° C., the flask was warmed to 0° C. and sat. NH$_4$Cl (5 mL) was added to quench the reaction. The organics were extracted using EtOAc (3×10 mL) and the combined organic layers were dried using MgSO$_4$. The solvent was removed under reduced pressure and the crude material was purified using flash silica gel chromatography (hexanes/EtOAc). 560 mg (90%) of the desired material 2c was isolated. LC/MS=567.2 (M+H+). $^1$H NMR (300 MHz, CDCl$_3$): δ 7.85 (m, 1H), 7.27 (m, 15H), 7.01 (m, 1H), 6.51 (m, 1H), 4.66 (m, 8H), 4.40 (m, 2H), 3.79 (m, 3H), 1.62 (s, 2'-CH$_3$ from the one anomer), 1.18 (s, 2'-CH$_3$ from the other anomer).

Alternative Procedures for 2c

To a dry, argon purged round bottom flask were added 7-bromo-pyrrolo[2,1-f][1,2,4]triazin-4-ylamine (9.6 g, 45 mmol) and anhydrous THF (60 mL). TMSCl (12.4 mL, 99 mmol) was then added and the reaction mixture stirred for 2 h. The flask was placed into a dry ice/acetone bath (~–78° C.) and BuLi (98 mL, 158 mmol, 1.6M in hexanes) was added dropwise. After 1 h, this reaction mixture was added to a solution of 2b (13.0 g, 30 mmol) in THF at −78° C. via cannula. After 2 h of stirring at −78° C., the flask was warmed to 0° C. Saturated NH$_4$Cl (150 mL) was added to quench the reaction. The organics were extracted using EtOAc (3×100 mL) and the combined organic layers were dried using MgSO$_4$. The solvent was removed under reduced pressure and the crude material was purified using flash silica gel chromatography (hexanes/EtOAc). 7.5 g (44%) of the desired material 2c was isolated. LC/MS=567.2 (M+H+).

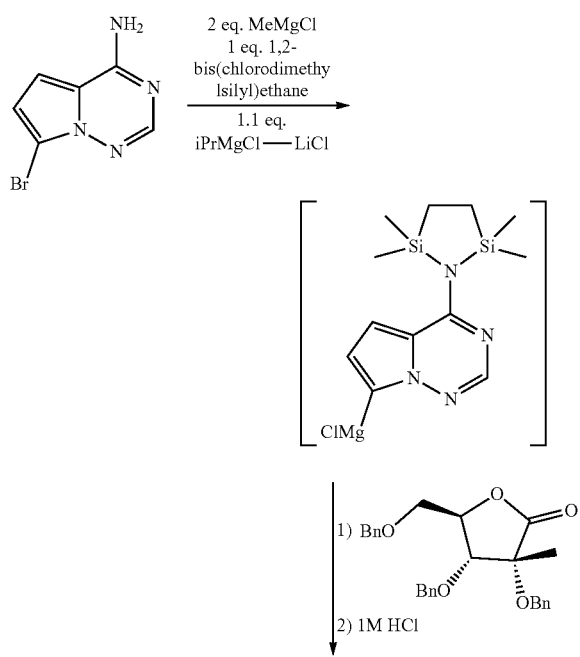

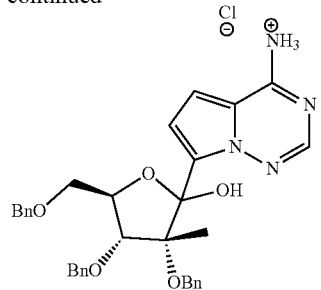

To a 500 ml jacketed 3-necked flask fitted with a thermocouple, vacuum/N$_2$ inlet and overhead stirring apparatus was added 7-bromo-pyrrolo[2,1-f][1,2,4]triazin-4-ylamine (20 g, 1.0 equiv., 94 mmol). This was suspended in dry THF (200 ml) and cooled to 0° C. To this was added dropwise 31 ml of MeMgCl solution (3M in THF, 1.0 equiv.). This proceeded with bubbling and a significant exotherm. The rate of addition was controlled to maintain internal temperature below 10° C. Following completion of addition and cooling to 0° C., 1,2-bis(chlorodimethylsilyl)ethane (20.2 g, 1.0 equiv.) was added in a single portion, with exotherm to about 5° C. Once the temperature had returned to 0° C., a second portion of 31 ml MeMgCl (3M in THF, 1.0 equiv.) was added as before. Once the temperature returned to 0° C., 80 ml of iPrMgCl.LiCl solution (1.3 M in THF, 1.1 equiv.) was added. The resulting dark solution was allowed to warm to room temperature, and conversion was checked by HPLC, with sample preparation in MeOH to provide the des-bromo heterocycle. Once the conversion of 7-bromo-pyrrolo[2,1-f][1,2,4]triazin-4-ylamine was >95% complete (5 hrs), the solution was cooled to 0° C., and a solution of 2b (40.6 g, 94 mmol) in 100 ml THF was added via canulla. The resulting orange solution was allowed to warm to room temperature and stirred overnight. After 12 hrs, the reaction was found to be complete by HPLC (sample prepared in H$_2$O/MeCN 1:1). At this point 200 ml of 13% NH$_4$Cl solution was added and briskly stirred for 15 min. After this time, agitation was ceased, and the two layers were allowed to separate. The organic layer was then reduced to roughly 70 ml, and MeCN (100 ml) was added, followed by 300 ml 1M aqueous HCl solution. The resulting slurry was stirred at room temperature for 2 hrs, then filtered through a sintered glass funnel. The resulting solid was dried overnight under vacuum at 45° C. to give 2c. Yield 37.6 g (66%)

To a suspension of 7-bromo-pyrrolo[2,1-f][1,2,4]triazin-4-ylamine (2.14 g, 10 mmol) in 0.5 M LiCl solution of anhydrous THF (20 mL) was added TMSCl (2.53 mL, 20 mmol) and stirred at room temperature for 2 h. After cooling to −20° C., 3.0 M methyl magnesium chloride in diethyl ether (6.67 mL) was added dropwise while stirring. The mixture was then allowed to warm to room temperature over a period of 1 h. After cooling back to −20° C., Turbo Grignard (1.3 M in THF) was added in portions until the magnesium-bromine exchange was nearly complete (~15.5 mL over a period of 2 h). A solution of 2b (5.2 g, 12 mmol) was then added. The resulting mixture was allowed to warm to room temperature. The reaction was quenched with methanol, affording 2c.

Compound 3a and 3b

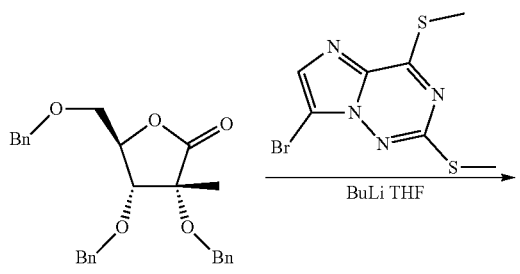

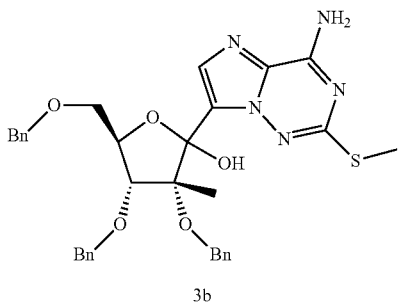

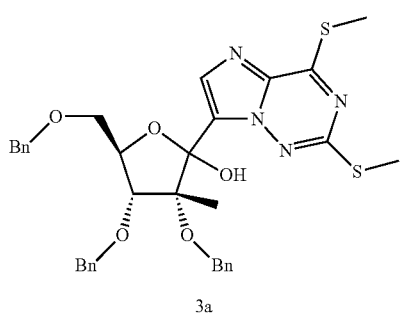

To a suspension of 7-bromo-2,4-bis-methylsulfanyl-imidazo[2,1-f][1,2,4]triazine (prepared according to WO2008116064, 600 mg, 2.06 mmol) in anhydrous THF (6 mL) was dropwise added BuLi (1.6 M in hexanes, 1.75 mL, 2.81 mmol) at −78° C. The suspension became red brown solution after 5 min, and then a solution of 2b (810 mg, 1.87 mmol) in THF (0.6 mL) was added dropwise to the mixture. The mixture was then allowed to warm up to room temperature. After 30 min, saturated NH$_4$Cl was added to quench the reaction. The mixture was diluted with ethyl acetate; the organic layer was washed with brine and concentrated in vacuo. The residue was purified by silica gel column chromatography (~40% EtOAc/hexanes), affording 3a as an isomeric mixture (0.77 g, 64%). MS=645.2 (M+H$^+$).

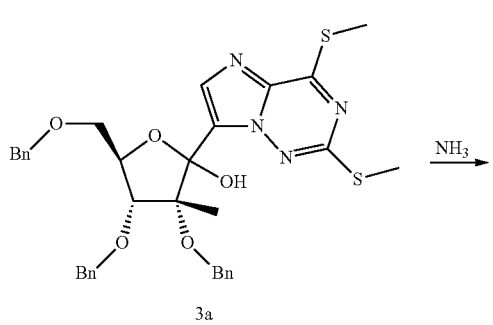

Compound 3a (2.0 g, 3.10 mmol) was transferred to a steel bomb reactor, and cooled at −78° C. Liquid ammonia (~20 mL) was collected at −78° C. and added to the bomb reactor. The bomb reactor was tightly sealed and warmed up to room temperature. The mixture was then heated at 50° C. for 20 h. Complete conversion occurred. After the ammonia gas was vented, the residue was purified by silica gel column chromatography (EtOAc/hexanes), affording the product 3b as a pale yellow solid (1.78 g, 94%). MS=614.3 (M+H$^+$).

Compound 4

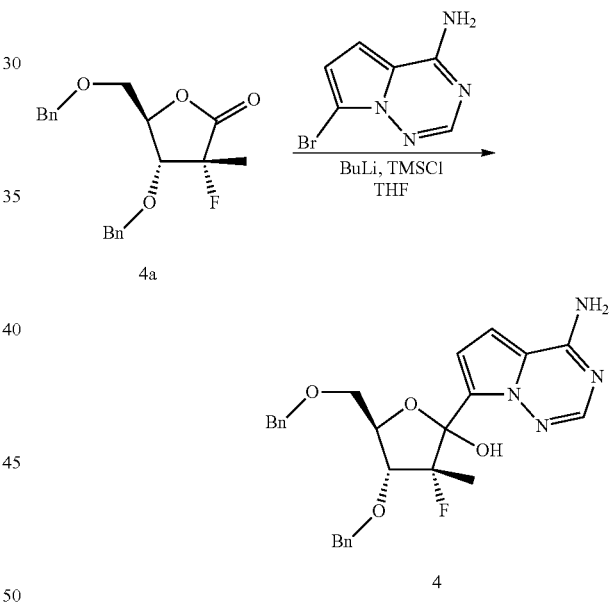

To a suspension of 7-bromo-pyrrolo[2,1-f][1,2,4]triazin-4-ylamine (2.13 g, 10 mmol) in THF (20 mL) was added TMSCl (2.66 mL, 21 mmol) and stirred at room temperature for 16 h under argon. After cooling to −78° C., a solution of BuLi (1.6 M, 21 mL, 33 mmol) in hexanes was added dropwise. The mixture was stirred for 1 h at the same temperature. A solution of 4a (prepared according to WO 200631725, 4.46 g, 12 mmol) in THF (10 mL) was then added. After stirring for 2 h at −78° C., saturated ammonium chloride was added to quench the reaction. The mixture was extracted with ethyl acetate. The organic extract was concentrated in vacuo. The residue was purified by silica gel chromatography (ethyl acetate/hexanes), affording 4 as a yellow solid (1.6 g, 32%). MS=507.1 (M+H+).

Alternative Procedure for Compound 4 Using 1,2-Bis-[(Chlorodimethyl)Silanyl]Ethane Instead of Chlorotrimethylsilane To a suspension of 7-bromo-pyrrolo[2,1-f][1,2,4]triazin-4-ylamine (500 mg, 2.35 mmol) in THF (6.5 mL) was added BuLi (1.6 M in hexanes, 1.6 mL) at −78° C. After 30 min., a solution of 1,2-bis-[(chlorodimethyl)silanyl]ethane (538 mg, 2.4 mmol) in THF (1.2 mL) was added. After 45 min., BuLi (1.6 mL) was added. After an additional 30 min., BuLi (1.5 mL) was added. After 30 min., a solution of 4a (610 mg, 1.64 mmol) in THF (2 mL) was then added dropwise. The resulting mixture was stirred at −78° C. for 2 h under argon. Acetic acid (0.7 mL) was added dropwise to quench the reaction, followed by addition of saturated ammonium chloride. The mixture was extracted with ethyl acetate. The organic extract was concentrated in vacuo. The residue was purified by silica gel chromatography (ethyl acetate/hexanes), affording 4 (320 mg, 40%). The starting 4a was also recovered (350 mg) from the chromatography.

Compound 5

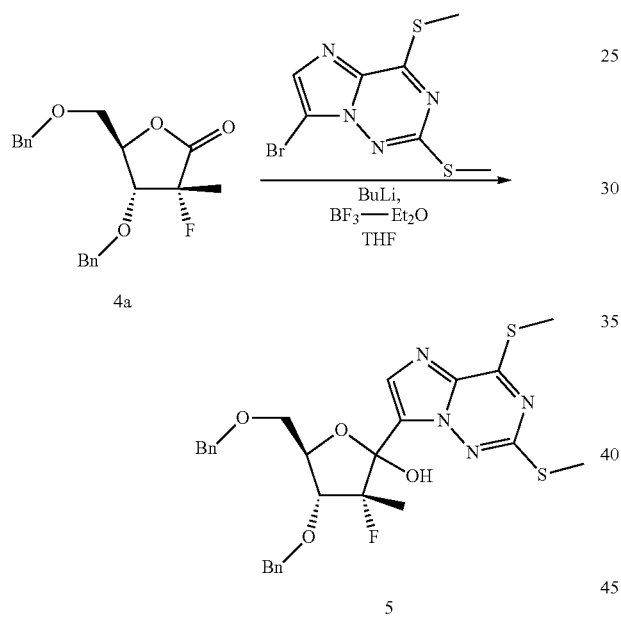

To a suspension of 7-bromo-2,4-bis-methylsulfanyl-imidazo[2,1-f][1,2,4]triazine (prepared according to WO2008116064, 500 mg, 1.72 mmol) in anhydrous THF (5 mL) was dropwise added BuLi (1.6 M in hexanes, 1.61 mL, 2.41 mmol) at −78 OC. The suspension became red brown solution after 5 min, and then a mixture of 4a (675 mg, 1.81 mmol) and boron trifluoride etherate (2.40 mL, 1.89 mmol) in THF (5 mL) was added dropwise to the mixture. After stirring for 2 h at −78° C., saturated NH$_4$Cl was added to quench the reaction. The mixture was diluted with ethyl acetate; the organic layer was washed with brine and concentrated in vacuo. The residue was purified by silica gel column chromatography (EtOAc/hexanes), affording 5 as a rich yellow foam (650 mg, 67%). $^1$H NMR (400 MHz, CDCl$_3$): δ 8.13 (d, 2H), 8.03 (d, 2H), 7.81 (d, 1H), 7.59 (t, 1H), 7.45 (m, 3H), 7.36 (t, 2H), 6.40 (brs, 1H), 6.01 (dd, 1H), 4.78 (m, 2H), 4.60 (dd, 1H), 2.68 (s, 3H), 2.45 (s, 3H), 1.62 (d, 3H). $^{19}$F NMR (376 MHz, CDCl$_3$): δ −167.5. MS=585.1 (M+H+).

Compound 6

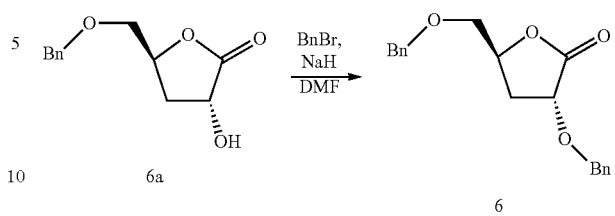

To a suspension of sodium hydride (about 60% suspension in oil, 400 mg, 10 mmol) in DMF (about 20 mL) is added dropwise a solution of 6a (prepared according to *J. Chem. Soc., Perkin Trans* 1, 1991, 490, about 2.2 g, 10 mmol) in DMF (10 mL) at about 0° C. The mixture is then stirred at about room temperature until the gas evolution ceases. Benzyl bromide (about 1 eq.) is added and the mixture is stirred for about 1 to 16 h at about 0 to 100° C. The mixture is poured into ice-water (300 mL) and extracted with ethyl acetate. The organic extract may be purified by silica gel chromatography to give 6.

Compound 7

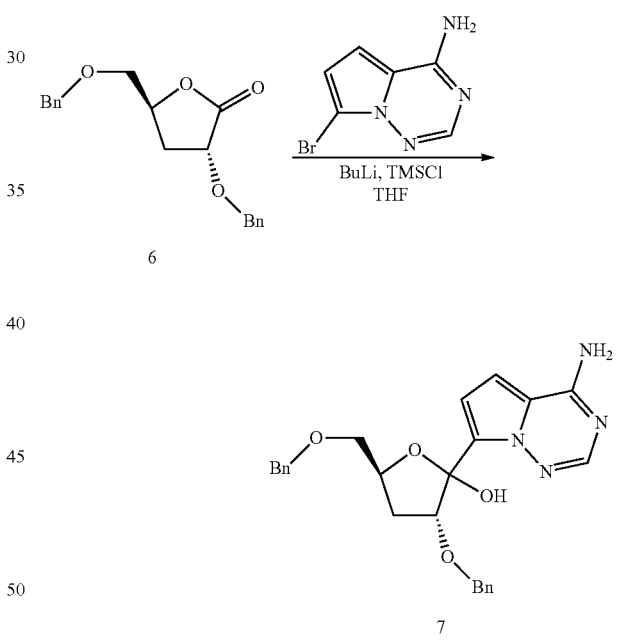

To a suspension of 7-bromo-pyrrolo[2,1-f][1,2,4]triazin-4-ylamine (about 10 mmol) in THF (about 20 mL) is added TMSCl (about 21 mmol) and the mixture is stirred at about room temperature for about 1 to 16 h under argon. After cooling to about −78° C., a solution of BuLi (about 1.6 M in hexanes, about 33 mmol) is added dropwise. The mixture is stirred for about ito 5 h at about the same temperature. A solution of 6 (about 12 mmol) in THF (about 10 mL) is then added. After stirring for about 2 h at about −78° C., saturated ammonium chloride is added to quench the reaction. The mixture is extracted with ethyl acetate. The organic extract is concentrated in vacuo. The residue may be purified by silica gel chromatography (ethyl acetate/hexanes), to give 7.

Lactone B

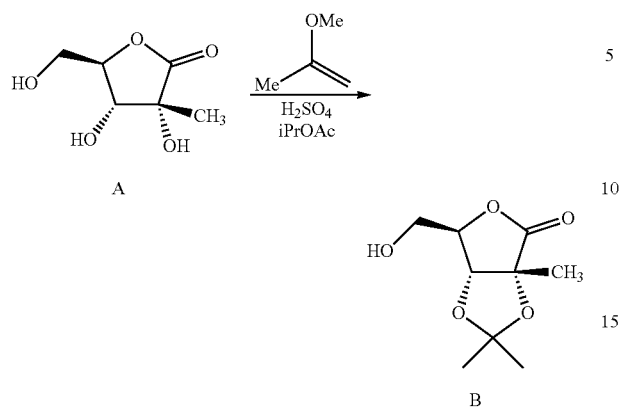

Lactone D

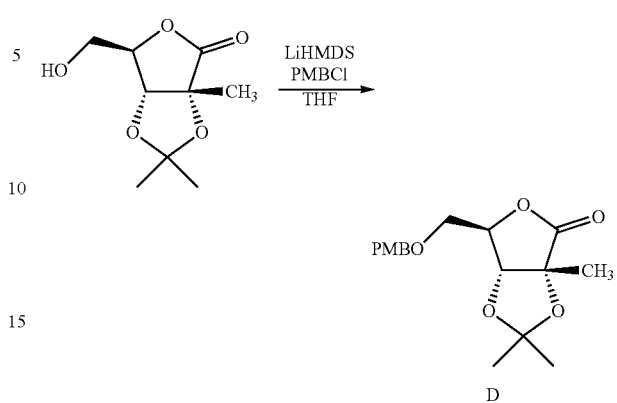

20.0 g lactone A (123.4 mmol) is suspended in 200 mL iPrOAc and to this mixture is added 65 μL H₂SO₄ (1.23 mmol, 0.01 equiv.). This mixture is cooled to 15° C. To the cooled mixture is added 11.8 mL 2-methoxypropene (123.4 mmol, 1.0 equiv.) over a period of 2 h. Upon completion of addition the mixture is allowed to stir for 12 h at 15° C. Following age, the mixture is warmed to 20° C. and another 6.0 mL 2-methoxypropene (0.5 equiv) is added to the reaction mixture. The mixture is aged with stirring at 20° C. for an additional 7 h. Following age, The solids are removed by filtration, rinsed with 100 mL iPrOAc. The combined organic washes are washed 1× with 100 mL water, and the organic layer is concentrated to a colorless oil. This oil is diluted with 100 mL heptane, and upon concentration affords colorless solids, which are collected by filtration, and rinsed with 100 mL heptane giving 8.36 g (36% yield) of desired compound, (M+H)/Z=203.

Lactone C

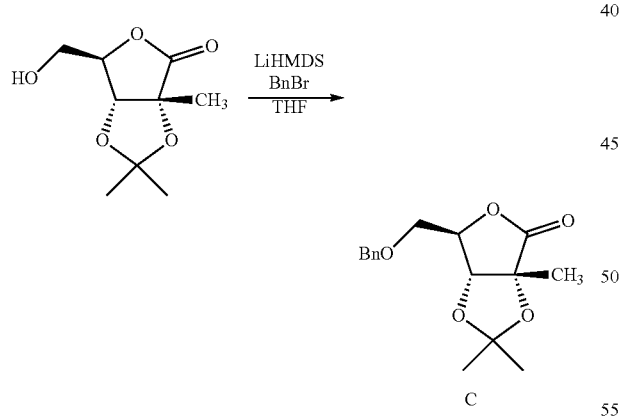

0.50 g lactone acetonide B (2.47 mmol), 0.294 mL benzyl bromide (2.47 mmol, 1.0 equiv.) and 5.0 mL tetrahydrofuran are combined and the mixture is cooled to 0° C. To the cooled mixture is added 2.47 mL of a 1.0 M LiHMDS in THF solution (2.47 mmol, 1.0 equiv.) over a period of 2.0 h. The mixture is allowed to slowly warm to 22° C., and is aged with stirring over 16 h. Following age, to the mixture is added 5.0 mL water, and the layers are split. The organic layer is concentrated, and the oil is purified by SiO₂ chromatography (0→40% EtOAc/Hexanes) affording 88.4 mg desired product as a colorless oil, (M+H)/Z=293.

0.50 g lactone acetonide B (2.47 mmol), 0.335 mL PMBBr (2.47 mmol, 1.0 equiv.) and 5.0 mL tetrahydrofuran are combined and the mixture is cooled to 0° C. To the cooled mixture is added 2.0 mL of a 1.0 M LiHMDS in THF solution (2.0 mmol, 0.8 equiv.) over a period of 2.0 h. The mixture is allowed to slowly warm to 22° C., and is aged with stirring over 16 h. Following age, the mixture is cooled to 0 C and to the cooled mixture is added the remaining 0.5 mL 1.0 M LiHMDS/THF solution (0.2 equiv.) over a period of 40 min. Following completion of base addition, the mixture is warmed to 23 C and aged for 1 h with stirring. Following age, the mixture is cooled to 0° C., and to the cooled mixture is added 0.6 mL 4 N sulfuric acid solution, followed by 0.6 mL water, and the resulting layers are separated (aq. pH 9). The combined organic washes are concentrated to a colorless oil, and the oil is purified by SiO₂ chromatography (0→40% EtOAc/Hexanes) affording 23.4 mg desired product D as a colorless oil, (M+H)/Z=323.

Lactone E

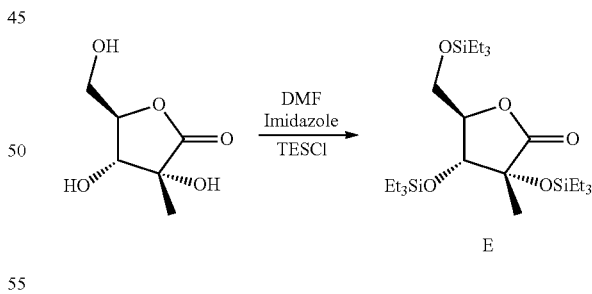

Lactone A (4.82 g, 29.7 mmol, 1.0 eq) was dissolved in 50 mL DMF. Imidazole (8.1 g, 119 mmol, 4 eq) was added. Triethylsilylchloride (17.9 g, 119 mmol, 4 eq) was then added over ~5 min and the mixture heated to 50° C. 2 mL methanol was added to quench the reaction. 50 mL toluene was added and the mixture washed sequentially with 40 mL water, 2×30 mL 5% NaHCO₃, and 25 mL sat'd. NaCl. The organics were dried over Na₂SO₄, filtered and concentrated to 14 g of a crude oil. The oil was purified by silica gel chromatography eluting with 10% EtOAc:hexanes to yield 9 g of Lactone E, (M+H)/Z=505.

Lactone F

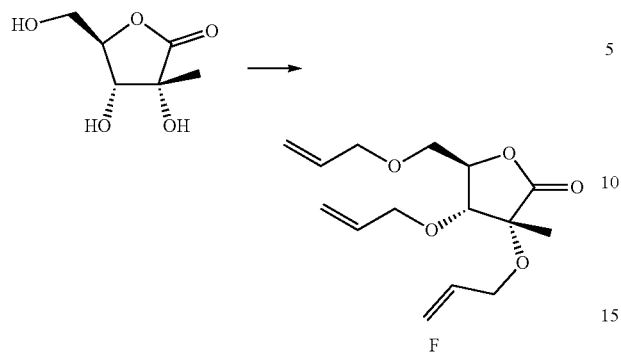

To a flask was charged NaH (1.60 g) and N,N-dimethylformamide (15 mL). The solution was cooled in an ice bath and lactone A (1.56 g) was added in DMF (3 mL) followed by a wash with DMF (1 mL) and the ice bath was removed. After 1 h, DMF (5 mL) was added to promote better stirring. The mixture was placed in an ice bath and allyl bromide (3.7 mL) was added and the ice bath removed. After stirring overnight the mixture was cooled in an ice bath and the reaction mixture carefully quenched with water (10 mL). To the mixture was added EtOAc (65 mL) and after agitation and separation the organics were washed with water and brine. The organics were dried over a mixture of Na$_2$SO$_4$ and MgSO$_4$, concentrated, and column purified on silica gel to give 1.1 g of the tri-allyl derivative, (M+H)/Z=283.

Lactone G

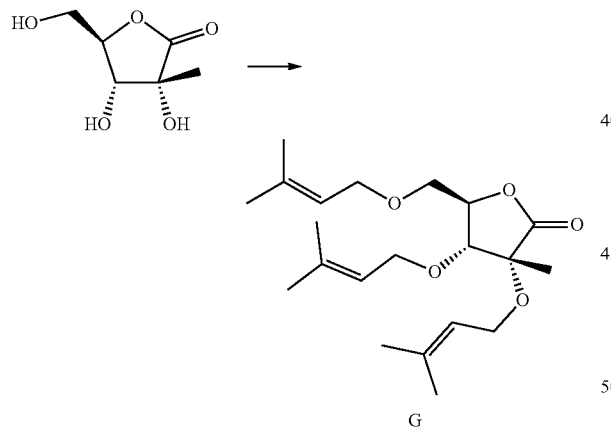

To a flask was charged NaH (1.7 g) and N,N-dimethylformamide (30 mL). The solution was cooled in an ice bath and Lactone A (1.57 g) was added in DMF (4 mL) followed by a wash with DMF (1 mL). The ice bath was removed and after 1.5 h the reaction mixture was cooled in an ice bath and 3,3-dimethylallyl bromide (5.2 mL) was added. The ice bath removed and the reaction left to stir overnight. The reaction mixture was cooled to 0° C. and was quenched with saturated NH$_4$Cl (3 mL) followed by diluting with water (27 mL) and EtOAc (100 mL). The organics were then washed with water and brine (30 mL each) and then dried over Na$_2$SO$_4$, filtered and concentrated. The residue was purified by column chromatography on silica gel giving 1.42 g (40%) of the tri-prenyl Lactone G, (M+H)/Z=367.

Lactone H

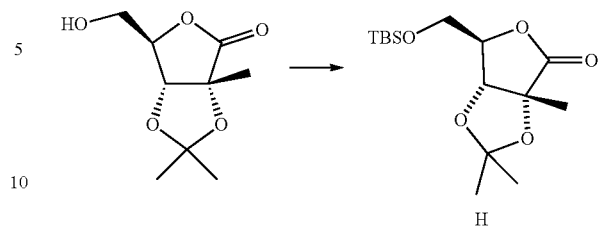

To a flask was charged the Lactone B (1.99 g) and DMF (20 mL). To the solution was added imidazole (1.00 g) and TBSCl (1.93 g) and the mixture was left to stir overnight. The next day water (20 mL) and EtOAc (50 mL) were added. The organics were then separated and washed with brine (20 mL), dried over Na$_2$SO$_4$, filtered and concentrated. The residue was purified by column chromatography on silica gel giving 2.75 g (88%) of the Lactone H, (M+H)/Z=317.

Compound 9

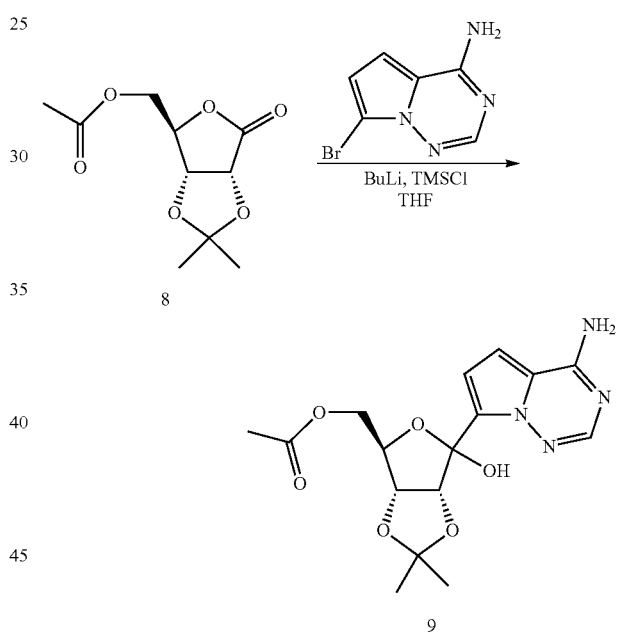

Compound 9 may be synthesized in the same manner as 1c by substituting Compound 8 (Ogura, et al. *J. Org. Chem.* 1972, 37, 72-75) for 1b in the reaction.

Compound 11

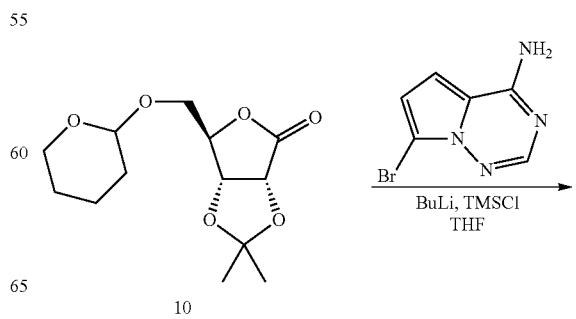

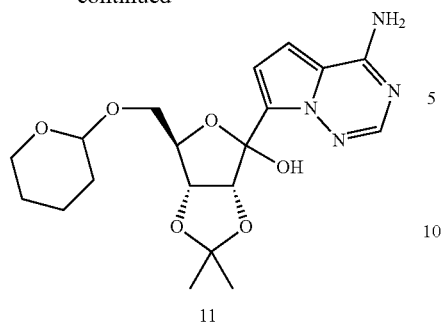

11

Compound 11 may be synthesized in the same manner as 1c by substituting Compound 10 (Ogura, et al. *J. Org. Chem.* 1972, 37, 72-75) for 1b in the reaction.

Compound 13

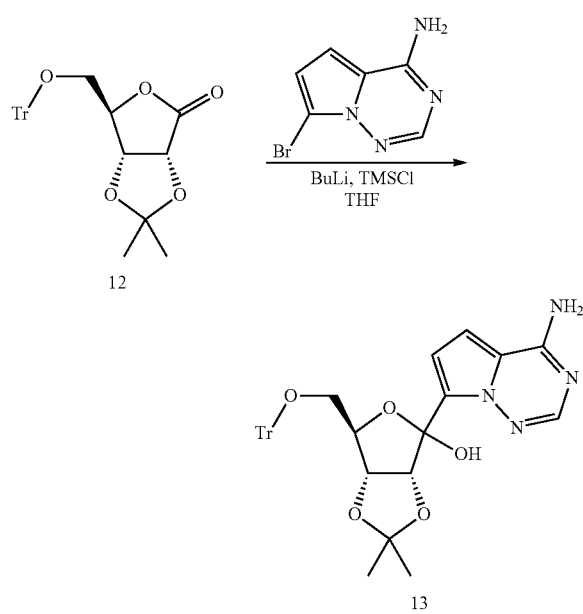

Compound 13 may be synthesized in the same manner as 1c by substituting Compound 12 (Camps, et al.; *Tetrahedron* 1982, 38, 2395-2402) for 1b in the reaction.

Compound 14

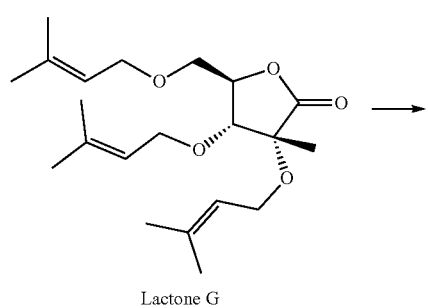

Lactone G

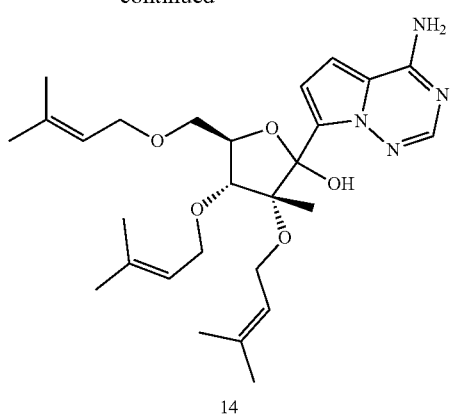

14

To 7-bromo-pyrrolo[2,1-f][1,2,4]triazin-4-ylamine (0.501 g) and THF (31.5 mL) was added 1,2-bis(chloromethylsilyl)ethane (0.518 g). To the cloudy solution was added NaH (60% in mineral oil, 0.235 g). After 10 minutes the solution was cooled in a −40° C. bath and nBuLi (2.16 M in hexanes, 3.6 mL) was added. After 13 min the lactone (1.031 g) was added in THF (3 mL) followed by a wash with 0.1 mL of THF. After 3 h the reaction mixture was at −20° C. and was quenched with saturated $NH_4Cl$ (3 mL) followed by the addition of water (7 mL). The solution was left to warm to room temperature overnight. The next day EtOAc (32 mL) was added and after separating the organics they were washed with water and brine (10 mL each). The organics were dried over $Na_2SO_4$, filtered, concentrated and the resulting residue purified by column chromatography on silica gel giving 0.567 g (48%) of the tri-prenyl protected lactol 14, (M+H)/Z=501.

Compound 15

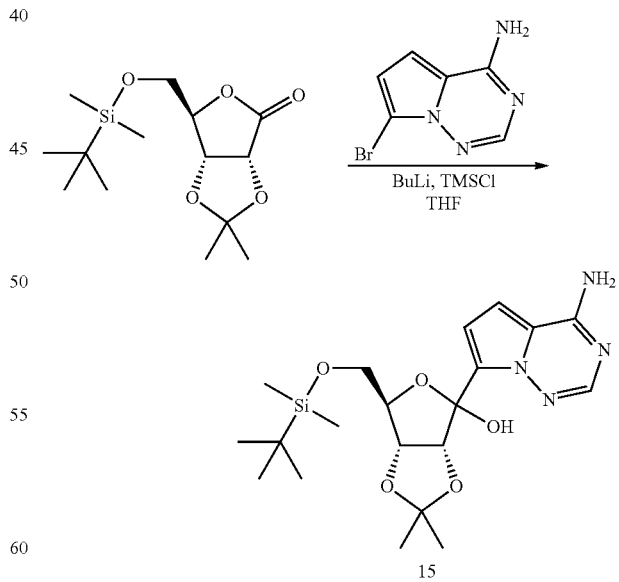

Compound 15 may be synthesized in the same manner as 1c by substituting the t-butylsilyl lactone depicted (Alessandrini, et al.; *J. Carbohydrate Chem.* 2008, 27, 322-344) for 1b in the reaction.

Compound 17

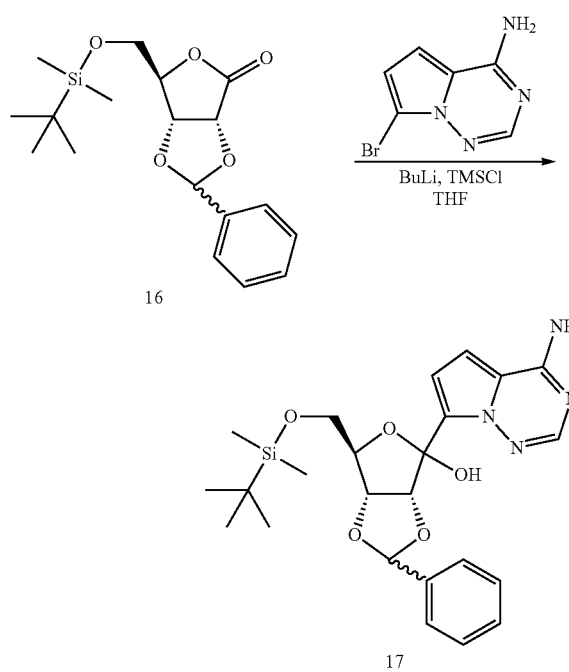

Compound 17 may be synthesized in the same manner as Ic by substituting Compound 16 (Alessandrini, et al.; *J. Carbohydrate Chem.* 2008, 27, 322-344) for 1b in the reaction.

Compound 19

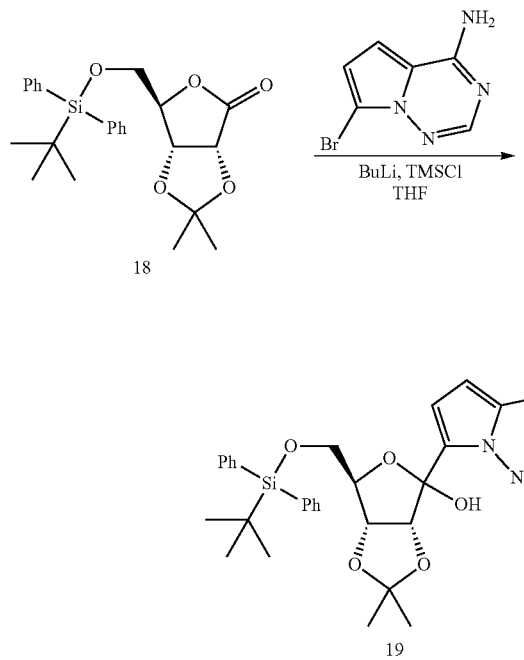

Compound 19 may be synthesized in the same manner as Ic by substituting Compound 18 (Piccirilli, et al.; *Helvetica Chimica Acta* 1991, 74, 397-406) for 1b in the reaction.

Compound 20

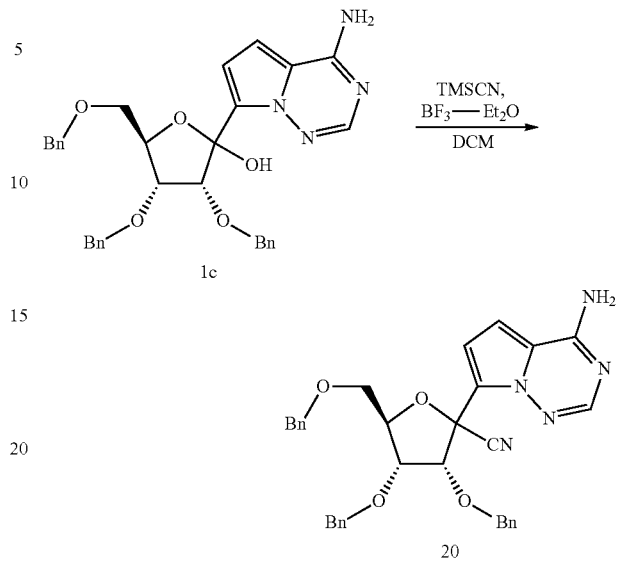

Compound 1c (0.28 g, 0.51 mmol) was dissolved in anhydrous dichloromethane (10 mL) and placed under nitrogen. Trimethylsilyl cyanide (0.35 mL) was added and the mixture was cooled to 0° C. After stirring for 10 min., boron trifluoride etherate (50 uL) was added and the reaction was allowed to warm to room temperature. When the reaction was complete by LC/MS, triethylamine was added to quench the reaction and solvents were removed by rotary evaporation. The residue was taken up in dichloromethane and loaded onto a silica gel column. A mixture of anomers was eluted using a gradient of 0-75% ethyl acetate and hexanes; 37% yield of 20. $^1$H-NMR (300 MHz, CD$_3$CN): δ 3.61-3.90 (m, 2H), 4.09-4.19 (m, 2H), 4.30-4.88 (m, 7H), 4.96 (d, 0.5H), 5.10 (d, 0.5H), 6.41 (bs, 2H), 6.73-6.78 (m, 1H), 6.81-6.88 (m, 1H), 7.17 (m, 2H), 7.39 (m, 13H), 7.86 (s, 0.5H), 7.93 (s, 0.5H).

Alternative Preparation of Compound 4 Using Trimethylsilyl Triflate as the Lewis Acid

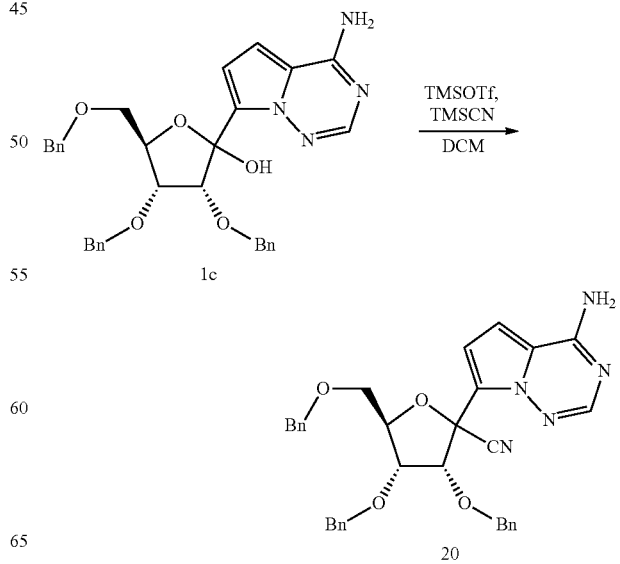

Compound 1c (1.1 g, 2.0 mmol) was dissolved in anhydrous dichloromethane (35 mL) and placed under nitrogen. Trimethylsilyl cyanide (1.21 mL, 9.1 mmol) was added and the mixture was cooled to 0° C. After stirring for 10 min., trimethylsilyl triflate (2.0 mL, 11 mmol) was added. When the reaction was complete by LC/MS (~2 h), dichloromethane (70 mL) was added to dilute followed by saturated sodium bicarbonate (70 mL). The mixture was stirred for 10 min. and the organic layer was collected by separatory funnel. The aqueous layer was extracted with dichloromethane, which was combined with the first organic extract. The solvents were removed by rotary evaporation. The residue was taken up in dichloromethane and loaded onto a silica gel column. A mixture of anomers was eluted using a gradient of 0-75% ethyl acetate and hexanes; 90% yield of 20.

Compound 21

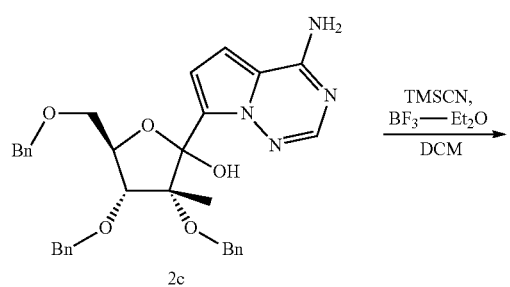

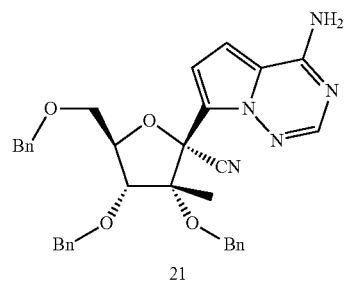

To a solution of compound 2c (1 g, 1.77 mmol) in CH$_2$Cl$_2$ (20 mL) at 0° C. was added TMSCN (1.4 mL, 10.5 mmol) and BF$_3$-Et$_2$O (1 mL, 8.1 mmol). The reaction mixture was stirred at 0° C. for 0.5 h, then at room temperature for additional 0.5 h. The reaction was quenched with NaHCO$_3$ at 0° C., and diluted with CH$_3$CO$_2$Et. The organic phase was separated, washed with brine, dried over Na$_2$SO$_4$, filtered and concentrated. The residue was purified by chromatography on silica gel, eluted with CH$_3$CO$_2$Et-hexanes (1:1 to 2:1), to give the desired compound 21 (620 mg, 61%). MS=576.1 (M+H$^+$).

Alternative Preparation of Compound 21

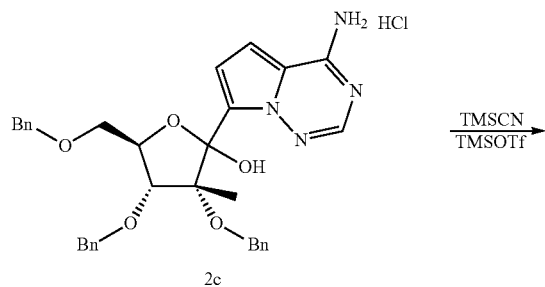

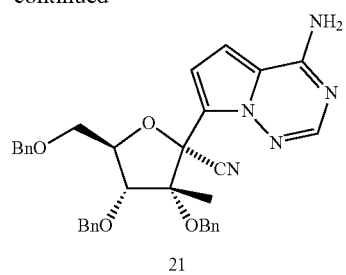

A flask was charged with 2c.HCl (53.2 g, 1 eq) and dichloromethane (530 mL). The slurry was cooled to −16° C. and TMSOTf (17.5 mL, 1.1 eq) was charged over 2 minutes while maintaining an internal temperature ←5° C.; the solution became homogeneous. When the reaction mixture was −14° C. the TMSCN (1.34 mL, 2.3 eq) was charged over 2 minutes. After 1 h, a solution of 10% (w/w) potassium carbonate/water (480 mL) was added followed by 45% (w/w) potassium hydroxide/water (53 mL) while maintaining a temperature of <0° C. The mixture was warmed to 20° C. and after the layers separated the organics were exchanged with acetonitrile followed by a wash with heptanes. The acetonitrile organics were concentrated and exchanged with DCM (200 mL) and concentrated to a foam giving 48.6 g (95%) of Compound 21, (M+H)/Z=576.

Compound 22

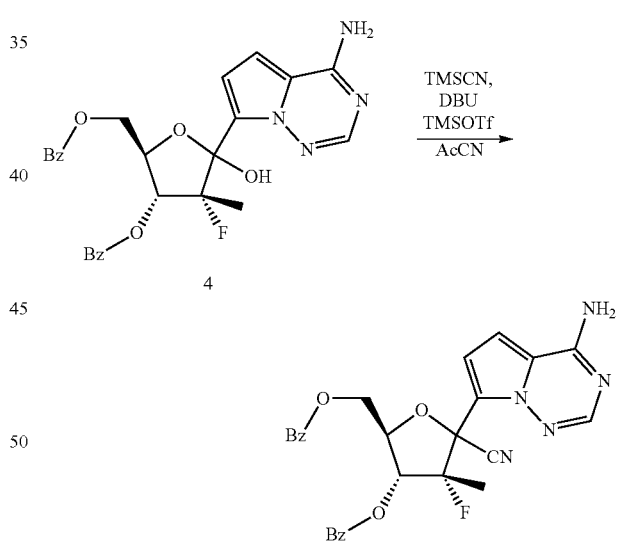

To a solution of compound 4 (50 mg, 0.1 mmol) and TMSCN (67 uL, 0.5 mmol) in acetonitrile (2.0 mL) at 0° C. was added TMSOTf (91 uL, 0.5 mmol). The reaction mixture was stirred at room temperature for 1 h, then at 65° C. for 3 d. The reaction was quenched with saturated NaHCO$_3$ at room temperature, and diluted with CH$_3$CO$_2$Et. The organic phase was separated, washed with brine, dried over Na$_2$SO$_4$, filtered and concentrated. The residue was purified by RP-HPLC (acetonitrile/water), to give the desired compound 22 (28 mg, 54%). MS=516.1 (M+H$^+$).

Alternative Preparation of Compound 22

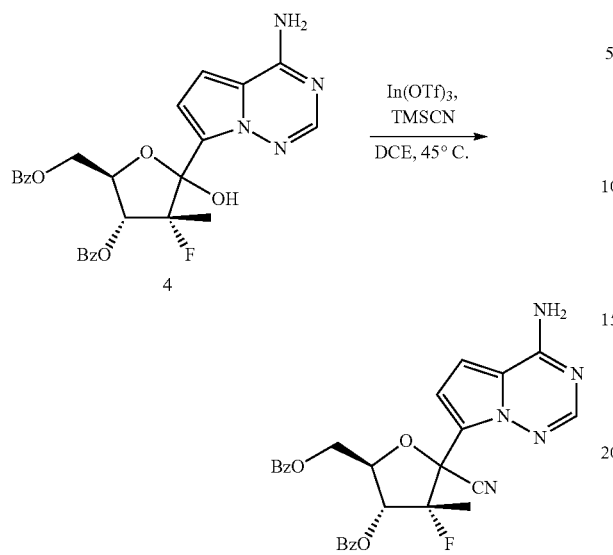

To a stirred solution of 4 (5 g, 10 mmol) in 1,2-dichloroethane (300 mL, 0.04M) under argon was added In(OTf)$_3$ (16.8 g, 30 mmol) and stirred for 5 min. The reaction mixture was then heated to 45° C. TMSCN (8.0 mL, 60 mmol) was added quickly. The reaction was allowed to progress overnight. The solvent was evaporated off, and the crude mixture was purified by silica gel chromatography (with Hex:EtOAc as eluent), affording compound 22 (~5 g).

MS [M+H$^+$]=516.3

Compound 23

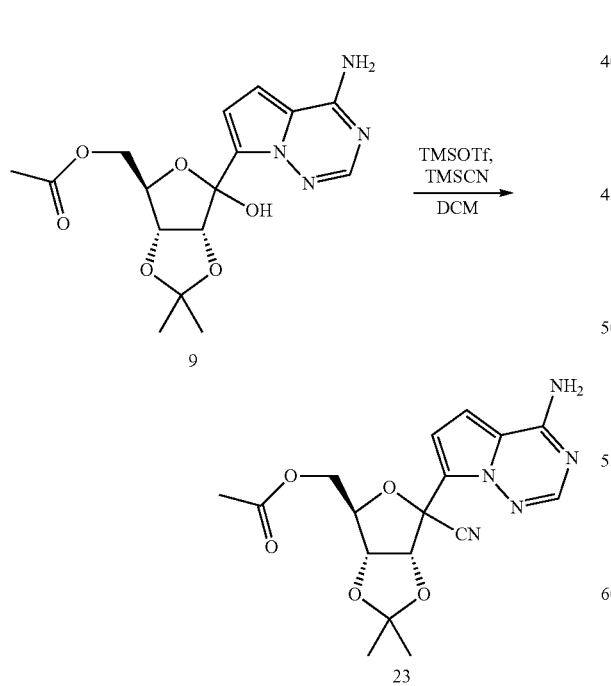

Compound 23 may be prepared in the same manner as Compound 20 by substituting Compound 9 for 1c.

Compound 24

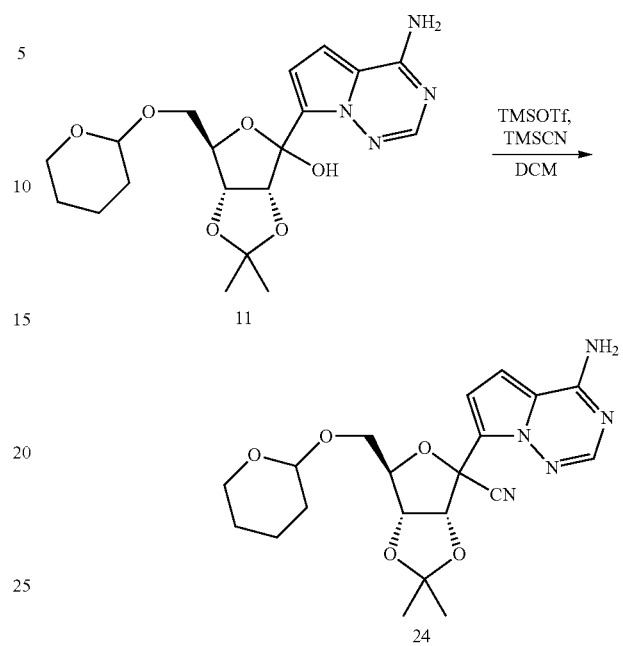

Compound 24 may be prepared in the same manner as Compound 20 by substituting Compound 11 for 1c.

Compound 25

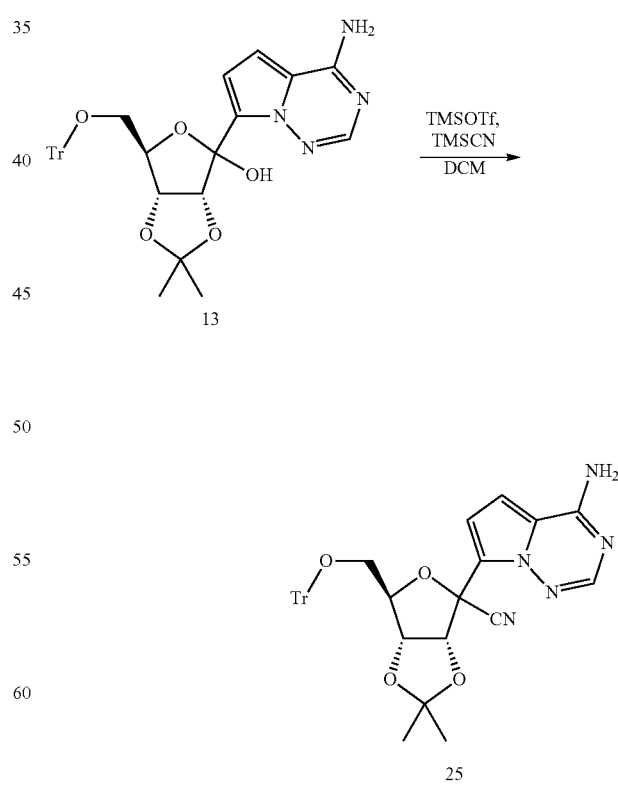

Compound 25 may be prepared in the same manner as Compound 20 by substituting Compound 13 for 1c.

Compound 26

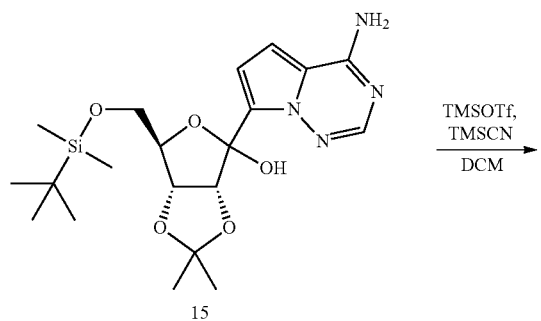

Compound 26 may be prepared in the same manner as Compound 20 by substituting Compound 15 for 1c.

Compound 27

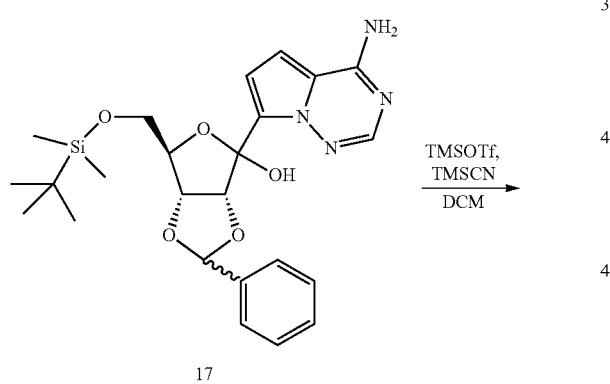

Compound 27 may be prepared in the same manner as Compound 20 by substituting Compound 17 for 1c.

Compound 28

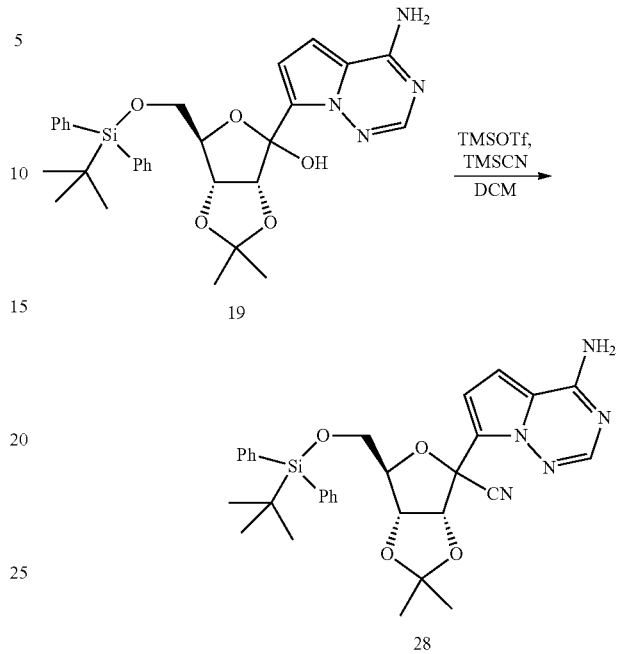

Compound 28 may be prepared in the same manner as Compound 20 by substituting Compound 19 for 1c.

Compound 29

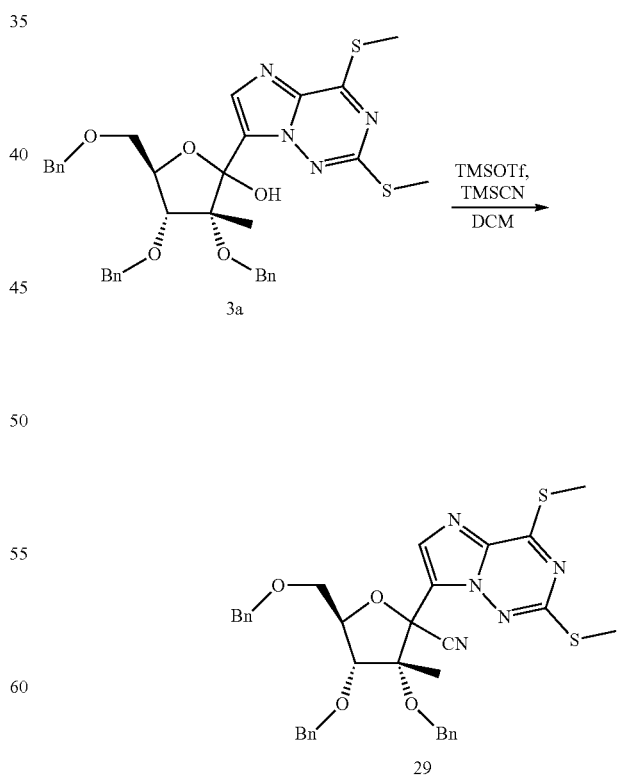

Compound 29 may be prepared in the same manner as Compound 20 by substituting Compound 3a for 1c.

Compound 30

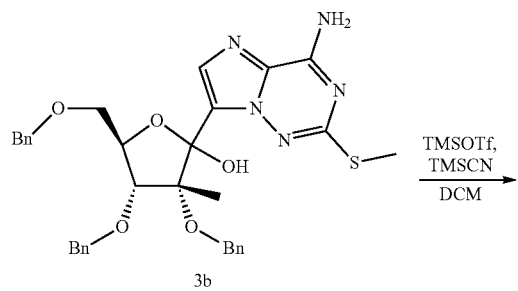

3b

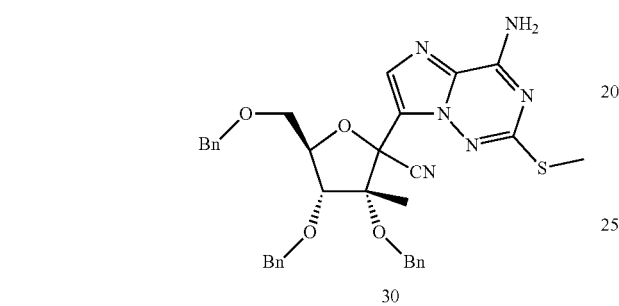

30

Compound 30 may be prepared in the same manner as Compound 20 by substituting Compound 3b for 1c.

Compound 31

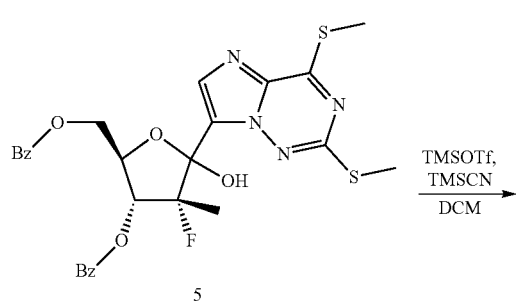

5

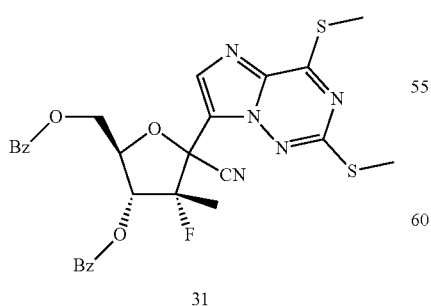

31

Compound 31 may be prepared in the same manner as Compound 20 by substituting Compound 5 for 1c.

Alternative Preparation of Compound 31

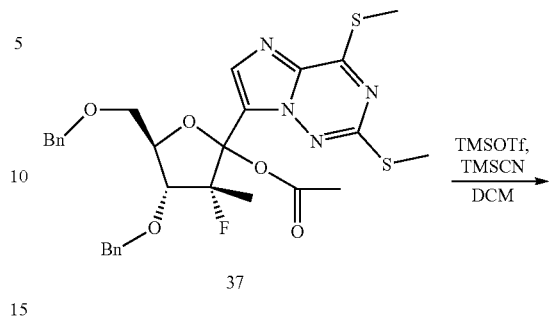

37

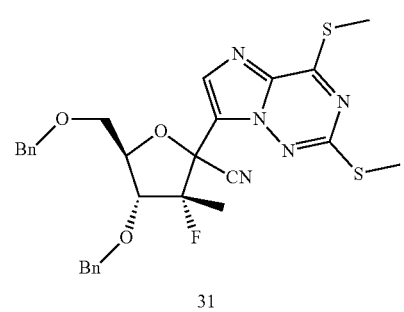

31

Compound 31 may also be prepared in the same manner as Compound 20 by substituting Compound 37 for 1c.

Compound 32

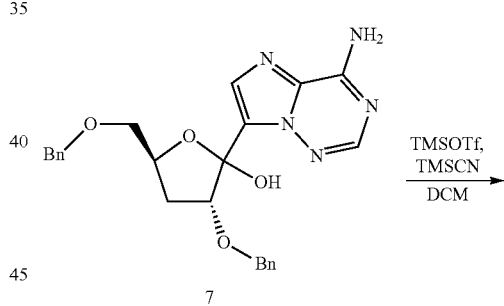

7

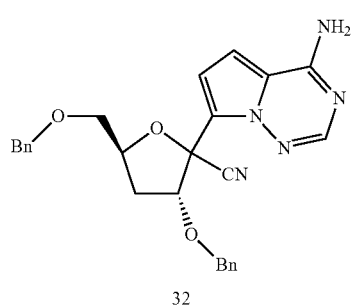

32

Compound 32 may be prepared in the same manner as Compound 20 by substituting Compound 7 for 1c.

Compound 33

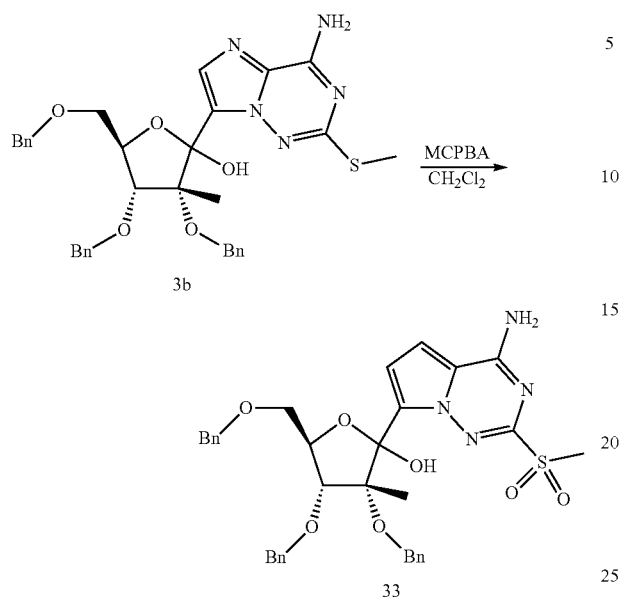

A solution of MCPBA (1.55 g, 8.96 mmol) in dichloromethane (20 mL) was dropwise added to a solution of 3b (2.5 g, 4.07 mmol) in dichloromethane (40 mL) while stirring. The resulting mixture was stirred at room temperature until complete disappearance of the starting material. After 3.5 h, the solvent was removed under reduced pressure and the crude material was purified using flash silica gel chromatography (hexanes/EtOAc). 2.0 g (77%) of the desired material 33 was isolated. LC/MS=646.2 (M+H+).

Compound 34

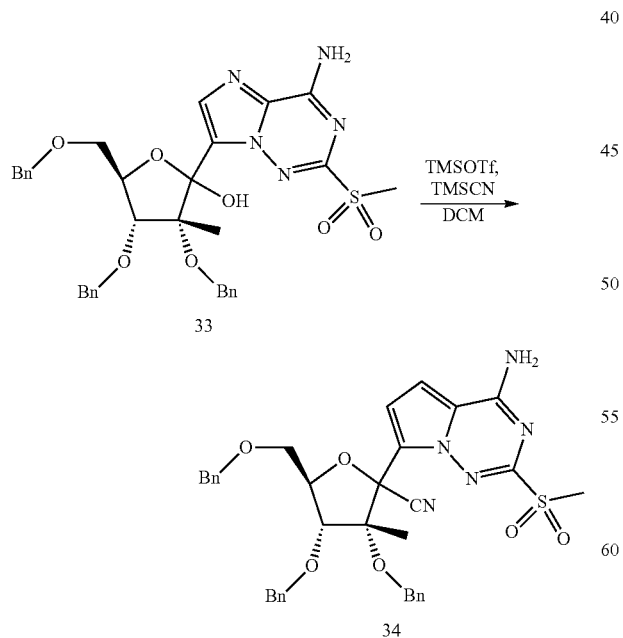

Compound 34 may be prepared in the same manner as Compound 20 by substituting Compound 33 for 1c.

Compound 35

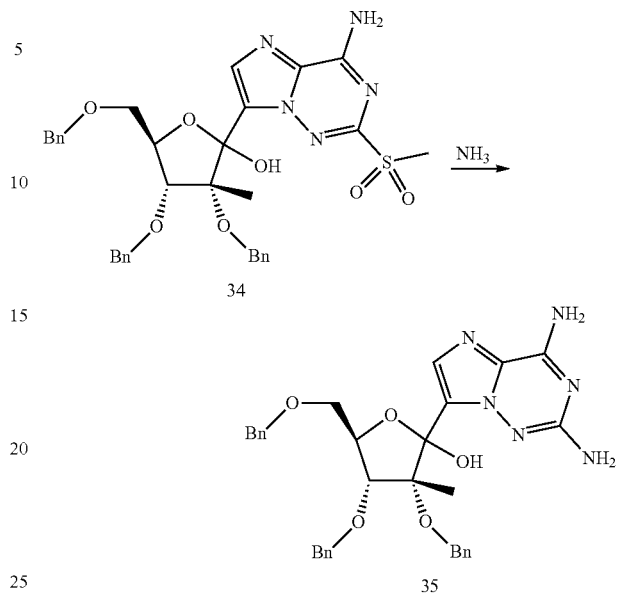

Compound 34 (2.0 g, 3.10 mmol) was dissolved in dichloromethane (15 mL) in a round bottom flask (50 mL) and then transferred to a steel bomb reactor. The solvent was removed under a positive flow of $N_2$ (g) and the solid material was treated with liquid $NH_3$ at −78° C. The tightly sealed bomb reactor was placed into a preheated oil bath at 110° C. and the reaction continued to proceed for 14 h. 1.8 g (100%) of the desired material 35 was isolated using MeOH and was used as is for the next reaction. LC/MS=583.3 (M+H$^+$)

Compound 36

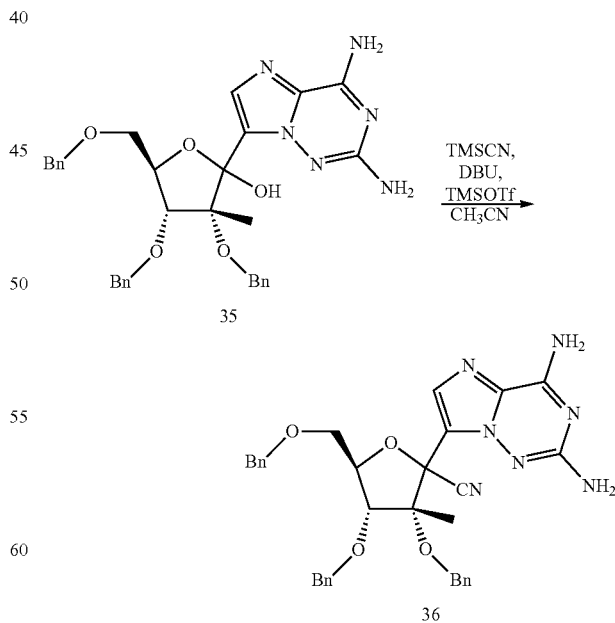

To a dry, argon purged round bottom flask (50 mL) were added 3,4-bis-benzyloxy-5-benzyloxymethyl-2-(2,4-di-amino-imidazo[2,1-f][1,2,4]triazin-7-yl)-3-methyl-tetrahydro-furan-2-ol 35 (800 mg, 1.37 mmol) and anhydrous MeCN (18 mL). The flask was cooled to 0° C. and DBU (1.02 mL, 6.85 mmol) was added. After 5 min of stirring, TMSOTf (1.49 mL, 8.22 mmol) was added to the flask followed by dropwise addition of TMSCN (1.10 mL, 8.22 mmol). The reaction mixture was allowed to warm to room temperature and the flask was then equipped with a reflux condenser and placed into a vessel preheated at 65° C. After 2 days of stirring, the flask was cooled to room temperature and then placed into an ice bath and the reaction was quenched with saturated NaHCO$_3$. EtOAc (3×10 mL) was used to extract the organic material and the combined organic layers were washed with brine (3×10 mL) and dried using MgSO$_4$. The solvent was removed under reduced pressure and the crude material was purified using flash chromatography (hexanes/EtOAc). 750 mg (93%) of the desired material 36 was isolated. LC/MS=592.3 (M+H$^+$).

Compound 37

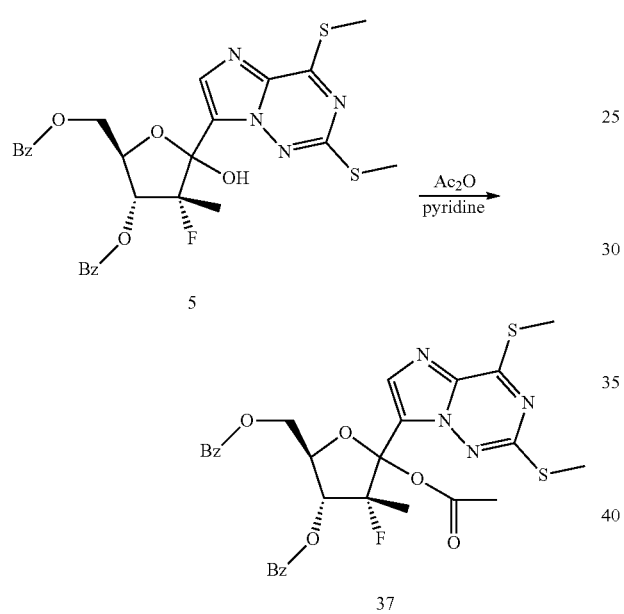

To a solution of 5 (300 mg, 0.51 mmol) in pyridine (1.5 mL) was added acetic anhydride (0.29 mL, 3.08 mmol) and stirred at 120° C. for 16 h. After cooling to room temperature, ethyl acetate and water were added. The ethyl acetate layer was taken, washed with dilute HCl followed by saturated ammonium chloride, dried over magnesium sulfate, and concentrated. The residue was purified by silica gel chromatography (dichloromethane/ethyl acetate), affording two stereoisomers of 37.

For fast moving isomer of 37; 26 mg, $^1$H NMR (400 MHz, CDCl$_3$): δ 8.39 (d, J=4.8 Hz, 1H), 8.00 (d, J=7.2 Hz, 2H), 7.98 (d, J=7.2 Hz, 2H), 7.59 (t, J=7.2 Hz, 1H), 7.51 (t, J=7.2 Hz, 1H), 7.45 (t, J=7.2 Hz, 2H), 7.38 (t, J=7.2 Hz, 2H), 6.39 (dd, J=8.2, 26.4 Hz, 1H), 5.61 (m, 1H), 4.77 (dd, J=2.6, 12.2 Hz, 1H), 4.25 (dd, J=4.8, 12.4 Hz, 1H), 2.68 (s, 3H), 2.61 (s, 3H), 1.68 (d, J=22.8 Hz, 3H), 1.54 (s, 3H). MS=627.0 (M+H$^+$).

For slow moving isomer of 37; 81 mg, $^1$H NMR (400 MHz, CDCl$_3$): δ 8.06 (d, J=7.2 Hz, 2H), 7.98 (d, J=7.2 Hz, 2H), 7.81 (d, J=4.8 Hz, 1H), 7.60 (t, J=7.2 Hz, 1H), 7.51 (t, J=7.2 Hz, 1H), 7.45 (t, J=7.2 Hz, 2H), 7.35 (t, J=7.2 Hz, 2H), 6.00 (dd, J=8.6, 23.8 Hz, 1H), 4.91 (m, 1H), 4.77 (dd, J=4.0, 12.4 Hz, 1H), 4.52 (dd, J=4.2, 12.2 Hz, 1H), 2.64 (s, 3H), 2.52 (s, 3H), 1.93 (s, 3H), 1.66 (d, J=22.4 Hz, 3H), MS=627.1 (M+H+).

Compound 38

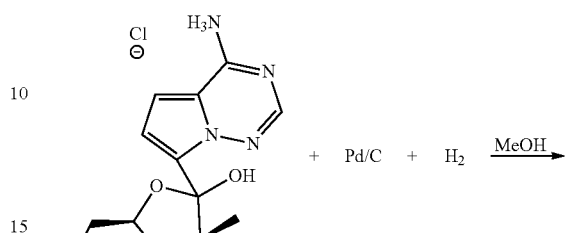

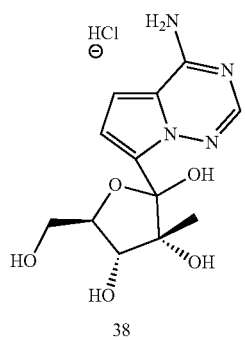

To a 3-neck flask under filled with N$_2$ was added 441 mg (0.2 mmol, 0.25 equiv.) Palladium (10% on C, Degussa type, 50% water content). This was suspended in MeOH (7.5 ml, 15 vol.), and then 500 mg (0.83 mmol, 1 equiv.) 2c-HCl was added. The reaction was placed under light vacuum, then under a H$_2$ atmosphere. After being stirred vigorously overnight, the reaction was found to be complete. The reaction mixture was filtered through celite, which was then rinsed several times with MeOH. The MeOH was removed under rotary evaporation, and the resulting oil was taken up in EtOAc, giving a white precipitate. This was filtered, providing Compound 38. Yield: 248 mg (90%), (M+H)/Z=297.

Compound 39

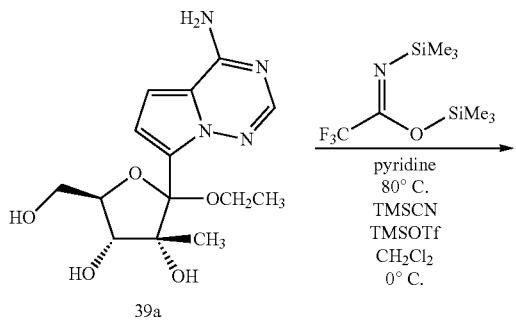

-continued

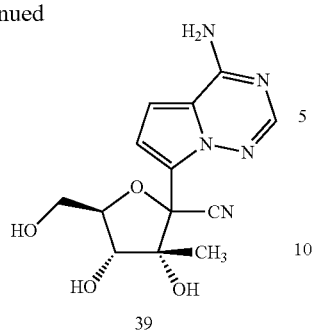

39

1.0 g of 39a (3.08 mmol) is combined with 10.0 mL pyridine (124.78 mmol) and 4.76 mL (N,O-bis(trimethylsilyl)trifluoroacetamide+1% TMSCl solution; 18.50 mmol, 6.0 equiv.). The mixture is heated to 80° C., and aged for on hour. Following 1.0 h age, the homogeneous yellow solution is cooled to 23° C., and aged with stirring for 18 h. Following aging, to the solution is added 10.0 mL toluene, and the mixture is concentrated by vacuum distillation to an orange oil. The oil is dissolved in 10.0 mL dichloromethane, and the solution is cooled to −10° C. To this cooled solution is added dropwise 2.51 mL TMSOTf (13.88 mmol, 4.5 equiv.) over a period of 30 min. Following TMSOTf addition, the mixture is aged at −5.0 C for 5 min. Following aging, 2.31 mL TMSCN (18.50 mmol, 6.0 equiv.) is added over 8 min. following TMSCN addition, the mixture is warmed to 23° C., and aged with stirring for 2.0 h. Following aging, the mixture is added to a solution of 7.0 g 25 wt % NaOMe/MeOH solution (32.0 mmol, 10.7 equiv.) cooled to 0° C. Following neutralization. the resulting mixture is concentrated to a viscous red oil. This oil is dissolved in 25 mL EtOAc, and to this solution is added 10 mL heptane. The precipitated solids are filtered, and washed with 20 mL EtOAc. The combined rinse and liquors are concentrated and purified by SiO$_2$ chromatography to afford the desired compound as a mixture of isomers, (M+H)/Z=306.

Compound 40

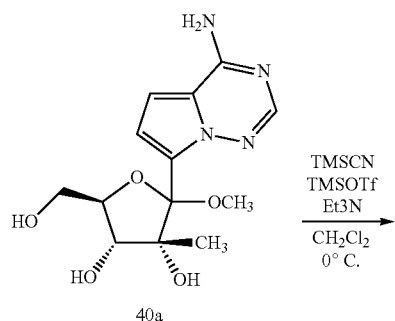

40a

-continued

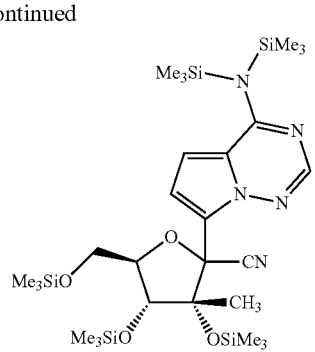

40

0.10 g 40a (0.232 mmol) is combined with 200.1 mg triethylamine (1.92 mmol, 6.0 equiv.) is suspended in 1.0 mL dichloromethane and this mixture is cooled to −5.0° C. To this heterogeneous suspension is added 470 µL TMSOTf (8.0 equiv.) over a period of 3 minutes with stirring. The mixture is aged @−5.0° C. for 10 minutes with stirring. Following age, to the cooled mixture is added 240 µL TMSCN (6.0 equiv.). The mixture is aged with stirring at 0° C. for an additional 2 h. The desired compound 40 is formed in ~50% by ANHPLC, (M+H)/Z=666.

Compounds 41-45

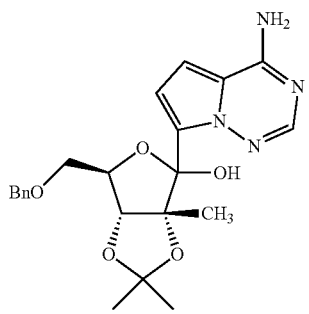

41

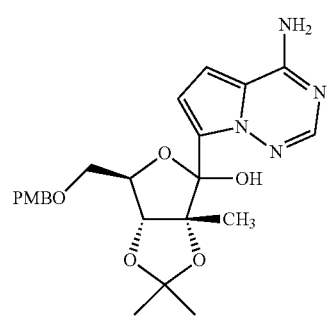

42

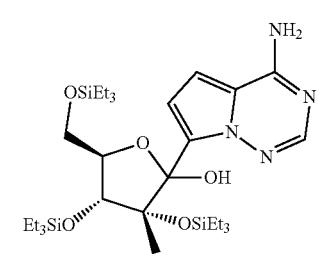

43

44

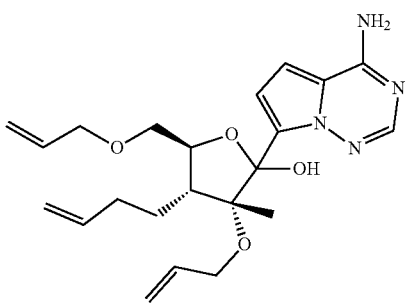

45

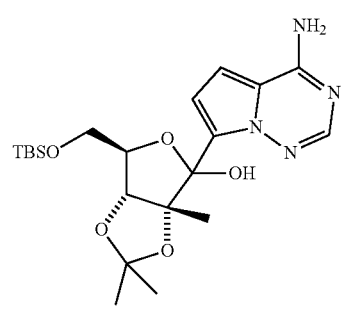

Using either Lactone C, D, E, F or H, Compounds 41, 42, 43, 44, or 45, respectively, may be prepared using the procedures described to prepare Compounds 2c or 14.

Compounds 46-51

46

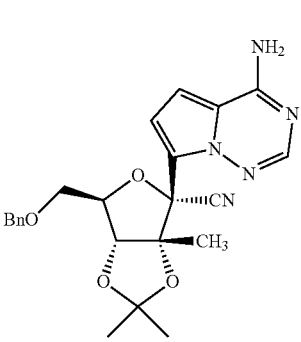

47

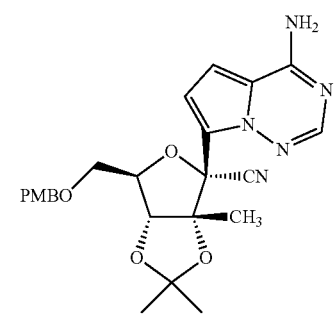

48

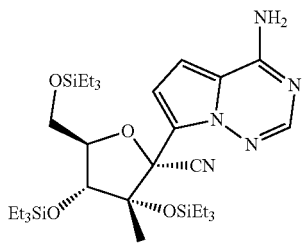

49

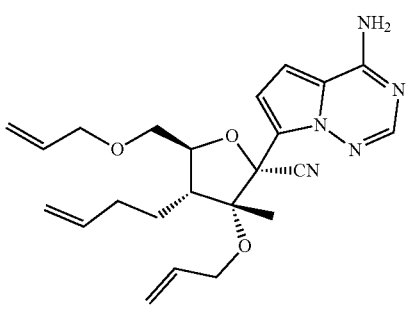

50

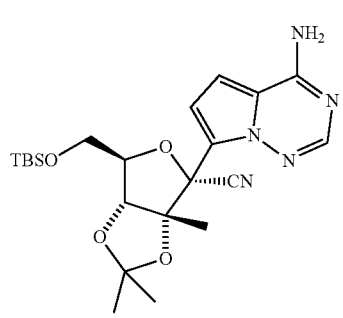

51

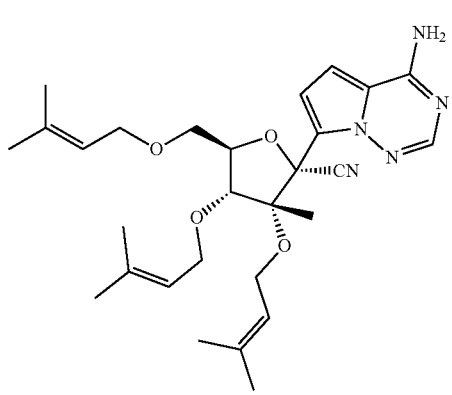

Using Compounds 41, 42, 43, 44, 45 or 14, respectively, Compounds 46, 47, 48, 49, 50 or 51, respectively, may be obtained using the cyanation procedures described for the examples disclosed herein.

All publications, patents, and patent applications cited herein above are incorporated by reference herein, as though individually incorporated by reference.

The invention has been described with reference to various specific and preferred embodiments and techniques. However, one skilled in the art will understand that many variations and modifications may be made while remaining within the spirit and scope of the invention.

What is claimed is:
1. A compound that is
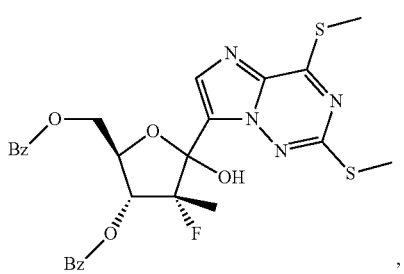
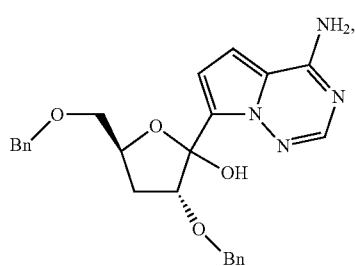
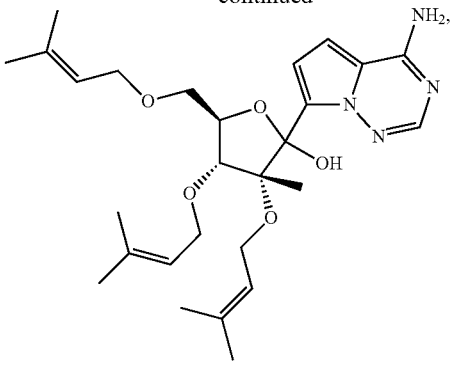
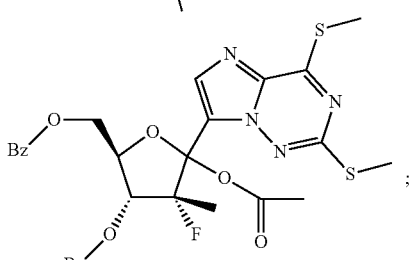
or an acceptable salt thereof.